United States Patent
Cohen et al.

(10) Patent No.: US 11,161,801 B2
(45) Date of Patent: Nov. 2, 2021

(54) CATIONIC PILLARARENES AND USES THEREOF

(71) Applicant: RAMOT AT TEL-AVIV UNIVERSITY LTD., Tel Aviv (IL)

(72) Inventors: Yoram Cohen, Tel Aviv (IL); Micha Fridman, Tel Aviv (IL); Roymon Joseph, Tel Aviv (IL); Alissa Naugolny, Tel Aviv (IL); Mark Feldman, Tel Aviv (IL); Ido M. Herzog, Tel Aviv (IL); Dana Kaizerman, Tel Aviv (IL)

(73) Assignee: Ramot At Tel-Aviv University Ltd., Tel Aviv (IL)

( * ) Notice: Subject to any disclaimer, the term of this patent is extended or adjusted under 35 U.S.C. 154(b) by 252 days.

(21) Appl. No.: 15/751,786

(22) PCT Filed: Aug. 3, 2016

(86) PCT No.: PCT/IL2016/050848
§ 371 (c)(1),
(2) Date: Feb. 9, 2018

(87) PCT Pub. No.: WO2017/025951
PCT Pub. Date: Feb. 16, 2017

(65) Prior Publication Data
US 2020/0172471 A1 Jun. 4, 2020

(30) Foreign Application Priority Data
Aug. 10, 2015 (IL) .......................................... 240479

(51) Int. Cl.
C02F 1/50 (2006.01)
C07C 217/54 (2006.01)
C07D 233/60 (2006.01)
C07F 9/54 (2006.01)
C09D 5/16 (2006.01)
A61K 31/138 (2006.01)
A61K 31/4178 (2006.01)
A61K 31/66 (2006.01)
A61K 45/06 (2006.01)

(52) U.S. Cl.
CPC .......... C07C 217/54 (2013.01); A61K 31/138 (2013.01); A61K 31/4178 (2013.01); A61K 31/66 (2013.01); A61K 45/06 (2013.01); C02F 1/50 (2013.01); C07D 233/60 (2013.01); C07F 9/5407 (2013.01); C09D 5/1687 (2013.01); C02F 2303/20 (2013.01)

(58) Field of Classification Search
CPC .. A61P 31/04; A61P 31/00; C02F 1/50; C02F 2303/20; C07C 217/54; C07C 59/72; C07C 2603/92; C07C 217/20; C07D 233/60; C07F 9/5407
See application file for complete search history.

(56) References Cited

FOREIGN PATENT DOCUMENTS

CN 104447363 3/2015
WO WO 2013/104916 7/2013

OTHER PUBLICATIONS

Ogoshi et al. Chem. Commun. 2012, 48, 3536. (Year: 2012).*
Chen et al. "Synthesis of a cationic water-soluble pillar[6]arene and its effective complexation towards naphthalenesulfonate guests" Chem. Commun. 2013, 49, 7956. (Year: 2013).*
Si et al. "Voltage-Driven Reversible Insertion into and Leaving from a Lipid Bilayer: Tuning Transmembrane Transport of Artificial Channels" Angew. Chem. Int. Ed. 2014, 53, 4578-4581. (Year: 2014).*
Nierengarten et al. "A mannosylated pillar[5]arene derivative: chiral information transfer and antiadhesive properties against uropathogenic bacteria" Tet. Lett. 2013, 54, 2398-2402. (Year: 2013).*
Adiri, T. et al; "Potential 129Xe-NMR biosensors based on secondary and tertiary complexes of a water-soluble pillar[5]arene derivative" Commun., 49, pp. 7082-7084. (2013).
Chen Wei, et. al; "Synthesis of a cationic water-soluble pillar[6]arene and its effective complexation towards naphthalenesulfonate guests." Chemical Communications 49, No. 72 : 7956-7958. (2013).
Cragg, P. J.et al; "Pillar[5]arenes: fascinating cyclophanes with a bright futurew" Chem. Soc. Rev., 41, pp. 597-607. (2012).
Gui-yuan Wu et al; "A cationic water-soluble pillar[5]arene: synthesis and host-guest complexation with long linear acids" RSC Advances, 5, pp. 4958-4963. (2015).
Guocan Yu, et. al; "A Sugar-Functionalized Amphiphilic Pillar[5]arene: Synthesis, Self-Assembly in Water, and Application in Bacterial Cell Agglutination", J. Am. Chem. Soc., 135 (28), pp. 10310-10313. (2013).
International Search Report and Written Opinion received in PCT Application No. PCT/IL2016/050848, dated Nov. 7, 2016.
Ma, Y.;et al; "A cationic water-soluble pillar[5]arene: synthesis and host-guest omplexation with sodium 1-octanesulfonatew" Chem. Commun., , 47, pp. 12340-12342. (2011).
Melezhyk et. al; "Antibacterial Properties of tetraalkylammonium and Imidazolium Tetraalkoxycalix[4]arene Derivatives", Anti-Infective Agents., vol. 13, No. 1, pp. 87-94. (2015).
Nierengarten I., et al; "A mannosylated pillar[5]arene derivative: chiral information transfer and antiadhesive properties against uropathogenic bacteria Tetrahedron" Letters, vol. 54, Issue 19, pp. 2398-2402. (2013).

(Continued)

Primary Examiner — Amanda L. Aguirre
(74) Attorney, Agent, or Firm — Knobbe Martens Olson & Bear, LLP

(57) ABSTRACT

The present invention provides cationic pillar[n]arenes, e.g., positively charged poly-ammonium, poly-phosphonium and poly-imidazolium pillar[5-6]arene derivatives, capable of inhibiting or preventing biofilm formation, and facilitating existing biofilm decomposition; as well as compositions thereof and methods of use.

17 Claims, 12 Drawing Sheets

(56) References Cited

OTHER PUBLICATIONS

Ogoshi et al; "Synthesis and Conformational Characteristics of Alkyl-Substituted Pillar[5]arenes" J. Org. Chem., 75, pp. 3268-3273. (2010).

Ogoshi Tomoki, et al; "An amphiphilic pillar[5]arene as efficient and substrate-selective phase-transfer catalyst." Organic letters 15, No. 14. pp. 3742-3745. (2013).

Ogoshi Tomoki, et al; "Ionic liquid pillar[5] arene: its ionic conductivity and solvent-free complexation with a guest." Chemical Communications 48, No. 29 pp. 3536-3538.(2012).

Qi Zhenhui, et al; "Supramolecular hydrophobic guest transport system based on pillar[5] arene". Chemical Communications, No. 51 : pp. 10326-10329. (2015).

Si Wen, et al; "Voltage-Driven Reversible Insertion into and Leaving from a Lipid Bilayer: Tuning Transmembrane Transport of Artificial Channels" Angewandte Chemie International, edition 53, No. 18 pp. 4578-4581.(2014).

Xue, M.;et al; "Pillararenes, A New Class of Macrocycles for Supramolecular Chemistry" Acc. Chem. Res., 45, pp. 1294-1308.(2012).

Yao Y., et al; "A new water-soluble pillar [5] arene: synthesis and application in the preparation of gold nanoparticles." Chem. Comm., vol. 48 pp. 6505-6507. (2012).

Yao Yong, et. al; "Water-soluble pillar [6] arene stabilized silver nanoparticles: preparation and application in amino acid detection." Tetrahedron Letters 55, No. 20 pp. 3195-3199. (2014).

Zhou Jun, et al; "Synthesis of the first amphiphilic pillar[6]arene and its enzyme-responsive self-assembly in water." Chemical Communications 50, No. 80 pp. 11954-11956. (2014).

Extended European Search Report received in EP Application No. EP 16 83 4760, dated Feb. 12, 2019.

Joseph et al., "Phosphonium pillar[5]arenes as a new class of efficient biofilm inhibitors: importance of charge cooperativity and the pillar platform" Chemical Communications, 52(70), pp. 10656-10659 (2016).

Joseph et al.,"Cationic Pillararenes Potently Inhibit Biofilm Formation without Affecting Bacterial Growth and Viability" Journal of the American Chemistry Society, 138(3), pp. 754-757. (2016).

\* cited by examiner

CATIONIC PILLARARENES AND USES THEREOF

This application is the U.S. National Phase under 35 U.S.C. § 371 of International Application No. PCT/IL2016/050848 filed Aug. 3, 2016, designating the U.S. and published as WO 2017/025951 on Feb. 16, 2017 which claims the benefit of Israel Patent Application No. 240479 filed Aug. 10, 2015.

TECHNICAL FIELD

The present invention relates to cationic pillar[n]arenes, e.g., cationic pillar[5-6]arenes, and uses thereof in inhibiting or disrupting biofilm formation, or reducing biofilm.

BACKGROUND ART

Bacterial biofilms are defined as microbial communities (cities of microbes) that are held together by an extracellular matrix. In recent years, there is an increasing interest in bacterial biofilms as a result of the fact that in the majority of the cases biofilms lead to a dramatic enhancement in resistance to antimicrobial agents (Fux et al., 2005; Davies, 2003; Rabin et al., 2015). Compared with planktonic bacteria (bacteria that grow in suspension), biofilm forming bacteria can be up to almost three orders of magnitude less susceptible to antibiotics (Bottcher et al., 2013). Moreover, it was estimated that biofilms account for a large percentage of nosocomial and implanted device-derived microbial infections in patients (Davey and O'Toole, 2000).

Biofilm matrices are composed of exo-polymeric substances (EPS) that are high-molecular weight compounds secreted by the bacteria into the extracellular environment and are crucial for the integrity of all biofilms (Bottcher et al., 2013; Davey and O'Toole, 2000). EPS components include polysaccharides also termed exo-polysaccharides, proteins, extracellular DNA, lipids and bacterial decomposition substances that are held together by a highly complex network of hydrogen bonds as well as ionic and van der Waals interactions between the different matrix components. The composition of biofilm matrices varies significantly amongst different bacterial strains; some matrices contain mainly exo-polysaccharides and some mainly proteins. Moreover, the structure of the proteins and the monosaccharide building blocks that compose exo-polysaccharides vary between different biofilm producing bacterial strains.

Investigation of the biofilm formation process in the Gram negative *Pseudomonas aeruginosa* which is one of the major causes for lethal bacterial lung infections revealed a biofilm formation process that was generally defined as a five step sequence described in FIG. 1 (Jennings et al., 2014). In the first stage, planktonic bacteria adhere to the surface on which the biofilm is about to form. At this point, most of the interactions with the surface are based on van-der Waals reversible forces and the bacterial cell can easily leave the surface back into the media. Once these weak initial interactions took place, in the second stage, the bacterial cells more permanently anchor themselves to the surface by a cell adhesion process that involves protein based interactions. In the third and fourth stages, additional bacterial cell layers adhere to the first layer and form micro colonies that continue to grow and mature by forming an extracellular matrix coating. In the final fifth stage, biofilm forming bacterial cells leave the mature biofilm into the environment and remain as planktonic bacteria or establish new biofilm colonies depending on the environmental conditions.

Clardy and coworkers previously reported a collection of synthetic guanidine- and bi-guanidine-based cationic amphiphiles that inhibited biofilm formation as well as eradicated existing biofilms of *Bacillus subtillis* and *Staphylococcus aureus* strains (Bottcher et al., 2013). More recently, Wuest and coworkers reported a collection of quaternary ammonium amphiphiles (Jennings et al., 2014) that demonstrated antimicrobial activity against a collection of Gram positive and Gram negative bacterial strains. In addition, some of these cationic amphiphiles efficiently broke down existing biofilms of the two Gram positive pathogens *Staphylococcus aureus* and *Enterococcus faecalis*. However it was reported that these molecules are all hemolytic compounds exhibiting pronounced toxicity against mammalian cells (Jennings et al., 2014).

Pillar[n]arenes, first reported in 2008 (Ogoshi et al., 2008), have symmetrical cylindrical structures and relatively large free volumes. Pillar[n]arenes can be obtained and functionalized by simple and high yield synthesis routes making them a versatile macrocycles for various applications. These macrocycles possess host-guest properties owing to their π-electron rich cavity and crown ether-like arrangement of oxygen atoms at both rims. Hence, in recent years, pillar[n]arenes have been used in host-guest chemistry and as sensors and were used to construct supramolecular polymers, interlocked molecules, and hybrid biomolecular materials (Ogoshi et al., 2008; Ogoshi and Yamagishi, 2014; Cragg and Sharma, 2012; Xue et al., 2012; Dong et al., 2014a; Chunju, 2014; Ogoshi et al., 2016; Ma et al., 2016; Liz et al., 2016; Shi et al., 2016; Ogoshi et al., 2015; Nierengarten et al., 2013; Li, 2014; Yang et al., 2014; Adiri et al., 2013; Zhang and Zhao, 2013; Yao et al., 2014; Dong et al., 2014b; Mao et al., 2016; Wang et al., 2015; Jie et al., 2014). Despite the significant attention that pillararenes have received from the chemical community, to date, their biological activity remains relatively unexplored.

Despite the great need, there are currently no clinically approved small molecules that act as efficient inhibitors of biofilm formation and/or as eradicators of mature biofilms, without affecting bacterial cell viability. Identification of such small molecules will offer a much needed solution to biofilm infections while not affecting the important natural bacterial flora of the body. In addition, it is likely that the bacteria will not develop any defense mechanisms against such biofilm inhibitors or eradicators.

SUMMARY OF INVENTION

In one aspect, the present invention provides a compound of the formula I:

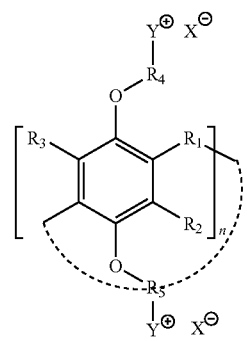

wherein $R_1$ is —$CR_6R_7$—, wherein $R_6$ and $R_7$ each independently is H, halogen, —$COR_8$, —$COOR_8$, —$OCOOR_8$, —$OCON(R_8)_2$, —$CN$, —$NO_2$, —$SR_8$, —$OR_8$, —$N(R_8)_2$, —$CON(R_8)_2$, —$SO_2R_8$, —$SO_3H$, —$S(=O)R_8$, or $(C_1-C_8)$alkyl optionally substituted by one or more groups each independently selected from —$COR_8$, —$COOR_8$, —$OCOOR_8$, —$OCON(R_8)_2$, —$CN$, —$NO_2$, —$SR_8$, —$OR_8$, —$N(R_8)_2$, —$CON(R_8)_2$, —$SO_2R_8$, —$SO_3H$, —$S(=O)R_8$, —$N^+(R')_3$ or —$P^+(R')_3$, wherein R' each independently is H, $(C_1-C_6)$ alkyl, phenyl, benzyl, or heterocyclyl, or two R's together with the N atom to which they are attached form a 3-7 membered saturated ring, optionally containing one or more heteroatoms selected from O, S or N and optionally further substituted at the additional N atom;

$R_2$ and $R_3$ each independently is H, halogen, or $(C_1-C_8)$ alkyl optionally substituted by one or more groups each independently selected from halogen, —$COR_8$, —$COOR_8$, —$OCOOR_8$, —$OCON(R_8)_2$, —$CN$, —$NO_2$, —$SR_8$, —$OR_8$, —$N(R_8)_2$, —$CON(R_8)_2$, —$SO_2R_8$, —$SO_3H$, —$S(=O)R_8$, —$P^+(R')_3$ or —$P^+(R')_3$, wherein R' each independently is H, $(C_1-C_6)$alkyl, phenyl, benzyl, or heterocyclyl, or two R's together with the N atom to which they are attached form a 3-7 membered saturated ring, optionally containing one or more heteroatoms selected from O, S or N and optionally further substituted at the additional N atom;

$R_4$ and $R_5$ each independently is selected from $(C_1-C_{10})$ alkylene, $(C_2-C_{10})$alkenylene, or $(C_2-C_{10})$alkynylene, optionally substituted by one or more groups each independently selected from halogen, —$COR_8$, —$COOR_8$, —$OCOOR_8$, —$OCON(R_8)_2$, —$CN$, —$NO_2$, —$SR_8$, —$OR_8$, —$N(R_8)_2$, —$CON(R_8)_2$, —$SO_2R_8$, —$SO_3H$, —$S(=O)R_8$, $(C_6-C_{10})$aryl, $(C_1-C_4)$alkylene-$(C_6-C_{10})$aryl, heteroaryl, or $(C_1-C_4)$alkylene-heteroaryl, and further optionally interrupted by one or more identical or different heteroatoms selected from S, O or N, and/or at least one group each independently selected from —NH—CO—, —CO—NH—, —$N(C_1-C_8$alkyl)-, —$N(C_6-C_{10}$aryl)-, $(C_6-C_{10})$arylenediyl, or heteroarylenediyl;

$R_8$ each independently is H or $(C_1-C_5)$alkyl;

Y each independently is a cation derived from a nitrogen-containing group, a nitrogen-containing mono- or polycyclic heteroaromatic group optionally containing O, S or additional N atoms, or an onium group not containing nitrogen, linked to $R_4$ or $R_5$ via its positively charged atom;

X is a counter anion such as $Br^-$, $Cl^-$, $F^-$, $I^-$, $PF_6^-$, $BF_4^-$, $OH^-$, $ClO_4^-$, $HSO_4^-$, $CF_3COO^-$, $CN^-$, alkyl$COO^-$, aryl$COO^-$, a pharmaceutically acceptable anion, or a combination thereof; and n is an integer of 5-11, but excluding the compounds wherein $R_1$ is —$CH_2$—; $R_2$ and $R_3$ are H; and: (i) n is 5; $R_4$ and $R_5$ are —$(CH_2)_2$—; and Y is 1-methyl-imidazolium-3-yl or —$N^+(CH_3)_3$; (ii) n is 5; $R_4$ and $R_5$ are —$(CH_2)_3$—; and Y is —$P^+(C_4H_9)_3$; (iii) n is 5; $R_4$ and $R_5$ are —$(CH_2)_4$—; and Y is —$N^+(CH_3)_3$; (iv) n is 6; $R_4$ and $R_5$ are —$(CH_2)_2$—; and Y is —$N^+(CH_3)_3$; (v) n is 6; $R_4$ and $R_5$ are —$(CH_2)_4$—; and Y is —$N^+(CH_3)_3$; (vi) n is 6; $R_4$ and $R_5$ are —$(CH_2)_4$—; and Y is 1-pyridinium; or (vii) n is 6; $R_4$ and $R_5$ are —$(CH_2)_2$—; and Y is 1-methyl-imidazolium-3-yl.

More particularly, the invention provides a compound of the formula I as defined above, wherein Y each independently is (i) a cation derived from a nitrogen-containing group and selected from an ammonium [—$N^+(R')_3$], hydrazinium [—$N^+(R')_2$—$N^+(R')_2$], ammoniumoxy [—$N^+(R')_2$→O], iminium [—$N^+(R')_2$=C<], amidinium [—$N^+(R')_2$—$C(R')$=NR'], or guanidinium [—$N^+(R')_2$—$C(=NR')$—$N(R')_2$]; (ii) a cation derived from a nitrogen-containing mono- or polycyclic heteroaromatic group and selected from pyrazolium, imidazolium, oxazolium, thiazolium, pyridinium, pyrimidinium, quinolinium, isoquinolinium, 1,2,4-triazinium, 1,3,5-triazinium, or purinium, optionally substituted by one or more groups each independently selected from halogen, $(C_1-C_6)$alkyl, —COH, —COOH, —OCOOH, —OCONH$_2$, —CN, —NO$_2$, —SH, —OH, —NH$_2$, —CONH$_2$, —SO$_3$H, —SO$_2$H, or —S(=O)H; or (iii) a cation derived from an onium group not containing nitrogen and selected from phosphonium [—$P^+(R')_3$], arsonium [—$As^+(R')_3$], oxonium sulfonium [—$S^+(R')_2$], selenonium [—$Se^+(R')_2$], telluronium [—$Te^+(R')_2$], stibonium [—$Sb^+(R')_3$], or bismuthonium [—$Bi^+(R')_3$], wherein R' each independently is H, $(C_1-C_6)$ alkyl, phenyl, benzyl, or heterocyclyl, or two R's in the ammonium, hydrazinium, ammoniumoxy, iminium, amidinium or guanidinium groups, together with the N atom to which they are attached, form a 3-7 membered saturated ring, optionally containing one or more heteroatoms selected from O, S or N and optionally further substituted at the additional N atom.

In another aspect, the present invention provides a composition comprising a compound of the formula I as defined above, i.e., excluding the compounds excluded by the proviso above, and a carrier.

In a further aspect, the present invention relates to a method for inhibiting or disrupting biofilm formation in an aqueous media or on an object, or for reducing biofilm existing in an aqueous media or attached to an object, said method comprising contacting said aqueous media or object with a compound of the formula I, including the compounds excluded by the proviso above.

In certain embodiments, the method of the present invention is for inhibiting or disrupting biofilm formation in an aqueous media, or for reducing biofilm existing in said aqueous media, and comprises in fact dissolving of said compound or a composition comprising it within said aqueous media. In other embodiments, the method of the present invention is for inhibiting or disrupting biofilm formation on an object, or for reducing biofilm attached to said object, and comprises coating of said object with said compound or a composition comprising it, or immersing of said object within a composition comprising said compound, respectively.

In yet another aspect, the present invention relates to a pharmaceutical composition for inhibiting or disrupting biofilm, e.g., bacterial or fungal biofilm, formation, or reducing biofilm, said composition comprising a pharmaceutically acceptable carrier, and a compound of the formula I wherein X is a pharmaceutically acceptable anion, including the compounds excluded by the proviso above.

In still another aspect, the present invention relates to a compound of the formula I, including the compounds excluded by the proviso above, for use in inhibiting or disrupting biofilm, e.g., bacterial or fungal biofilm, formation, or reducing biofilm.

In yet a further aspect, the present invention relates to a method for inhibiting or disrupting biofilm formation, or reducing biofilm, in an individual in need thereof, comprising administering to said individual a therapeutically effective amount of a compound of the formula I, including the compounds excluded by the proviso above.

DETAILED DESCRIPTION

Figure 1:
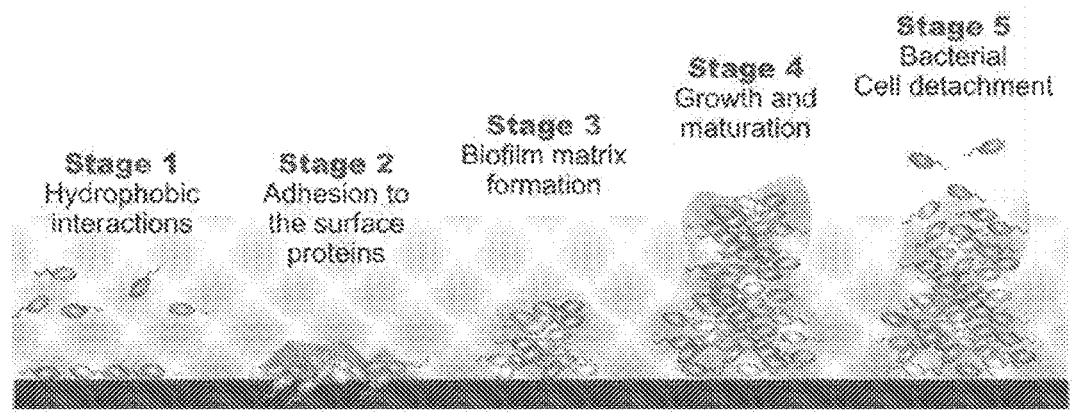
FIG. 1 illustrates the stages of biofilm formation process.

The present invention relates to cationic amphiphilic systems capable of interfering with the chemical interactions between different components of biofilm matrices, more particularly bacterial biofilm matrices, thereby inhibiting or preventing biofilm formation and facilitating existing biofilm decomposition without intervening with bacterial viability and damaging mammalian cell membranes as many families of cationic amphiphiles do.

More specifically, the invention provides cationic pillararene derivatives such as positively charged poly-ammonium, poly-phosphonium and poly-imidazolium pillararene derivatives. These systems are water soluble organic salts containing both a lipophilic but relatively electron-rich cavity as well as two arrays of positively charged moieties of the two opposite faces of the pillararene backbone which can interact with the negatively charged membranes and other different molecular components of the biofilm matrices. The cationic ammonium/phosphonium pillar[5-6]arenes exemplified herein, including both known and novel compounds, were synthesized according to the procedures described in detail in the Experimental Section and depicted in Schemes 1-3 hereinafter, and are shown in Scheme 4.

The novel cationic pillar[5-6]arene derivatives specifically disclosed herein are compounds of the formula I, wherein (i) n is 5; $R_1$ is —$CH_2$—; $R_2$ and $R_3$ are H; $R_4$ and $R_5$ are —$(CH_2)_3$—; and Y is —$N^+(CH_3)_3$ or —$P^+(CH_3)_3$, herein identified compound 25 and 29, respectively; (ii) n is 5; $R_1$ is —$CH_2$—; $R_2$ and $R_3$ are H; $R_4$ and $R_5$ are —$(CH_2)_3$—; and Y is —$N^+(C_2H_5)_3$ or —$P^+(C_2H_5)_3$, herein identified compound 28 and 30, respectively; (iii) n is 5; $R_1$ is —$CH_2$—; $R_2$ and $R_3$ are H; $R_4$ and $R_5$ are —$(CH_2)_6$—, and Y is —$N^+(CH_3)_3$, herein identified compound 31; or (iv) n is 6; $R_1$ is —$CH_2$—; $R_2$ and $R_3$ are H; $R_4$ and $R_5$ are —$(CH_2)_3$—, and Y is —$N^+(CH_3)_3$, herein identified compound 32. Additional cationic pillar[5-6]arene derivatives specifically exemplified are compounds of the formula I, wherein (i) n is 5; $R_1$ is —$CH_2$—; $R_2$ and $R_3$ are H; $R_4$ and $R_5$ are —$(CH_2)_2$—; and Y is —$N^+(CH_3)_3$, —$N^+(C_2H_5)_3$, or 1-methyl-imidazolium-3-yl, herein identified compound 21 (or 26), 23 and 22, respectively; or (ii) n is 6; $R_1$ is —$CH_2$—; $R_2$ and $R_3$ are H; $R_4$ and $R_5$ are —$(CH_2)_2$—, and Y is —$N^+(CH_3)_3$, or 1-methyl-imidazolium-3-yl, herein identified compound 27 and 33, respectively. In all those compounds, X is Br⁻ or Cl⁻.

As has been found and shown herein, the water soluble cationic pillar[5-6]arene derivatives tested are extremely efficient in inhibiting biofilm formation at sub µM concentrations, without affecting the tested bacterial cell viability or causing measurable damage to the membranes of mammalian red blood cells (RBCs). The phosphonium-decorated pillararenes exhibited similar potencies as inhibitors of biofilm formation as their corresponding ammonium analogues, demonstrating that the number of positively charged groups and not their chemical identity are key to their anti-biofilm activity. The pillarene platform appears to be important and positive charges operating cooperatively are needed for effective anti-biofilm activity, as indicated by our finding that the respective cationic monomers were completely inactive. Interestingly, the cationic pillararene derivatives tested retained their anti-biofilm capability even after four hours of exposure to acidic or alkaline pH. The organisms in which the compounds were found to inhibit biofilm formation include clinical pathogens such as *Methicillin-resistant Staphylococcus aureus* (MRSA), *Pseudomonas aeruginosa* and more.

Such cationic pillararene derivatives can thus be used to fight biofilm formation and to eradicate existing biofilms in myriad of applications such as in water reservoirs, closed circuit water systems, in painting industries especially in dyes used to protect vessels from water, in toothpaste and dentistry industry, and more. The compounds may also be used to fight biofilm on surfaces in hospitals, medical devices and implants, as well as in external and internal pads and optionally in conjunction with antibiotic treatments.

In one aspect, the present invention thus provides a compound of the formula I:

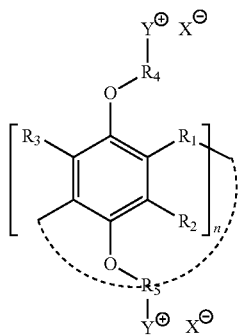

I wherein
$R_1$ is —$CR_6R_7$—, wherein $R_6$ and $R_7$ each independently is H, halogen, —$COR_8$, —$COOR_8$, —$OCOOR_8$, —$OCON(R_8)_2$, —CN, —$NO_2$, —$SR_8$, —$OR_8$, —$N(R_8)_2$, —$CON(R_8)_2$, —$SO_2R_8$, —$SO_3H$, —S(=O)$R_8$, or ($C_1$-$C_8$)alkyl optionally substituted by one or more groups each independently selected from —$COR_8$, —$COOR_8$, —$OCOOR_8$, —$OCON(R_8)_2$, —CN, —$NO_2$, —$SR_8$, —$OR_8$, —$N(R_8)_2$, —$CON(R_8)_2$, —$SO_2R_8$, —$SO_3H$, —S(=O)$R_8$, —$N^+(R')_3$ or —$P^+(R')_3$, wherein R' each independently is H, ($C_1$-$C_6$)alkyl, phenyl, benzyl, or heterocyclyl, or two R's together with the N atom to which they are attached form a 3-7 membered saturated ring, optionally containing one or more heteroatoms selected from O, S or N and optionally further substituted at the additional N atom;

$R_2$ and $R_3$ each independently is H, halogen, or ($C_1$-$C_8$)alkyl optionally substituted by one or more groups each independently selected from halogen, —$COR_8$, —$COOR_8$, —$OCOOR_8$, —$OCON(R_8)_2$, —CN, —$NO_2$, —$SR_8$, —$OR_8$, —$N(R_8)_2$, —$CON(R_8)_2$, —$SO_2R_8$, —$SO_3H$, —S(=O)$R_8$, —$N^+(R')_3$ or —$P^+(R')_3$, wherein R' each independently is H, ($C_1$-$C_6$)alkyl, phenyl, benzyl, or heterocyclyl, or two R's together with the N atom to which they are attached form a 3-7 membered saturated ring, optionally containing one or more heteroatoms selected from O, S or N and optionally further substituted at the additional N atom;

$R_4$ and $R_5$ each independently is selected from ($C_1$-$C_{10}$) alkylene, ($C_2$-$C_{10}$)alkenylene, or ($C_2$-$C_{10}$)alkynylene, optionally substituted by one or more groups each independently selected from halogen, —$COR_8$, —$COOR_8$, —$OCOOR_8$, —$OCON(R_8)_2$, —CN, —$NO_2$, —$SR_8$, —$OR_8$, —$N(R_8)_2$, —$CON(R_8)_2$, —$SO_2R_8$, —$SO_3H$, —S(=O)$R_8$, ($C_6$-$C_{10}$)aryl, ($C_1$-$C_4$)alkylene-($C_6$-$C_{10}$)aryl, heteroaryl, or ($C_1$-$C_4$)alkylene-heteroaryl, and further optionally interrupted by one or more identical or different heteroatoms selected from S, O or N, and/or at least one group each independently selected from —NH—CO—, —CO—NH—, —N($C_1$-$C_8$alkyl)-, —N($C_6$-$C_{10}$aryl)-, ($C_6$-$C_{10}$)arylenediyl, or heteroarylenediyl;

$R_8$ each independently is H or ($C_1$-$C_8$)alkyl;

Y each independently is (i) a cation derived from a nitrogen-containing group and selected from an ammonium [—$N^+(R')_3$], hydrazinium [—$N^+(R')_2$—$N(R')_2$], ammoniumoxy [—$N^+(R')_2$→O], iminium [—$N^+(R')_2$=C<], amidinium [—$N^+(R')_2$—C(R')=NR'], or guanidinium [—$N^+(R')_2$—C(=NR')—$N(R')_2$]; (ii) a cation derived from a nitrogen-containing mono- or polycyclic heteroaromatic group and selected from pyrazolium, imidazolium, oxazolium, thiazolium, pyridinium, pyrimidinium, quinolinium, isoquinolinium, 1,2,4-triazinium, 1,3,5-triazinium, or purinium, optionally substituted by one or more groups each independently selected from halogen, ($C_1$-$C_6$)alkyl, —COH, —COOH, —OCOOH, —$OCONH_2$, —CN, —$NO_2$, —SH, —OH, —$NH_2$, —$CONH_2$, —$SO_3H$, —$SO_2H$, or —S(=O)H; or (iii) a cation derived from an onium group not containing nitrogen and selected from phosphonium [—$P^+(R')_3$], arsonium [—$As^+(R')_3$], oxonium [—$O^+(R')_2$], sulfonium [—$S^+(R')_2$], selenonium [—$Se^+(R')_2$], telluronium [—$Te^+(R')_2$], stibonium [—$Sb^+(R')_3$], or bismuthonium [—$Bi^+(R')_3$], wherein R' each independently is H, ($C_1$-$C_6$) alkyl, phenyl, benzyl, or heterocyclyl, or two R's in the ammonium, hydrazinium, ammoniumoxy, iminium, amidinium or guanidinium groups, together with the N atom to which they are attached, form a 3-7 membered saturated ring, optionally containing one or more heteroatoms selected from O, S or N and optionally further substituted at the additional N atom;

X is a counter anion such as $Br^-$, $Cl^-$, $F^-$, $I^-$, $PF_6^-$, $BF_4^-$, $OH^-$, $ClO_4^-$, $HSO_4^-$, $CF_3COO^-$, $CN^-$, alkyl$COO^-$, aryl$COO^-$, a pharmaceutically acceptable anion, or a combination thereof; and n is an integer of 5-11,
but excluding the compounds wherein $R_1$ is —$CH_2$—; $R_2$ and $R_3$ are H; and: (i) n is 5; $R_4$ and $R_5$ are —($CH_2$)$_2$—; and Y is 1-methyl-imidazolium-3-yl or —$N^+(CH_3)_3$; (ii) n is 5; $R_4$ and $R_5$ are —($CH_2$)$_3$—; and Y is —$P^+(C_4H_9)_3$; (iii) n is 5; $R_4$ and $R_5$ are —($CH_2$)$_4$—; and Y is —$N^+(CH_3)_3$; (iv) n is 6; $R_4$ and $R_5$ are —($CH_2$)$_2$—; and Y is —$N^+(CH_3)_3$; (v) n is 6; $R_4$ and $R_5$ are —($CH_2$)$_4$—; and Y is —$N^+(CH_3)_3$; (vi) n is 6; $R_4$ and $R_5$ are —($CH_2$)$_4$—; and Y is 1-pyridinium; or (vii) n is 6; $R_4$ and $R_5$ are —($CH_2$)$_2$—; and Y is 1-methyl-imidazolium-3-yl.

The term "halogen" as used herein refers to a halogen and includes fluoro, chloro, bromo, and iodo, and it is preferably chloro or bromo.

The term "alkyl" as used herein typically means a linear or branched saturated hydrocarbon radical having 1-8 carbon atoms and includes, e.g., methyl, ethyl, n-propyl, isopropyl, n-butyl, sec-butyl, isobutyl, tert-butyl, n-pentyl, isoamyl, 2,2-dimethylpropyl, n-hexyl, n-heptyl, n-octyl, and the like. Preferred are ($C_1$-$C_6$)alkyl groups, more preferably ($C_1$-$C_4$)alkyl groups, most preferably methyl, ethyl or propyl. The alkyl defined herein may optionally be substituted with one or more groups each independently selected from halogen, —COR, —COOR, —OCOOR, —OCON(R)$_2$, —CN, —NO$_2$, —SR, —OR, —N(R)$_2$, —CON(R)$_2$, —SO$_2$R, —SO$_3$R or —S(=O)R, wherein R is H or unsubstituted (C$_1$-C$_8$)alkyl.

The term "alkylene" as used herein typically means a straight or branched divalent hydrocarbon radical having 1-10 carbon atoms, e.g., methylene, ethylene, propylene, butylene, 2-methylpropylene, pentylene, 2-methylbutylene, hexylene, 2-methylpentylene, 3-methylpentylene, 2,3-dimethylbutylene, heptylene, octylene, nonylene, decanylene, and the like. Preferred are (C$_1$-C$_8$)alkylene or (C$_1$-C$_6$)alkylene, more preferably (C$_1$-C$_4$)alkylene, most preferably methylene, ethylene, propylene, or butylene. The terms "alkenylene" and "alkynylene" typically mean straight or branched divalent hydrocarbon radicals having 2-10 carbon atoms, and one or more double or triple bonds, respectively.

The term "aryl" denotes an aromatic carbocyclic group having 6-10 carbon atoms consisting of a single ring or condensed multiple rings such as, but not limited to, phenyl and naphthyl. The aryl defined herein may optionally be substituted with one or more groups each independently selected from halogen, —COR, —COOR, —OCOOR, —OCON(R)$_2$, —CN, —NO$_2$, —SR, —OR, —N(R)$_2$, —CON(R)$_2$, —SO$_2$R, —SO$_3$R, —S(=O)R, or —(C$_1$-C$_8$) alkyl, wherein R is H or unsubstituted (C$_1$-C$_8$)alkyl. The term "arylenediyl" refers to a divalent radical derived from an "aryl" as defined herein by removal of a further hydrogen atom from any of the ring atoms.

The term "heterocyclic ring" denotes a mono- or polycyclic non-aromatic ring of 4-12 atoms containing at least one carbon atom and one to three heteroatoms selected from sulfur, oxygen or nitrogen, which may be saturated or unsaturated, i.e., containing at least one unsaturated bond. Preferred are 3- or 7-membered heterocyclic rings. The term "heterocyclyl" as used herein refers to any univalent radical derived from a heterocyclic ring as defined herein by removal of hydrogen from any ring atom. Examples of such radicals include, without limitation, piperidino, 4-morpholinyl, or pyrrolidinyl. The heterocyclyl defined herein may optionally be substituted, at any position of the ring, with one or more groups each independently selected from halogen, —COR, —COOR, —OCOOR, —OCON(R)$_2$, —CN, —NO$_2$, —SR, —OR, —N(R)$_2$, —CON(R)$_2$, —SO$_2$R, —SO$_3$R, —S(=O)R, or —(C$_1$-C$_8$)alkyl, wherein R is H or unsubstituted (C$_1$-C$_8$)alkyl.

The term "heteroaryl" refers to a radical derived from a 5-10-membered mono- or poly-cyclic heteroaromatic ring containing 1-3, preferably 1-2, heteroatoms selected from nitrogen, sulfur or oxygen. Examples of mono-cyclic heteroaryls include, without being limited to, pyrrolyl, furyl, thienyl, thiazinyl, pyrazolyl, pyrazinyl, imidazolyl, oxazolyl, isoxazolyl, thiazolyl, isothiazolyl, pyridyl, pyrimidinyl, 1,2,3-triazinyl, 1,3,4-triazinyl, and 1,3,5-triazinyl. Polycyclic heteroaryl radicals are preferably composed of two rings such as, but not limited to, benzofuryl, isobenzofuryl, benzothienyl, indolyl, quinolinyl, isoquinolinyl, imidazo[1,2-a]pyridyl, benzimidazolyl, benzthiazolyl, benzoxazolyl, pyrido[1,2-a]pyrimidinyl and 1,3-benzodioxinyl. The heteroaryl may optionally be substituted by one or more groups each independently selected from halogen, —COR, —COOR, —OCOOR, —OCON(R)$_2$, —CN, —NO$_2$, —SR, —OR, —N(R)$_2$, —CON(R)$_2$, —SO$_2$R, —SO$_3$R, —S(=O) R, or —(C$_1$-C$_8$)alkyl, wherein R is H or unsubstituted (C$_1$-C$_8$)alkyl. It is to be understood that when a polycyclic heteroaryl is substituted, the substitution may be in any of the carbocyclic and/or heterocyclic rings. The term "heteroarylenediyl" denotes a divalent radical derived from a "heteroaryl" as defined herein by removal of a further hydrogen atom from any of the ring atoms.

The term "cation derived from a nitrogen-containing group" as used herein denotes for example, but without limiting to, an ammonium [—N$^+$(R')$_3$], hydrazinium [—N$^+$(R')$_2$—N(R')$_2$], ammoniumoxy [—N$^+$(R')$_2$→O], iminium [—N$^+$(R')$_2$=C<], amidinium [—N$^+$(R')$_2$—C(R')=NR'], or guanidinium [—N$^+$(R')$_2$—C(=NR')—N(R')$_2$], wherein R' each independently is H, (C$_1$-C$_6$)alkyl, phenyl, benzyl, or heterocyclyl, or two R's together with the N atom to which they are attached form a 3-7 membered saturated ring, optionally containing one or more heteroatoms selected from O, S or N and optionally further substituted at the additional N atom. In particular embodiments, the cation derived from a nitrogen-containing group is an ammonium as defined hereinabove.

The term "cation derived from a nitrogen-containing mono- or polycyclic heteroaromatic group optionally containing O, S or additional N atoms" as used herein denotes for example, but without limiting to, pyrazolium, imidazolium, oxazolium, thiazolium, pyridinium, pyrimidinium, quinolinium, isoquinolinium, 1,2,4-triazinium, 1,3,5-triazinium, or purinium, optionally substituted by one or more groups each independently selected from halogen, (C$_1$-C$_6$) alkyl, —COH, —COOH, —OCOOH, —OCONH$_2$, —CN, —NO$_2$, —SH, —OH, —NH$_2$, —CONH$_2$, —SO$_3$H, —SO$_2$H, or —S(=O)H;

The term "cation derived from an onium group not containing nitrogen" as used herein denotes for example, but without limiting, phosphonium [—P$^+$(R')$_3$], arsonium [—As$^+$(R')$_3$], oxonium [—O$^+$(R')$_2$], sulfonium [—S$^+$(R')$_2$], selenonium [—Se$^+$(R')$_2$], telluronium [—Te$^+$(R')$_2$], stibonium [—Sb$^+$(R')$_3$], or bismuthonium [—Bi$^+$(R')$_3$], wherein R' each independently is H, (C$_1$-C$_6$)alkyl, phenyl, benzyl, or heterocyclyl. In particular embodiments, the cation derived from an onium group not containing nitrogen is a phosphonium as defined hereinabove.

In certain embodiments, the compound of the present invention is a compound of the formula I, wherein R$_1$ is —CR$_6$R$_7$—, wherein R$_6$ and R$_7$ each independently is H, halogen, —COH, —COOH, —OCOOH, —OCONH$_2$, —CN, —NO$_2$, —SH, —OH, —NH$_2$, —CONH$_2$, —SO$_3$H, —SO$_2$H, —S(=O)H, or (C$_1$-C$_8$)alkyl optionally substituted by one or more groups each independently selected from —COH, —COOH, —OCOOH, —OCONH$_2$, —CN, —NO$_2$, —SH, —OH, —NH$_2$, —CONH$_2$, —SO$_3$H, —SO$_2$H, —S(=O)H, —N$^+$(R')$_3$ or —P$^+$(R')$_3$, wherein R' each independently is H, (C$_1$-C$_4$)alkyl, phenyl, or benzyl. Particular such compounds are those wherein R$_6$ and R$_7$ each independently is (C$_1$-C$_8$)alkyl, preferably (C$_1$-C$_4$)alkyl, or H. In preferred embodiments, R$_1$ is —CH$_2$—, i.e., R$_6$ and R$_7$ are each H.

In certain embodiments, the compound of the present invention is a compound of the formula I, wherein R$_2$ and R$_3$ each independently is H, or (C$_1$-C$_4$)alkyl, preferably (C$_1$-C$_2$)alkyl, optionally substituted by one or more groups each independently selected from halogen, —COH, —COOH, —OCOOH, —OCONH$_2$, —CN, —NO$_2$, —SH, —OH, —NH$_2$, —CONH$_2$, —SO$_3$H, —SO$_2$H, —S(=O)H, —N$^+$(R')$_3$ or —P$^+$(R')$_3$, wherein R' each independently is H, (C$_1$-C$_4$)alkyl, phenyl, or benzyl. Particular such compounds are those wherein R$_2$ and R$_3$ each independently is (C$_1$-C$_4$) alkyl, preferably (C$_1$-C$_2$)alkyl, or H. In preferred embodiments, R$_2$ and R$_3$ are each H.

In certain embodiments, the compound of the present invention is a compound of the formula I, wherein R$_4$ and R$_5$ each independently is (C$_2$-C$_{10}$)alkylene optionally substituted and further optionally interrupted as defined above. In particular such embodiments, $R_4$ and $R_5$ each independently is $(C_2\text{-}C_{10})$alkylene, $(C_2\text{-}C_8)$alkylene or $(C_2\text{-}C_6)$alkylene, optionally substituted by one or more groups each independently selected from halogen, —COH, —COOH, —OCOOH, —OCONH$_2$, —CN, —NO$_2$, —SH, —OH, —NH$_2$, —CONH$_2$, —SO$_3$H, —SO$_2$H, —S(=O)H, $(C_6)$aryl, $(C_1\text{-}C_4)$alkylene-$(C_6)$aryl, heteroaryl, or $(C_1\text{-}C_4)$alkylene-heteroaryl, and further optionally interrupted by one or more identical or different heteroatoms selected from S, O or N, and/or at least one group each independently selected from —NH—CO—, —CO—NH—, —N($C_1$-$C_8$alkyl)-, —N($C_6$aryl)-, $(C_6)$arylenediyl, or heteroarylenediyl. More particular such compounds are those wherein $R_4$ and $R_5$ each independently is $(C_2\text{-}C_{10})$alkylene, $(C_2\text{-}C_8)$alkylene or $(C_2\text{-}C_6)$alkylene, optionally interrupted by one or more identical or different heteroatoms, preferably one or more O atoms.

In certain embodiments, the compound of the present invention is a compound of the formula I, wherein $R_4$ and $R_5$ are identical.

In certain embodiments, the compound of the present invention is a compound of the formula I, wherein Y each independently is (i) ammonium [—N$^+$(R')$_3$] or phosphonium [—P$^+$(R')$_3$], wherein R' each independently is H, $(C_1\text{-}C_6)$alkyl, phenyl, benzyl, or heterocyclyl; or (ii) imidazolium, optionally substituted by one or more groups each independently selected from halogen, $(C_1\text{-}C_6)$alkyl, —COH, —COOH, —OCOOH, —OCONH$_2$, —CN, —NO$_2$, —SH, —OH, —NH$_2$, —CONH$_2$, —SO$_3$H, —SO$_2$H, or —S(=O)H. Particular such compounds are those wherein Y each independently is ammonium [—N$^+$(R')$_3$] or phosphonium [—P$^+$(R')$_3$], wherein R' each independently is H, methyl, ethyl, or propyl; or 1-methyl-imidazolium-3-yl.

In certain embodiments, the compound of the present invention is a compound of the formula I, wherein n is an integer of 5, 6, 7 or 8, preferably 5 or 6.

In certain embodiments, the compound of the present invention is a compound of the formula I, wherein (i) $R_1$ is —CR$_6$R$_7$—, wherein $R_6$ and $R_7$ each independently is H, halogen, —COH, —COOH, —OCOOH, —OCONH$_2$, —CN, —NO$_2$, —SH, —OH, —NH$_2$, —CONH$_2$, —SO$_3$H, —SO$_2$H, —S(=O)H, or $(C_1\text{-}C_8)$alkyl optionally substituted by one or more groups each independently selected from —COH, —COOH, —OCOOH, —OCONH$_2$, —CN, —NO$_2$, —SH, —OH, —NH$_2$, —CONH$_2$, —SO$_3$H, —SO$_2$H, —S(=O)H, —N$^+$(R')$_3$ or —P$^+$(R')$_3$, wherein R' each independently is H, $(C_1\text{-}C_4)$alkyl, phenyl, or benzyl; (ii) $R_2$ and $R_3$ each independently is H, or $(C_1\text{-}C_4)$alkyl, preferably $(C_1\text{-}C_2)$alkyl, optionally substituted by one or more groups each independently selected from halogen, —COH, —COOH, —OCOOH, —OCONH$_2$, —CN, —NO$_2$, —SH, —OH, —NH$_2$, —CONH$_2$, —SO$_3$H, —SO$_2$H, —S(=O)H, —N$^+$(R')$_3$ or —P$^+$(R')$_3$, wherein R' each independently is H, $(C_1\text{-}C_4)$alkyl, phenyl, or benzyl; (iii) $R_4$ and $R_5$ each independently is $(C_2\text{-}C_{10})$alkylene, $(C_2\text{-}C_8)$alkylene or $(C_2\text{-}C_6)$alkylene, optionally substituted by one or more groups each independently selected from halogen, —COH, —COOH, —OCOOH, —OCONH$_2$, —CN, —NO$_2$, —SH, —OH, —NH$_2$, —CONH$_2$, —SO$_3$H, —SO$_2$H, —S(=O)H, $(C_6)$aryl, $(C_1\text{-}C_4)$alkylene-$(C_6)$aryl, heteroaryl, or $(C_1\text{-}C_4)$alkylene-heteroaryl, and further optionally interrupted by one or more identical or different heteroatoms selected from S, O or N, and/or at least one group each independently selected from —NH—CO—, —CO—NH—, —N($C_1$-$C_8$alkyl)-, —N($C_6$aryl)-, $(C_6)$arylenediyl, or heteroarylenediyl; and (iv) n is an integer of 5, 6, 7 or 8.

In particular such embodiments, the compound of the invention is a compound of the formula I, wherein $R_1$ is —CH$_2$—; $R_2$ and $R_3$ are H; and $R_4$ and $R_5$ each independently is $(C_2\text{-}C_{10})$alkylene, $(C_2\text{-}C_8)$alkylene or $(C_2\text{-}C_6)$alkylene, optionally interrupted by one or more O atoms. More particular such compounds are those wherein Y each independently is (i) ammonium [—N$^+$(R')$_3$] or phosphonium [—P$^+$(R')$_3$], wherein R' each independently is H, $(C_1\text{-}C_6)$alkyl, phenyl, benzyl, or heterocyclyl, but preferably H, methyl, ethyl or propyl; or (ii) imidazolium, optionally substituted by one or more groups each independently selected from halogen, $(C_1\text{-}C_6)$alkyl, —COH, —COOH, —OCOOH, —OCONH$_2$, —CN, —NO$_2$, —SH, —OH, —NH$_2$, —CONH$_2$, —SO$_3$H, —SO$_2$H, or —S(=O)H, but preferably 1-methyl-imidazolium-3-yl. In preferred such embodiments, n is an integer of 5 or 6.

Specific cationic pillararenes according to the present invention, including those exemplified herein, are the compounds of the formula I, wherein $R_1$ is —CH$_2$—; $R_2$ and $R_3$ are H; X is a counter anion as defined above; and: (i) $R_4$ and $R_5$ are —(CH$_2$)$_3$—, or —(CH$_2$)$_6$—; Y is —N$^+$(CH$_3$)$_3$, —N$^+$(C$_2$H$_5$)$_3$, —P$^+$(CH$_3$)$_3$, or —P$^+$(C$_2$H$_5$)$_3$; and n is 5; or (ii) $R_4$ and $R_5$ are —(CH$_2$)$_3$—; Y is —N$^+$(CH$_3$)$_3$, —P$^+$(CH$_3$)$_3$, or 1-methyl-imidazolium-3-yl; and n is 6.

The cationic pillararenes of the invention, also referred to herein as "biofilm inhibitors", can be prepared by any suitable procedure and technology known in the art, e.g., as exemplified herein and depicted in detail in Schemes 1-3.

In another aspect, the present invention provides a composition comprising a carrier and a compound of the formula I as defined in any one of the embodiments above, but excluding the compounds wherein $R_1$ is —CH$_2$—; $R_2$ and $R_3$ are H; and: (i) n is 5; $R_4$ and $R_5$ are —(CH$_2$)$_2$—; and Y is 1-methyl-imidazolium-3-yl or —N$^+$(CH$_3$)$_3$; (ii) n is 5; $R_4$ and $R_5$ are —(CH$_2$)$_3$—; and Y is —P$^+$(C$_4$H$_9$)$_3$; (iii) n is 5; $R_4$ and $R_5$ are —(CH$_2$)$_4$—; and Y is —N$^+$(CH$_3$)$_3$; (iv) n is 6; $R_4$ and $R_5$ are —(CH$_2$)$_2$—; and Y is —N$^+$(CH$_3$)$_3$; (v) n is 6; $R_4$ and $R_5$ are —(CH$_2$)$_4$—; and Y is —N$^+$(CH$_3$)$_3$; (vi) n is 6; $R_4$ and $R_5$ are —(CH$_2$)$_4$—; and Y is 1-pyridinium; or (vii) n is 6; $R_4$ and $R_5$ are —(CH$_2$)$_2$—; and Y is 1-methyl-imidazolium-3-yl. Such compositions may be inter alia pharmaceutical compositions, wherein said carrier is a pharmaceutically acceptable carrier, and the counter anion X is a pharmaceutically acceptable anion.

In certain embodiments, the composition of the present invention comprises a compound selected from those specifically disclosed herein, i.e., a compound of the formula I, wherein $R_1$ is —CH$_2$—; $R_2$ and $R_3$ are H; X is a counter anion as defined above; and: (i) $R_4$ and $R_5$ are —(CH$_2$)$_3$—, or —(CH$_2$)$_6$—; Y is —N$^+$(CH$_3$)$_3$, —N$^+$(C$_2$H$_5$)$_3$, —P$^+$(CH$_3$)$_3$, or —P$^+$(C$_2$H$_5$)$_3$; and n is 5; or (ii) $R_4$ and $R_5$ are —(CH$_2$)$_3$—; Y is —N$^+$(CH$_3$)$_3$, —P$^+$(CH$_3$)$_3$, or 1-methyl-imidazolium-3-yl; and n is 6.

In a further aspect, the present invention relates to a method for inhibiting or disrupting biofilm formation in an aqueous media or on an object, or for reducing biofilm existing in an aqueous media or attached to an object, said method comprising contacting said aqueous media or object with a compound of the formula I as defined in any one of the embodiments above, including the compounds wherein $R_1$ is —CH$_2$—; $R_2$ and $R_3$ are H; and: (i) n is 5; $R_4$ and $R_5$ are —(CH$_2$)$_2$—; and Y is 1-methyl-imidazolium-3-yl or —N$^+$(CH$_3$)$_3$; (ii) n is 5; $R_4$ and $R_5$ are —(CH$_2$)$_3$—; and Y is —P$^+$(C$_4$H$_9$)$_3$; (iii) n is 5; $R_4$ and $R_5$ are —(CH$_2$)$_4$—; and Y is —N⁺(CH₃)₃; (iv) n is 6; R₄ and R₅ are —(CH₂)₂—; and Y is —N⁺(CH₃)₃; (v) n is 6; R₄ and R₅ are —(CH₂)₄—; and Y is —N⁺(CH₃)₃; (vi) n is 6; R₄ and R₅ are —(CH₂)₄—; and Y is 1-pyridinium; or (vii) n is 6; R₄ and R₅ are —(CH₂)₂—; and Y is 1-methyl-imidazolium-3-yl.

In specific embodiments, the method of the present invention comprises contacting said aqueous media or object with a compound of the formula I, wherein R₁ is —CH₂—; R₂ and R₃ are H; R₄ and R₅ are identical and each one is —(CH₂)₂₋₁₀—, i.e., —(CH₂)₂, —(CH₂)₃, —(CH₂)₄, —(CH₂)₅, —(CH₂)₆, —(CH₂)₇, —(CH₂)₈, —(CH₂)₉, or —(CH₂)₁₀; Y is —N⁺(CH₃)₃, —N⁺(C₂H₅)₃, —P⁺(CH₃)₃, —P⁺(C₂H₅)₃, or 1-methyl-imidazolium-3-yl; n is 5 or 6; and X is a counter anion, wherein each one of the combinations of R₁-R₅, Y, n, and X defined herein represents a specific such compound.

In certain embodiments, the method of the present invention is for inhibiting or disrupting biofilm formation in an aqueous media, i.e., a medium having water in it, or for reducing biofilm existing in said aqueous media, wherein said contacting comprises dissolving a compound of the formula I, or a composition comprising it, within said aqueous media.

In certain embodiments, the method of the present invention is for inhibiting or disrupting biofilm formation on an object, or for reducing biofilm attached to said object, wherein said contacting comprises coating said object with a compound of the formula I, or a composition comprising it, or immersing said object within a composition comprising said compound, respectively. The object being "treated" according to the method of the present invention may be, without being limited to, an object designed for functioning in water, e.g., the hull of a boat, a pipe, a filter, a pump, or a heat-exchanger; a medical implant such as a stent; a medical device such as a catheter; or a biomedical pad such as an adhesive bandage. In particular such embodiments, the method of the present invention comprises coating said object with a composition comprising a compound of the formula I, i.e., with an antifouling composition such as antifouling paints and coatings for use inter alia in the food industry and hospitals. Such paints and coatings may be formulated, e.g., as sprays or hydrogels.

In certain embodiments, the method of the present invention as defined in any one of the embodiments above results in increased sensitivity of said aqueous media or object to a bacteriocide, i.e., a substance that kills bacteria such as a disinfectant (an antimicrobial agent that is applied to non-living objects to destroy microorganisms that are living on the objects), antiseptic, or antibiotic, and optionally further comprises contacting said aqueous media or object with said bacteriocide. According to the present invention, the aqueous media or object "treated" by the method of the invention can be contacted with said compound of the formula I and said bacteriocide either at the same time (i.e., contacted with a combination of said compound of the formula I and said bacteriocide) or sequentially at any order.

In yet another aspect, the present invention relates to a pharmaceutical composition for inhibiting or disrupting biofilm, e.g., bacterial or fungal biofilm, formation, or reducing biofilm, said composition comprising a pharmaceutically acceptable carrier, and a compound of the formula I as defined in any one of the embodiments above, including the compounds wherein R₁ is —CH₂—, R₂ and R₃ are H; and: (i) n is 5; R₄ and R₅ are —(CH₂)₂—; and Y is 1-methyl-imidazolium-3-yl or —N⁺(CH₃)₃; (ii) n is 5; R₄ and R₅ are —(CH₂)₃—; and Y is —P⁺(C₄H₉)₃; (iii) n is 5; R₄ and R₅ are —(CH₂)₄—; and Y is —N⁺(CH₃)₃; (iv) n is 6; R₄ and R₅ are —(CH₂)₂—; and Y is —N⁺(CH₃)₃; (v) n is 6; R₄ and R₅ are —(CH₂)₄—; and Y is —N⁺(CH₃)₃; (vi) n is 6; R₄ and R₅ are —(CH₂)₄—; and Y is 1-pyridinium; or (vii) n is 6; R₄ and R₅ are —(CH₂)₂—; and Y is 1-methyl-imidazolium-3-yl, wherein X is a pharmaceutically acceptable anion, i.e., an anion capable of forming a pharmaceutically acceptable salt of said compound.

Pharmaceutically acceptable anions include, without limiting, chloride, bromide, iodide, acetate, mesylate, esylate, maleate, fumarate, tartrate, bitartrate, sulfate, p-toluene-sulfonate, benzenesulfonate, methanesulfonate, ethanedisulfonate (edisylate), ethanesulfonate (esylate), tosylate, benzoate, acetate, phosphate, carbonate, bicarbonate, succinate, and citrate. Multiple anions can be used in a single preparation if desired.

In specific embodiments, the pharmaceutical composition of the present invention comprises a compound of the formula I, wherein R₁ is —CH₂—; R₂ and R₃ are H; R₄ and R₅ are identical and each one is —(CH₂)₂₋₁₀—, i.e., —(CH₂)₂, —(CH₂)₃, —(CH₂)₄, —(CH₂)₅, —(CH₂)₆, —(CH₂)₇, —(CH₂)₈, —(CH₂)₉, or —(CH₂)₁₁); Y is —N⁺(CH₃)₃, —N⁺(C₂H₅)₃, —P⁺(CH₃)₃, —P⁺(C₂H₅)₃, or 1-methyl-imidazolium-3-yl; n is 5 or 6; and X is a pharmaceutically acceptable anion, wherein each one of the combinations of R₁-R₅, Y, n, and X defined herein represents a specific such compound.

The pharmaceutical compositions provided by the present invention may be prepared by conventional techniques, e.g., as described in Remington: The Science and Practice of Pharmacy, 19$^{th}$ Ed., 1995. The compositions can be prepared, e.g., by uniformly and intimately bringing the active agent, i.e., the compound of the formula I, into association with a liquid carrier, a finely divided solid carrier, or both, and then, if necessary, shaping the product into the desired formulation. The compositions may be in liquid, solid or semisolid form and may further include pharmaceutically acceptable fillers, carriers, diluents or adjuvants, and other inert ingredients and excipients. In one embodiment, the pharmaceutical composition of the present invention is formulated as nanoparticles.

The pharmaceutical compositions can be formulated for any suitable route of administration, e.g., for parenteral administration such as intravenous, intraarterial, intrathecal, intrapleural, intratracheal, intraperitoneal, intramuscular or subcutaneous administration, topical administration, oral or enteral administration, or for inhalation. In certain embodiments, these compositions are formulated for either topical administration or for inhalation.

The pharmaceutical composition of the invention may be in the form of a sterile injectable aqueous or oleaginous suspension, which may be formulated according to the known art using suitable dispersing, wetting or suspending agents. The sterile injectable preparation may also be a sterile injectable solution or suspension in a non-toxic parenterally acceptable diluent or solvent. Acceptable vehicles and solvents that may be employed include, without limiting, water, Ringer's solution and isotonic sodium chloride solution.

The term "topical administration" as used herein refers to external application to, e.g., the skin, scalp, mucous membranes, teeth, and hair. Pharmaceutical compositions for topical administration may thus be in the form of an aqueous solution, a gel, a cream, a paste, a lotion, a spray, a suspension, a powder, a dispersion, a salve, an ointment, a serum, an anhydrous stick, oil based sprays, oil-in-water emulsions or water-in-oil emulsions. In certain particular embodiments, the pharmaceutical composition of the invention is a dental composition formulated, e.g., as a mouthwash, toothpaste, a composition for root canal cleaning and disinfection, or a filling composition with biofilm inhibition/prevention properties. In other particular embodiments, the pharmaceutical composition of the invention is formulated for hygienic wash.

Pharmaceutical compositions according to the present invention, when formulated for inhalation, may be administered utilizing any suitable device known in the art, such as metered dose inhalers, liquid nebulizers, dry powder inhalers, sprayers, thermal vaporizers, electrohydrodynamic aerosolizers, and the like.

Pharmaceutical compositions according to the present invention, when formulated for administration route other than parenteral administration, may be in a form suitable for oral use, e.g., as tablets, troches, lozenges, aqueous, or oily suspensions, dispersible powders or granules, emulsions, hard or soft capsules, or syrups or elixirs. Compositions intended for oral use may be prepared according to any method known to the art for the manufacture of pharmaceutical compositions and may further comprise one or more agents selected from sweetening agents, flavoring agents, coloring agents and preserving agents in order to provide pharmaceutically elegant and palatable preparations. Tablets contain the active agent(s) in admixture with non-toxic pharmaceutically acceptable excipients, which are suitable for the manufacture of tablets. These excipients may be, e.g., inert diluents such as calcium carbonate, sodium carbonate, lactose, calcium phosphate, or sodium phosphate; granulating and disintegrating agents, e.g., corn starch or alginic acid; binding agents, e.g., starch, gelatin or acacia; and lubricating agents, e.g., magnesium stearate, stearic acid, or talc. The tablets may be either uncoated or coated utilizing known techniques to delay disintegration and absorption in the gastrointestinal tract and thereby provide a sustained action over a longer period. For example, a time delay material such as glyceryl monostearate or glyceryl distearate may be employed. They may also be coated using the techniques described in the U.S. Pat. Nos. 4,256,108, 4,166,452 and 4,265,874 to form osmotic therapeutic tablets for control release. The pharmaceutical composition of the invention may also be in the form of oil-in-water emulsion.

The pharmaceutical compositions of the invention may be formulated for controlled release of the active agent. Such compositions may be formulated as controlled-release matrix, e.g., as controlled-release matrix tablets in which the release of a soluble active agent is controlled by having the active diffuse through a gel formed after the swelling of a hydrophilic polymer brought into contact with dissolving liquid (in vitro) or gastro-intestinal fluid (in vivo). Many polymers have been described as capable of forming such gel, e.g., derivatives of cellulose, in particular the cellulose ethers such as hydroxypropyl cellulose, hydroxymethyl cellulose, methylcellulose or methyl hydroxypropyl cellulose, and among the different commercial grades of these ethers are those showing fairly high viscosity. In other configurations, the compositions comprise the active agent formulated for controlled release in microencapsulated dosage form, in which small droplets of the active agent are surrounded by a coating or a membrane to form particles in the range of a few micrometers to a few millimeters.

Another contemplated formulation is depot systems, based on biodegradable polymers, wherein as the polymer degrades, the active agent is slowly released. The most common class of biodegradable polymers is the hydrolytically labile polyesters prepared from lactic acid, glycolic acid, or combinations of these two molecules. Polymers prepared from these individual monomers include poly (D,L-lactide) (PLA), poly (glycolide) (PGA), and the copolymer poly (D,L-lactide-co-glycolide) (PLG).

The pharmaceutical compositions of the invention can be provided in a variety of dosages, wherein the actual dose administered will depend on the state of the individual treated, and will be determined as deemed appropriate by the practitioner.

In still another aspect, the present invention relates to a compound of the formula I as defined in any one of the embodiments above, including the compounds wherein $R_1$ is —$CH_2$—; $R_2$ and $R_3$ are H; and: (i) n is 5; $R_4$ and $R_5$ are —$(CH_2)_2$—; and Y is 1-methyl-imidazolium-3-yl or —$N^+(CH_3)_3$; (ii) n is 5; $R_4$ and $R_5$ are —$(CH_2)_3$—; and Y is —$P^+(C_4H_9)_3$; (iii) n is 5; $R_4$ and $R_5$ are —$(CH_2)_4$—; and Y is —$N^+(CH_3)_3$; (iv) n is 6; $R_4$ and $R_5$ are —$(CH_2)_2$—; and Y is —$N^+(CH_3)_3$; (v) n is 6; $R_4$ and $R_5$ are —$(CH_2)_4$—; and Y is —$N^+(CH_3)_3$; (vi) n is 6; $R_4$ and $R_5$ are —$(CH_2)_4$—; and Y is 1-pyridinium; or (vii) n is 6; $R_4$ and $R_5$ are —$(CH_2)_2$—; and Y is 1-methyl-imidazolium-3-yl, for use in inhibiting or disrupting biofilm formation, or reducing biofilm.

In specific embodiments, the compound used for inhibiting or disrupting biofilm formation, or for reducing biofilm, is a compound of the formula I, wherein $R_1$ is —$CH_2$—; $R_2$ and $R_3$ are H; $R_4$ and $R_5$ are identical and each one is —$(CH_2)_{2-10}$—, i.e., —$(CH_2)_2$, —$(CH_2)_3$, —$(CH_2)_4$, —$(CH_2)_5$, —$(CH_2)_6$, —$(CH_2)_7$, —$(CH_2)_8$, —$(CH_2)_9$, or —$(CH_2)_{10}$; Y is —$N^+(CH_3)_3$, —$N^+(C_2H_5)_3$, —$P^+(CH_3)_3$, —$P^+(C_2H_5)_3$, or 1-methyl-imidazolium-3-yl; n is 5 or 6; and X is a pharmaceutically acceptable anion, wherein each one of the combinations of $R_1$-$R_5$, Y, n, and X defined herein represents a specific such compound.

In certain embodiments, the use of the compound of the formula I according to the present invention results in increased sensitivity to antibiotic treatment.

In yet a further aspect, the present invention relates to a method for inhibiting or disrupting biofilm formation, or reducing biofilm, in an individual in need thereof, comprising administering to said individual a therapeutically effective amount of a compound of the formula I as defined in any one of the embodiments above, including the compounds wherein $R_1$ is —$CH_2$—; $R_2$ and $R_3$ are H; and: (i) n is 5; $R_4$ and $R_5$ are —$(CH_2)_2$—; and Y is 1-methyl-imidazolium-3-yl or —$N^+(CH_3)_3$; (ii) n is 5; $R_4$ and $R_5$ are —$(CH_2)_3$—; and Y is —$P^+(C_4H_9)_3$; (iii) n is 5; $R_4$ and $R_5$ are —$(CH_2)_4$—; and Y is —$N^+(CH_3)_3$; (iv) n is 6; $R_4$ and $R_5$ are —$(CH_2)_2$—; and Y is —$N^+(CH_3)_3$; (v) n is 6; $R_4$ and $R_5$ are —$(CH_2)_4$—; and Y is —$N^+(CH_3)_3$; (vi) n is 6; $R_4$ and $R_5$ are —$(CH_2)_4$—; and Y is 1-pyridinium; or (vii) n is 6; $R_4$ and $R_5$ are —$(CH_2)_2$—; and Y is 1-methyl-imidazolium-3-yl. In certain embodiments, this method results in increased sensitivity of said individual to an antibiotic treatment, and optionally further comprises administering to said individual a therapeutically effective amount of said antibiotic.

The invention will now be illustrated by the following non-limiting Examples.

EXAMPLES

Experimental
Chemical Syntheses

General methods. Starting materials were purchased from Sigma-Aldrich, Alfa Aesar, TCI, Cambridge Isotope Laboratories, and Bio-Lab Ltd. Chemical reactions were monitored by TLC (Merck, silica gel 60 F254) and the compounds were purified by $SiO_2$ flash chromatography (Merck Kieselgel 60). $^1H$ and $^{13}C$ NMR spectra were recorded on 400 and 500 MHz Bruker Avance NMR spectrometers at 25°

C. Chemical shifts (δ) are given in parts per million (ppm) and spin-spin coupling (J) is given in Hz. The chemical shifts are relative to residual HDO signal (at δ 4.80 ppm for the $^1$H NMR) when the solvent is D$_2$O, to residual CHCl$_3$ signal (at δ 7.26 ppm for the $^1$H NMR and 77.2 ppm for the $^{13}$C NMR) when the solvent is CDCl$_3$, or to residual DMSO (at δ 2.50 ppm for the $^1$H NMR and 39.5 ppm for the $^{13}$C NMR) when the solvent is DMSO. Determination of C, H, and N compositions were performed using the Perkin-Elmer 2400 series II Analyzer. High-resolution electrospray mass spectra were recorded on a Waters Synapt instrument.

Compound 5 (Adiri et al. (2013). In the final step, to a solution of 4 (50 mg, 42 μmol) in water was added sodium hydroxide (17 mg, 0.42 mmol). The solvent was removed by evaporation to afford a white solid (59 mg, 100%). $^1$H NMR (D$_2$O): δ 6.73 (s, ArH, 10H), 4.46 (d, J=16 Hz, ArCH$_2$Ar, 10H), 4.21 (d, J=16 Hz, ArCH$_2$Ar, 10H), 3.78 (s, ArOCH$_2$COONa, 10H) ppm. $^{13}$C NMR: δ 178.7, 150.4, 129.7, 115.5, 68.8, 30.2 ppm.

Compound 6a (Yao et al. (2012). Carbon tetrabromide (19.9 g, 60 mmol) was added in small portions to a solution of 1,4-bis(2-hydroxyethoxy)benzene (5.0 g, 25 mmol) and triphenylphosphine (15.7 g, 60 mmol) in anhydrous acetonitrile (0.12 L); the reaction mixture was kept at 0° C. during the addition. The resulting mixture was then warmed to 25° C. for 4 h under argon atmosphere. The product was precipitated by the addition of cold water (0.2 L), and the solid was filtered and washed with methanol/water (3:2, 3×100 mL). The product was recrystallized from methanol to obtain the title compound as white flake-like crystals (5.8 g, 71%). $^1$H NMR (400 MHz, CDCl$_3$): δ 6.86 (s, ArH, 4H), 4.24 (t, J=6.2 Hz, ArOCH$_2$CH$_2$Br, 4H), 3.61 (t, J=6.3 Hz, ArOCH$_2$CH$_2$Br, 4H) ppm. $^{13}$C NMR (100 MHz, CDCl$_3$): δ 152.9, 116.1, 68.8, 29.4 ppm.

Compound 6b. Carbon tetrachloride (5.8 mL, 60 mmol) was added in small portions to a solution of 1,4-bis(2-hydroxyethoxy)benzene (5.0 g, 25 mmol) and triphenylphosphine (15.7 g, 60 mmol) in anhydrous acetonitrile (0.12 l), and the reaction mixture was kept at 0° C. during the addition. The resulting mixture was then warmed to 25° C. for 4.5 hours under argon atmosphere. The product was precipitated by the addition of cold water (0.2 l), and the solid was filtered and washed with methanol/water (3:2, 3×0.1 l). The product was recrystallized from methanol to obtain 6b as white solid (2.6 g, 44%). $^1$H NMR (CDCl$_3$): δ 6.68 (s, ArH, 4H), 4.18 (t, J=5.7 Hz, ArOCH$_2$CH$_2$Cl, 4H), 3.78 (t, J=5.7 Hz, ArOCH$_2$CH$_2$Cl, 4H) ppm. $^{13}$C NMR: δ 152.9, 116.1, 68.9, 42.1 ppm.

Compound 7a (Yao et al., 2012; Ogoshi et al., 2012). To a solution of 6a (4.0 g, 12 mmol) and paraformaldehyde (1.1 g, 37 mmol) in 1,2-dichloroethane (60 mL) was added BF$_3$.OEt$_2$ (3.5 g, 25 mmol). The reaction mixture was kept at 25° C. for 1 h under argon atmosphere. The reaction mixture was washed with water (2×50 mL) and dried with sodium sulfate and concentrated in vacuo. The product was purified by chromatography (silica gel; petroleum ether: dichloromethane) to afford 7a as a white solid (1.58 g, 38%). $^1$H NMR (400 MHz, CDCl$_3$): δ 6.90 (s, ArH, 10H), 4.22 (t, J=5.7 Hz, ArOCH$_2$CH$_2$Br, 20H), 3.84 (s, ArCH$_2$Ar, 10H), 3.62 (t, J=5.7 Hz, ArOCH$_2$CH$_2$Br, 20H) ppm. $^{13}$C NMR (100 MHz, CDCl$_3$): δ 149.8, 129.2, 116.2, 69.1, 30.9, 29.5 ppm.

Compound 7b. To a solution of 6b (2.0 g, 8.5 mmol) and paraformaldehyde (0.76 g, 25 mmol) in 1,2-dichloroethane (30 mL) was added BF$_3$.OEt$_2$ (2.4 g, 17 mmol). The reaction mixture was kept at 25° C. under argon atmosphere for 1 hour. The reaction mixture was washed with water (2×50 mL), brine (2×50 mL) and dried with sodium sulfate. The product was purified by column chromatography (silica gel; petroleum ether:dichloromethane) to afford 7b as white solid (1.1 g, 52%). $^1$H NMR (CDCl$_3$): δ 6.91 (s, ArH, 10H), 4.15 (t, J=5.5 Hz, ArOCH$_2$CH$_2$Cl, 20H), 3.83 (s, ArCH$_2$Ar, 10H), 3.80 (t, J=5.5 Hz, ArOCH$_2$CH$_2$Cl, 20H) ppm. $^{13}$C NMR: δ 149.8, 129.1, 115.9, 69.1, 43.2, 29.4 ppm.

Compound 8a (Whiteside et al., 2002). A mixture of hydroquinone (8.0 g, 73 mmol), 1,3-dibromopropane (44 g, 0.22 mol), and potassium carbonate (45 g, 0.33 mol) were refluxed in acetone (0.13 L) for 24 hours under argon atmosphere. The reaction mixture was cooled to 25° C. and filtered through celite, and the solvent was evaporated under vacuum. The residue was dissolved in dichloromethane (0.1 L), washed with water (2×50 mL), 3 N HCl (2×50 mL), and brine (2×50 mL), dried with sodium sulphate, and concentrated in vacuo. The product was purified by column chromatography (silica gel; eluent: hexane/ethyl acetate). Further purification by recrystallization in ethyl acetate/hexane afforded 8a as a white solid (9.5 g, 37%). $^1$H NMR (400 MHz, CDCl$_3$): δ 6.84 (s, ArH, 4H), 4.05 (t, J=5.9 Hz, ArOCH$_2$CH$_2$CH$_2$Br, 4H), 3.60 (t, J=6.7 Hz, ArOCH$_2$CH$_2$CH$_2$Br, 4H), 2.29 (m, ArOCH$_2$CH$_2$CH$_2$Br, 4H) ppm. $^{13}$C NMR (100 MHz, CDCl$_3$): δ 153.0, 115.5, 65.9, 32.5, 30.2 ppm.

Compound 9a (Ogoshi et al., 2012). To a solution of 8a (2.5 g, 7.1 mmol) in 1,2-dichloroethane (60 mL) was added paraformaldehyde (0.67 g, 22 mmol) followed by BF$_3$.OEt$_2$ (1.1 g, 7.8 mmol). The reaction mixture was kept at 30° C. for 30 min under argon atmosphere. The resulting mixture was cooled to 25° C., and the crude product was precipitated by addition of methanol (0.2 L). The product was purified by chromatography (silica gel; hexane:dichloromethane) to afford the title compound as a white solid (1.1 g, 43%). $^1$H NMR (400 MHz, CDCl$_3$): δ 6.74 (s, ArH, 10H), 3.99 (t, J=6.3 Hz, ArOCH$_2$CH$_2$CH$_2$Br, 20H), 3.75 (s, ArCH$_2$Ar, 10H), 3.52 (t, J=6.5 Hz, ArOCH$_2$CH$_2$CH$_2$Br, 20H), 2.21 (m, ArOCH$_2$CH$_2$CH$_2$Br, 20H) ppm. $^{13}$C NMR (100 MHz, CDCl$_3$): δ 149.8, 128.5, 115.3, 66.3, 32.7, 30.5, 29.9 ppm.

Compound 10a. To a solution of 6a (2.5 g, 7.7 mmol) and paraformaldehyde (0.46 g, 15 mmol) in chloroform (0.12 mL) was added BF$_3$.OEt$_2$ (2.19 g, 15 mmol). The reaction mixture was kept at 25° C. under argon atmosphere for 3 hours. The reaction mixture was washed with water (2×100 mL), brine (2×100 mL) and dried with sodium sulfate. The product was purified by column chromatography (silica gel; petroleum ether:dichloromethane) to afford 10a as white solid (0.38 g, 15%). $^1$H NMR (D$_2$O): δ 6.78 (s, ArH, 12H), 4.16 (t, J=6.2 Hz, ArOCH$_2$CH$_2$Br, 24H), 3.86 (s, ArCH$_2$Ar, 12H), 3.55 (t, J=6.2 Hz, ArOCH$_2$CH$_2$Br, 24H) ppm. $^{13}$C NMR: δ 150.3, 128.6, 115.9, 69.1, 30.7, 30.4 ppm.

Compound 11. Trimethylamine (33% in ethanol, 1.0 mL, 5.7 mmol) was added to a solution of 8a (0.2 g, 0.57 mmol) in ethanol (5 mL). The resulting mixture was refluxed in a pressure tube for 24 hours. After cooling to 25° C., the precipitate was filtered, washed with ethanol, and dried under vacuum to afford white solid (0.26 g, 97%). $^1$H NMR (400 MHz, D$_2$O): δ 6.96 (s, ArH, 4H), 4.11 (t, J=5.8 Hz, ArOCH$_2$, 4H), 3.52 (m, CH$_2$CH$_2$N, 4H), 3.12 (s, N(CH$_3$)$_3$, 18H), 2.24 (m, ArOCH$_2$CH$_2$, 4H) ppm. $^{13}$C NMR (125 MHz, D$_2$O): δ 153.1, 117.0, 66.2, 64.7, 53.7, 23.4 ppm. HRMS: m/z calcd. for C$_{18}$H$_{34}$O$_2$N$_2$Br$_3$ [M+Br]$^-$ 547.0170, found 547.0181.

Compound 12. Trimethyl phosphine (1 M in THF, 9.0 mL, 9 mmol) was added to 8a (0.15 g, 0.43 mmol) under argon atmosphere. The solution was refluxed for 24 hours in a pressure tube. The precipitate was filtered, washed with THF, and dried under vacuum to afford a white solid (0.15 g, 69%). $^1$H NMR (400 MHz, D$_2$O): 7.00 (s, ArH, 4H), 4.12 (t, J=5.8 Hz, ArOCH$_2$, 4H), 2.42-2.34 (m, ArOCH$_2$CH$_2$, 4H), 2.09-2.04 (m, CH$_2$P(CH$_3$)$_3$, 4H), 1.86 (d, J=14.3 Hz, P(CH$_3$)$_3$, 18H) ppm. $^{13}$C NMR (100 MHz, D$_2$O): δ 153.1, 117.0, 68.6 (d, J=16 Hz), 21.7, 21.2 (d, J=54 Hz), 8.0 (d, J=55 Hz) ppm. $^{31}$P NMR (162 MHz, D$_2$O, H$_3$PO$_4$ reference): δ 27.3 ppm. HRMS: m/z calcd. for C$_{18}$H$_{34}$O$_2$P$_2$Br$_3$ [M+Br]$^-$ 580.9584, found 580.9599.

Compound 21 (Ma et al., 2011). In the final step, trimethylamine (33% in ethanol, 6.4 mL, 24 mmol) was added to a solution of 7a (1.0 g, 0.59 mmol) in ethanol (50 mL). The resulting mixture was refluxed for 24 hours. After cooling to 25° C., the solvent was removed under vacuum and the residue was dissolved in water (20 mL). The solution was filtered and the solvent was removed by evaporation to afford colorless solid (1.2 g, 89%). $^1$H NMR (D$_2$O): δ 6.97 (s, ArH, 10H), 4.48 (s, ArOCH$_2$CH$_2$N, 20H), 3.95 (s, ArCH$_2$Ar, 10H), 3.83 (s, ArOCH$_2$CH$_2$N, 20H), 3.24 (s, N(CH$_3$)$_3$, 90H) ppm. $^{13}$C NMR: δ 150.36, 130.93, 117.49, 65.88, 64.46, 55.05, 30.56 ppm.

Compound 22 (Yao et al., 2012; Ogoshi et al., 2012). In the final step, a mixture of 7a (1.2 g, 0.76 mmol) and N-methylimidazole (1.2 g, 15 mmol) in toluene was kept at 120° C. for 24 hours. After cooling to 25° C., the solvent was removed under vacuum and the residue was recrystallized from ethanol/diethyl ether (1:2) to afford a white solid (1.8 g, 98%). $^1$H NMR (D$_2$O): δ 8.4 (br, Imidazole-H, 10H) 7.63 (s, Imidazole-H, 10H), 7.15 (s, ArH, 10H), 6.76 (s, Imidazole-H, 10H), 4.64 (s, Ar—OCH$_2$CH$_2$, 20H), 4.47 (s, ArOCH$_2$CH$_2$, 20H), 3.66 (s, Imidazole-CH$_3$, 30H), 3.62 (s, ArCH$_2$Ar, 10H) ppm. $^{13}$C NMR: δ 150.08, 137.31, 129.94, 124.64, 123.46, 116.26, 67.79, 50.25, 36.64, 29.92 ppm.

Compound 23. An excess amount of triethylamine (5.0 mL, 36 mmol) was added to a solution of 7a (0.46 g, 0.27 mmol) in ethanol (5.0 mL). The resulting mixture was refluxed in a pressure tube for 5 days. After cooling to 25° C., the product was precipitated by the addition of diethyl ether. The precipitate was filtered, and the solid was washed with diethyl ether and acetone to remove excess triethylamine. The solid was dissolved in water and concentrated to afford a colorless solid that turned to thick oil when exposed to air (0.40 g, 54%). $^1$H NMR (400 MHz, DMSO-d$_6$): δ 7.00 (s, ArH, 10H), 4.52 (br, ArOCH$_2$CH$_2$N, 20H), 3.98 (br, ArOCH$_2$CH$_2$N, 20H), 3.75 (s, ArCH$_2$Ar, 10H), 3.51 (br, NCH$_2$CH$_3$, 60H), 1.26 (t, NCH$_2$CH$_3$, J=7.1 Hz, 90H) ppm. $^{13}$C NMR (100 MHz, CDCl$_3$): δ 148.8, 128.3, 115.5, 62.1, 55.8, 53.1, 28.7, 7.7 ppm.

Compound 24. 2-Dimethylaminoethanol (0.85 g, 9.5 mmol) was added to a solution of 7a (0.20 g, 0.12 mmol) in ethanol. The resulting mixture was refluxed for 48 hours. After cooling to 25° C., the solvent was removed under vacuum and the residue was dissolved in water (5.0 mL). The solution was filtered and the solvent was removed by evaporation. Finally the residue was washed with ethanol and dried under vacuum to afford a light brown solid (0.22 g, 71%). $^1$H NMR (D$_2$O): δ 6.96 (s, ArH, 10H), 4.55 (br, ArOCH$_2$CH$_2$, 20H), 4.07-3.97 (ArCH$_2$Ar, ArOCH$_2$CH$_2$N & NCH$_2$CH$_2$OH, 50H), 3.65 (br, NCH$_2$CH$_2$OH, 20H), 3.30 (s, N(CH$_3$)$_2$, 60H) ppm. $^{13}$C NMR: δ 150.5, 131.0, 117.6, 67.5, 65.0, 64.5, 56.6, 50.5, 30.8 ppm.

Compound 25. Trimethylamine (33% in ethanol, 0.79 mL, 4.4 mmol) was added to a solution of 9a (0.20 g, 0.11 mmol) in ethanol (10 mL). The resulting mixture was refluxed for 24 hours. After cooling to 25° C., the solvent was removed under vacuum and the residue was dissolved in water (5.0 mL). The solution was filtered and the solvent was removed by evaporation. The residue recrystallized as light brown crystals in ethanol (0.21 g, 79%). $^1$H NMR (D$_2$O): δ 6.78 (s, ArH, 10H), 3.90 (br, ArOCH$_2$CH$_2$CH$_2$ & ArCH$_2$Ar, 30H), 3.39 (br, ArOCH$_2$CH$_2$CH$_2$, 20H), 3.10 (br, N(CH$_3$)$_3$, 90H), 2.07 (br, ArOCH$_2$CH$_2$CH$_2$, 20H) ppm. $^{13}$C NMR: δ 150.5, 129.9, 116.9, 66.6, 64.4, 53.6, 30.8, 23.4 ppm.

Compound 26. Prepared similarly to compound 21 by reacting 7b (0.15 g, 0.12 mmol) with trimethylamine (33% in ethanol, 3.0 mL, 11 mmol) in acetonitrile for 48 h; white solid (0.17 g, 78%). δ $^1$H NMR (400 MHz, D$_2$O): δ 6.98 (s, ArH, 10H), 4.48 (s, ArOCH$_2$CH$_2$N, 20H), 3.95 (s, ArCH$_2$Ar, 10H), 3.84 (s, ArOCH$_2$CH$_2$N, 20H), 3.25 (s, N(CH$_3$)$_3$, 90H) ppm. $^{13}$C NMR (100 MHz, D$_2$O): δ 150.1, 130.7, 117.2, 65.5, 64.1, 54.7, 30.2 ppm.

Compound 27. Prepared similarly to compound 21 by reacting 10a (0.15 g, 74 μmol) with trimethylamine (33% in ethanol, 0.70 mL, 3.7 mmol); white solid (0.16 g, 73%). $^1$H NMR (500 MHz, D$_2$O): δ 6.94 (s, ArH, 12H), 4.54 (t, J=4.9 Hz, ArOCH$_2$CH$_2$N, 24H), 3.98 (s, ArCH$_2$Ar, 12H), 3.78 (t, J=4.8 Hz, ArOCH$_2$CH$_2$N, 24H), 3.15 (s, N(CH$_3$)$_3$, 108H) ppm. $^{13}$C NMR (125 MHz, D$_2$O): δ 150.3, 129.6, 116.7, 65.6, 63.9, 54.5, 30.6 ppm.

Compound 28. An excess amount of triethyl amine (5.0 mL, 36 mmol) was added to a solution of 9a (0.40 g, 0.22 mmol) in ethanol (5.0 mL). The resulting mixture was refluxed in a pressure tube for 7 days. After cooling to 25° C., the product was precipitated by the addition of diethyl ether. The precipitate was filtered, and the solid was washed with diethyl ether and acetone. The product was sonicated in acetone (5×10 mL) to remove excess triethyl amine. Finally the solid was dissolved in water and concentrated to afford a white solid (0.42 g, 68%). $^1$H NMR (400 MHz, DMSO-d$_6$): δ 6.80 (s, ArH, 10H), 4.19 & 3.89 (br, ArOCH$_2$CH$_2$N, 20H), 3.73 (s, ArCH$_2$Ar, 10H), 3.44 (br, ArOCH$_2$CH$_2$N, 20H), 3.43 (br, NCH$_2$CH$_3$, 60H), 2.22 (br, ArOCH$_2$CH$_2$CH$_2$, 20H), 1.26 (t, J=7.0 Hz, NCH$_2$CH$_3$, 90H) ppm. $^{13}$C NMR (100 MHz): δ 148.7, 127.9, 113.7, 65.0, 53.6, 52.3, 28.7, 22.4, 7.4 ppm. Anal. calcd. for C$_{125}$H$_{230}$Br$_{10}$N$_{10}$O$_{10}$. 10.75H$_2$O: C, 49.62; H, 8.38; N, 4.63. Found: C, 49.31; H, 8.06; N, 4.46.

Compound 29. Trimethylphosphine (1.0 M in THF, 2.2 mL, 2.2 mmol) was added to a solution of 9a (0.10 g, 0.05 mmol) in acetonitrile (6.0 mL). The resulting mixture was refluxed in a pressure tube for 96 hours. After cooling to 25° C., the precipitate was filtered, washed with diethyl ether, and dried under vacuum to afford 29 as white solid (0.12 g, 86%). $^1$H NMR (400 MHz, DMSO-d$_6$): δ 6.85 (s, ArH, 10H), 4.07 & 3.90 (br, ArOCH$_2$CH$_2$CH$_2$P, 20H), 3.78 (s, ArCH$_2$Ar, 10H), 2.69-2.60 (m, CH$_2$P(CH$_3$)$_3$, 20H), 2.00 (d, J=14.7 Hz, CH$_2$P(CH$_3$)$_3$ & ArOCH$_2$CH$_2$CH$_2$P, 110H) ppm. $^{13}$C NMR (125 MHz, DMSO-d$_6$): δ 148.7, 127.8, 114.1, 67.5 (d, J=17 Hz), 28.7, 21.7, 19.7 (d, J=56 Hz), 7.5 (d, J=55 Hz) ppm. $^{31}$P NMR (162 MHz, DMSO-d$_6$, H$_3$PO$_4$ reference): δ 30.0 ppm. HRMS: m/z calcd. for C$_{95}$H$_{170}$O$_{10}$P$_{10}$Br$_{11}$ [M+Bi]$^-$ 2662.1098, found 2662.1116.

Compound 30. Triethylphosphine (1.0 M in THF, 2.2 mL, 2.2 mmol) was added to a solution of 9a (0.10 g, 0.05 mmol) in dry acetonitrile (8.0 mL). The resulting mixture was refluxed in a pressure tube for 72 hours. After cooling to 25° C., diethyl ether was added to give a white precipitate. The precipitate was filtered, washed with diethyl ether, and dried under vacuum to afford 30 as white solid (68 mg, 41%). $^1$H NMR (500 MHz, DMSO-d$_6$): δ 6.81 (s, ArH, 10H), 4.15 & 3.84 (br, ArOCH$_2$CH$_2$CH$_2$P, 20H), 3.76 (s, ArCH$_2$Ar, 10H), 2.61-2.55 (m, CH$_2$P(CH$_2$CH$_3$)$_3$, 20H), 2.46-2.39 (m, P(CH$_2$CH$_3$)$_3$, 60H), 2.06 (m, OCH$_2$CH$_2$CH$_2$, 20H), 1.23-1.17 (m, P(CH$_2$CH$_3$)$_3$, 90H) ppm. $^{13}$C NMR (125 MHz, DMSO-d$_6$): δ 148.7, 127.9, 113.8, 67.5 (d, J=16 Hz), 28.8, 21.7, 14.1 (d, J=50 Hz), 10.8 (d, J=48 Hz), 5.4 (d, J=5 Hz) ppm. $^{31}$P NMR (162 MHz, D$_2$O, H$_3$PO$_4$ reference): δ 39.8 ppm. Anal. calcd. for C$_{125}$H$_{230}$Br$_{10}$P$_{10}$O$_{10}$·14.45H$_2$O: C, 45.77; H, 7.74.

Found: C, 46.02; H, 8.00. HRMS: m/z calcd. for C$_{125}$H$_{230}$O$_{10}$P$_{10}$Br$_{11}$ [M+Br]$^-$ 3081.5760, found 3081.5796.

Biological Assays

Analysis of bacterial growth. The assay was performed as previously described (Feldman et al., 2012) with minor modifications. Briefly, all tested bacterial strains were grown from the frozen stock in Brain Heart Infusion (BHI) broth for 24 hours at 37° C. in 5% CO$_2$. Next, 100 µL of serial 1:2 dilutions of compounds in Tryptic Soy Broth (TSB)+1% glucose (32, 16, 8, 4, 2, 1, and 0.5 µg/mL) were prepared in a flat-bottomed 96-well microplates (Costar, Corning). Control wells with no compound and wells without bacteria containing each tested concentration of the compounds (blanks) were also prepared. An equal volume (100 µL) of bacterial suspension diluted 1:100 (OD$_{600}$=0.01) or 1:10 (OD$_{600}$=0.1) in TSB+1% glucose was added to each well. During a 24 hours incubation at 37° C., growth kinetics were monitored by recording optical density at wavelength 600 nm (OD$_{600}$) using a Tecan plate reader. Each concentration was tested in triplicates, and experiments were repeated three times.

Analysis of biofilm inhibition. The assay was performed as previously described (Joseph et al., 2016; Feldman et al., 2012) with minor modifications. Briefly, all tested bacterial strains were grown from the frozen stock in BHI broth for 24 hours at 37° C. in 5% CO$_2$. Next, 100 µL of serial 1:2 dilutions of compounds in TSB+1% glucose (32, 16, 8, 4, 2, 1, and 0.5 µg/mL) were prepared in flat-bottomed 96-well microplates (Costar, Corning). Control wells with no compounds and wells without bacteria containing each tested concentration of the compounds (blanks) were also prepared. An equal volume (100 µL) of bacterial suspensions diluted 1:100 (OD$_{600}$=0.01) or 1:10 (OD$_{600}$=0.1) in TSB+ 1% glucose was added to each well. After incubation for 24 hours at 37° C. in 5% CO$_2$ under aerobic conditions, spent media and free-floating bacteria were removed by turning over the plates. The wells were vigorously rinsed at least four times with doubly distilled water (DDW). Next, 0.4% crystal violet (200 µL) was added to each well. After 45 min, wells were vigorously rinsed three times with DDW to remove unbound dye. After adding 200 µL of 30% acetic acid to each well, the plate was shaken for 15 min to release the dye. Biofilm formation was quantified by measuring the difference between absorbance of untreated and treated bacterial samples for each tested concentration of the compounds and the absorbance of appropriate blank well at 600 nm (A$_{600}$) using Tecan plate reader. The MBIC$_{50}$ was defined as the lowest concentration at which at least 50% reduction in biofilm formation was measured compared to untreated cells. Each concentration of compound was tested in five replicates, and three to six independent experiments were performed.

Analysis of biofilm eradication. Biofilm eradication activity of the tested compounds determined against mature 24-h-old biofilms was performed as previously described (Pompilio et al., 2015). Briefly, bacterial species were allowed to form biofilms in TSB+1% glucose medium in a 96-well flat-bottom microtiter plate by incubation for 24 hours at 37° C. in 5% CO$_2$. Following the 24-h incubation, biofilm samples were washed twice with sterile DDW, then were exposed to 200 µL of the tested compounds prepared at concentrations of 2, 4, 8, 16, 32, 64, and 128 µg/mL in TSB+1% glucose medium. After incubation at 37° C. in 5% CO$_2$ for 24 h, non-adherent bacteria were removed by washing twice with sterile DDW, and biofilm samples were stained with crystal violet as described for biofilm inhibition assay. Untreated biofilm samples were used as control. Biofilms were quantified by measuring the absorbance at 600 nm. The mean IC$_{50}$ value for biofilm eradication (MBEC$_{50}$) was defined as the lowest concentration at which at least 50% reduction in biomass of preformed biofilms was measured compared to untreated biofilm samples. Concentrations were tested in five replicates, and three independent experiments were performed.

Rat red blood cell haemolysis assay. A sample of rat red blood cells (2% w/w) were incubated with each of the tested compounds for 1 hours at 37° C. in 5% CO$_2$ using the double dilution method starting at a concentration of 256 µg/mL. The negative control was phosphate-buffered saline (PBS), and the positive control was 1% w/v solution of Triton X-100 (which induced 100% haemolysis). Following centrifugation (2000 rpm, 10 min, ambient temperature), the supernatant was removed and absorbance at 550 nm was measured using a microplate reader (SpectraMax-M2). The results are expressed as percentage of haemoglobin released relative to the positive control (Triton X-100). Experiments were performed in triplicate, and the results are an average of experiments in blood samples taken from at least two rats.

pH stability assay. Aqueous solutions of compounds 28 and 30 were treated with dilute HCl to obtain a pH of 2.3. Basic pH values of 10.7 and 10.2 of solutions of the compounds 28 and 30, respectively, were obtained by adding dilute ammonia solution. The solutions were kept at room temperature for 4 hours and then freeze-dried. The $^1$H spectra recorded for all samples matched the $^1$H HMR spectra of the respective compounds at pH 7.4. Biofilin inhibition studies were conducted with these compounds as described above.

Mammalian cell toxicity assay. A metabolic activity assay was performed to evaluate toxicity of compounds to human cells in culture as previously described (Omata et al., 2006). Briefly, human monocytic THP-1 cells (ATCC TIB 202) were maintained at 37° C. in 5% $CO_2$ in RPMI 1640 supplemented with 10% fetal bovine serum (FBS), 2 mM glutamine, 100 g/mL streptomycin, and 100 units/mL penicillin (all from Biological Industries, Beit HaEmek, Israel). Cystic fibrosis human bronchi epithelial cells IB3-1 (ATCC CRL-2777) and HaCaT human skin keratinocytes were cultured in Dulbecco's Modified Eagle's Medium (DMEM) medium (Invitrogen) supplemented with 10% FBS, 2 mM glutamine, 100 units/mL penicillin, and 100 g/mL streptomycin. Cells were plated in 96-well format (60,000 cells/well for THP1; 10,000 cells/well for IB3-1 and HaCaT) for 24 hours at 37° C., 5% $CO_2$. In Study 1, compound 27 was added at final concentrations of 0, 0.73, 2.94, 11.74, and 46.96 µM to the appropriate wells. In Study 2, compounds were added at final concentrations of 2, 4, 8, 16, 32, 64 and 128 µg/ml to the appropriate wells. Wells without compounds served as controls. Plates were incubated for 1 hour, 24 hours, and 72 hours at 37° C. in 5% $CO_2$. Cell viability was determined using MTT (3-[4,5-dimethylthiazoyl-2-yl]-2,5-diphenyl tetrazolium bromide) assay (Wataha et al., 1992), and cells were observed using light microscopy. The percentage of cell death was determined relative to vehicle-treated cells. Experiments were performed in triplicate, and the results were obtained from two independent experiments.

Study 1. Cationic Pillararenes Inhibit Formation and Eradicate Bacterial Biofilms In the present study, we prepared five positively charged pillar[5]arene derivatives in which the 10 phenolic positions were substituted by positively charged quaternary ammonium or imidazolium groups (compounds 21-25), and as a control, we prepared the negatively charged pillar[5]arene 5, which is decorated with 10 carboxylate groups that are negatively charged under physiological conditions. The compounds were synthesized following synthetic routes similar to those previously described (Ma et al., 2011; Yao et al., 2012; Adiri et al., 2013).

Each compound was tested for its ability to inhibit biofilm formation by Gram-positive and Gram-negative pathogens. The mean $IC_{50}$ value for biofilm inhibition ($MBIC_{50}$) was defined as the lowest concentration at which at least 50% reduction in biofilm formation was measured compared to untreated cells. The results are summarized in Table 1. The most impressive biofilm inhibition properties were observed for deca-trimethylammonium pillar[5]arene 21 and the deca-N-methyl-imidazolium pillar[5]arene 22. The $MBIC_{50}$ values of these compounds against each of the tested biofilm-forming Gram-positive pathogens ranged from 0.4 to 6.4 µM. Inhibition of biofilm formation was selective for Gram-positive strains. None of the cationic pillararenes in this study inhibited the formation of biofilm by Gram-negative strains E. coli ATCC 25922 and P. aeruginosa PAO1.

TABLE 1

Biofilm inhibitory activity of certain pillar[5-6]arenes: $MBIC_{50}$ (µM) against Gram-positive strains[*]

| Compound | Bacterial strain | | | | | |
|---|---|---|---|---|---|---|
| | A | B | C | D | E | F |
| 21 | 0.9 | 3.5 | 3.5 | 0.9 | 3.5 | 1.8 |
| 22 | 0.8 | 1.6 | 1.6 | 0.4 | 3.2 | 6.4 |
| 23 | 1.5 | 5.9 | 5.9 | 1.5 | 5.9 | 5.9 |
| 24 | >12 | >12 | >12 | >12 | >12 | >12 |
| 25 | 1.7 | 6.6 | >13 | 1.7 | 1.7 | 6.6 |
| 26 | 1.1 | 4.4 | 8.8 | 1.1 | 2.2 | 8.8 |
| 27 | 0.4 | 1.5 | 2.9 | 0.4 | 0.7 | 2.9 |
| 5 | >23 | >23 | >23 | >23 | >23 | >23 |
| TMA-Cl | >292 | >292 | >292 | >292 | >292 | >292 |
| TMA-Br | >208 | >208 | >208 | >208 | >208 | >208 |

[*]Compounds were evaluated using the double-dilution method for inhibition biofilm formation by (A) S. aureus subsp. aureus Rosenbach ATCC 33592, (B) S. aureus ATCC 29213, (C) S. aureus BAA/043, (D) E. faecalis ATCC 29212, (E) S. epidermidis RP62A, (F) S. mutans ATCC 700610. TMA-Cl and TMA-Br are tetramethylammonium chloride and tetramethylammonium bromide, respectively. Each value is a mean of at least three independent experiments each including five replicates of each concentration.

Changes in the hydrophilic or hydrophobic balance of the cationic pillar[5]arene had general and significant effects on the inhibition of biofilm formation. Elongation of the aliphatic linker between the pillar[5]arene core and the positively charged group from an ethyl in compound 21 to a propyl chain in compound 25 led to a small but significant reduction in the inhibition of biofilm formation. A similar effect was observed when the quaternary tri-methyl ammonium head groups in compound 21 were replaced by more hydrophobic tri-ethyl quaternary ammonium groups in compound 23. A more pronounced loss of activity was observed when the hydrophilicity of the head groups was increased by the installation of hydroxyethyl-di-methyl quaternary ammonium groups in compound 24; compound 24 did not inhibit biofilm formation at a concentration of 12 µM, the highest concentration tested.

To further evaluate the structural determinants required for biofilm formation inhibition, we examined anti-biofilm activities of several control compounds: Pillar[5]arene 5, which has carboxylic head groups that are negatively charged under physiological conditions, did not inhibit biofilm formation by any of the tested strains. This showed that the positive charge was important for the observed activity. No inhibition of biofilm formation, up to concentrations of 292 µM and 208 µM, was observed for tetramethylammonium bromide (TMA-Br) or tetramethylammonium chloride (TMA-Cl), respectively, indicating that neither the quaternary ammonium head groups nor the halogen ions alone are responsible for the inhibition of biofilm formation by compounds 21-25.

The effect of the halogen ion on the inhibition of biofilm formation in the tested strains was further examined by the preparation of compound 26; the chloride analogue of compound 21. Compounds 21 and 26 had very similar MBIC50 values against four of the tested strains (strains A, B, D, E; Table 1). The halogen ion type did affect the ability of pillararene 26 to inhibit S. aureus BAA/043 (strain C) and S. mutans ATCC 700610 (strain F) biofilm formation; for these strains, the MBIC50 values of compound 26 with the chloride counter ion were two- and four-fold higher than those of compound 21 with the bromide anion, respectively.

Figure 2:
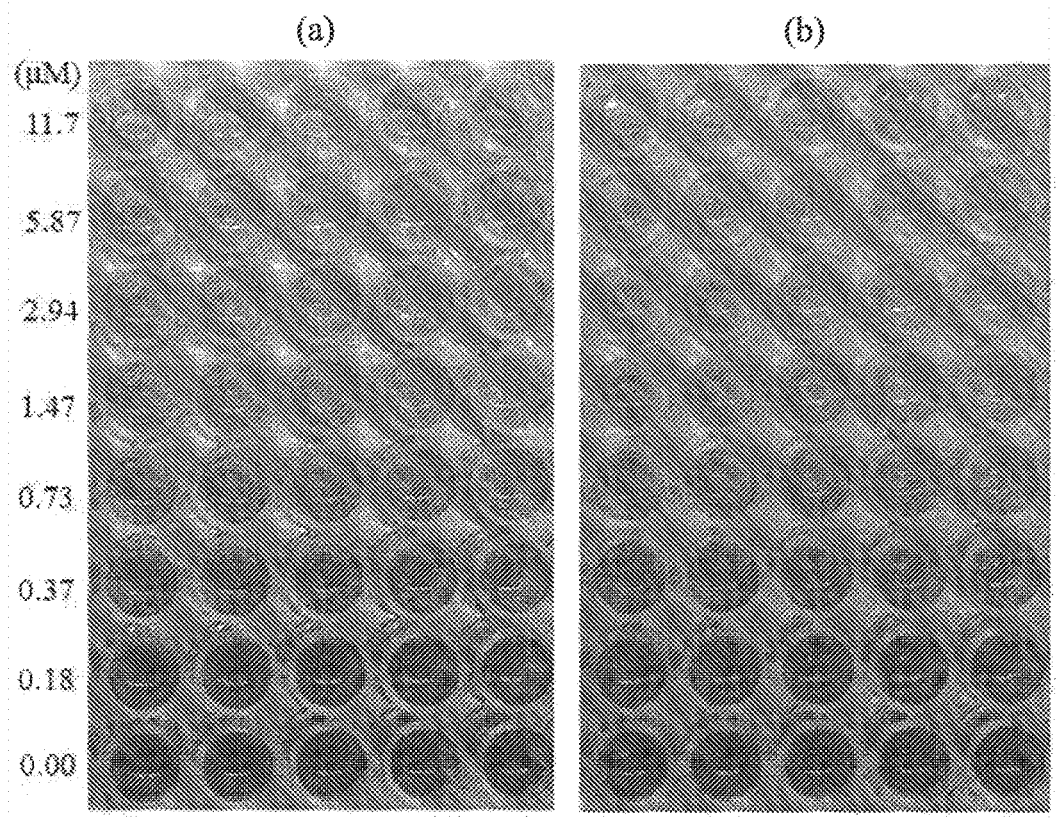
FIG. 2 shows inhibition of biofilm formation by pillar[6] arene 27. Biofilms produced by *S. aureus* subsp. *aureus* Rosenbach ATCC 33592 (a) and by *E. faecalis* ATCC 29212 (b) in the presence of increasing concentrations of 27 were stained with crystal violet. Each concentration of compound was tested in five wells.
Figure 3A:
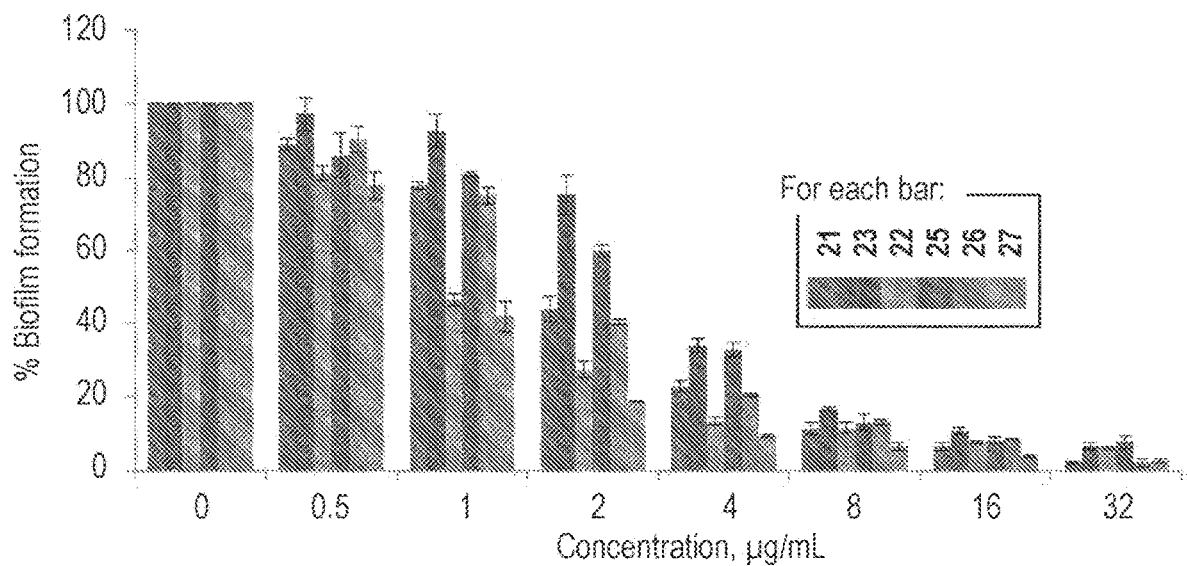
FIGS. 3A-3B show biofilm formation by *E. faecalis* ATCC 29212 (3A) and *S. aureus* subsp. *aureus* Rosenbach ATCC 33592 (3B), evaluated using the double-dilution method with starter inoculum of 1:100 ($OD_{600}$=0.01). Molarity concentration ranges of the tested compounds: (21) 0.22-28.18; (22) 0.20-25.59; (23) 0.18-23.78; (25) 0.21-26.54; (26) 0.27-35.00; and (27) 0.18-23.48 µM. No measurable biofilm inhibition effect was detected for compounds 24 and 5 up to concentrations of 24.88 and 45.36 µM, respectively.
Figure 3B:
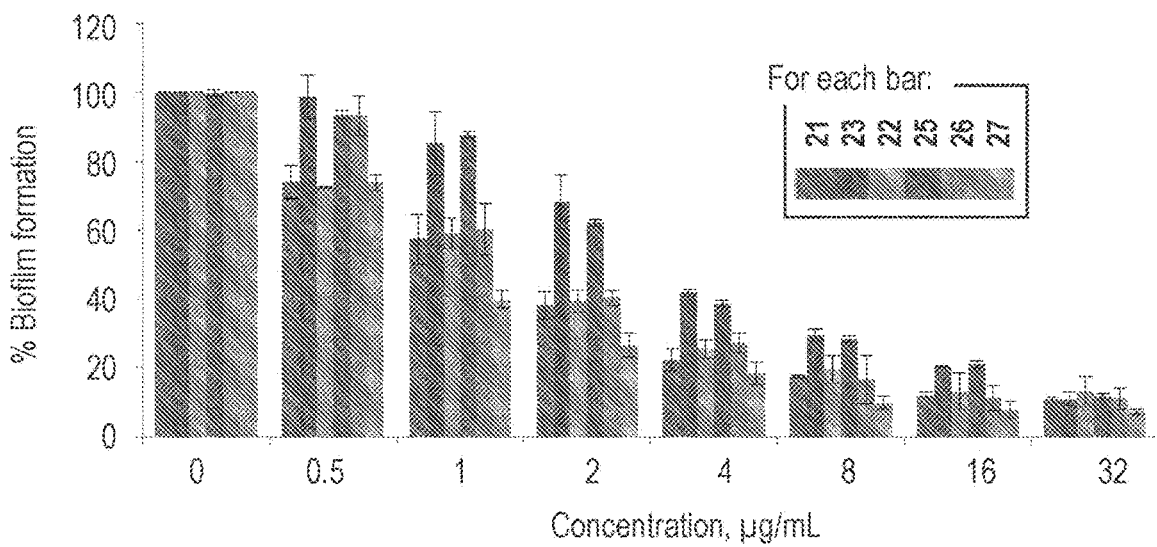

Since 21 demonstrated potent inhibition of biofilm formation by all tested strains of Gram-positive pathogens, we reasoned that increasing the quaternary ammonium cluster size and the overall positive charge of the molecule would further improve the inhibition properties. Hence, we synthesized compound 27, the pillar[6]arene analogue of 21. Compared to compound 21 the overall positive charge of compound 27 is 20% higher. Furthermore, the internal cavity diameter of pillar[6]arene 27 is ~6.7 Å, whereas that of pillar[5]arene 21 is ~4.6 Å (Ogoshi and Yamagishi, 2014). This difference should, in principle, enable compound 27 to bind larger and more structurally diverse molecular guests from the biofilm matrix. Compound 27 was found to be the most potent inhibitor of biofilm formation of all the cationic pillararenes tested strains as summarized in Table 1 and demonstrated visually in FIG. 2. Compared to pillar[5]arene 21, the MBIC50 values of pillar[6]arene analogue 27 were from 2- to 5-fold lower for four of the tested biofilm forming Gram-positive pathogens; no significant difference in the inhibition of biofilm formation between 21 and 27 was observed in for *S. aureus* BAA/043 (strain C, Table 1). For *S. mutans* ATCC 700610, however, compound 21 was slightly more active than 27 (strain F, Table 1). The dose-dependent biofilm inhibition ability of compounds 21-27 against *E. faecalis* ATCC 29212 and *S. aureus* subsp. *aureus* Rosenbach ATCC 33592 is presented in FIG. 3.

Figure 4A:
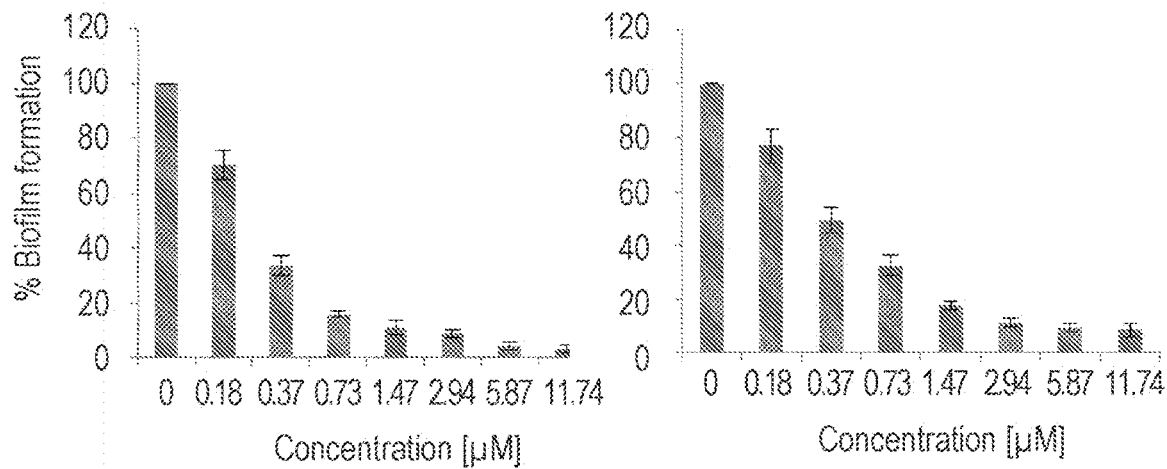
FIGS. 4A-4C show the effect of initial inoculum on biofilm formation inhibition by compound 27. The compound was incubated with *E. faecalis* (ATCC 29212; right panels) and *S. aureus* subsp. *aureus* Rosenbach (ATCC 33592; left panels) at starter inoculums of $OD_{600}$ 0.025 (4A), 0.05 (4B), or 0.10 (4C).
Figure 4B:
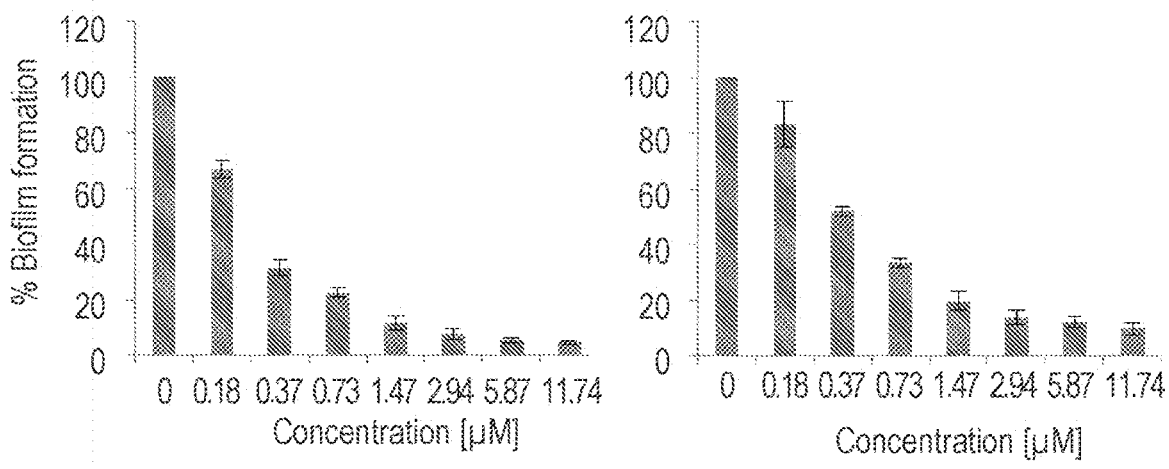
Figure 4C:
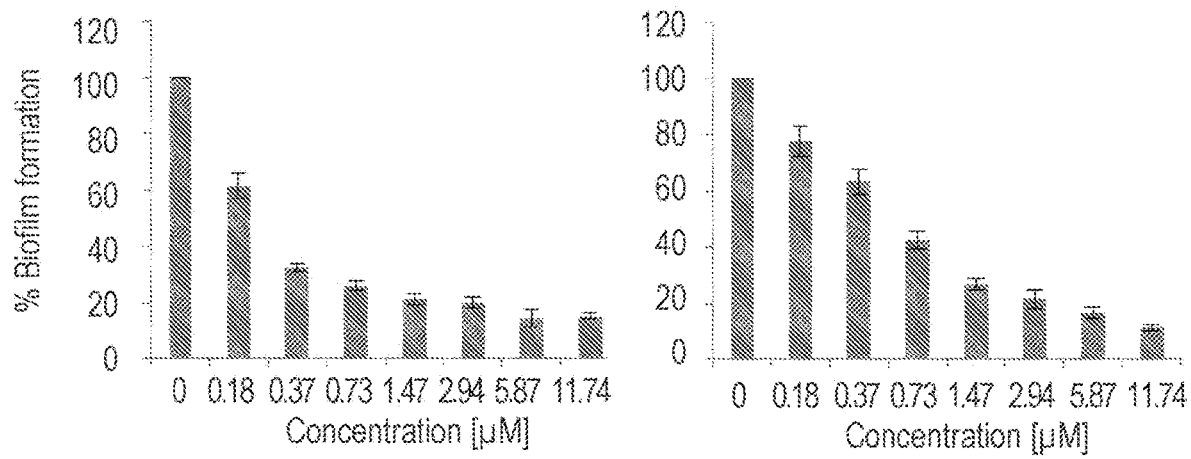
Figure 5A:
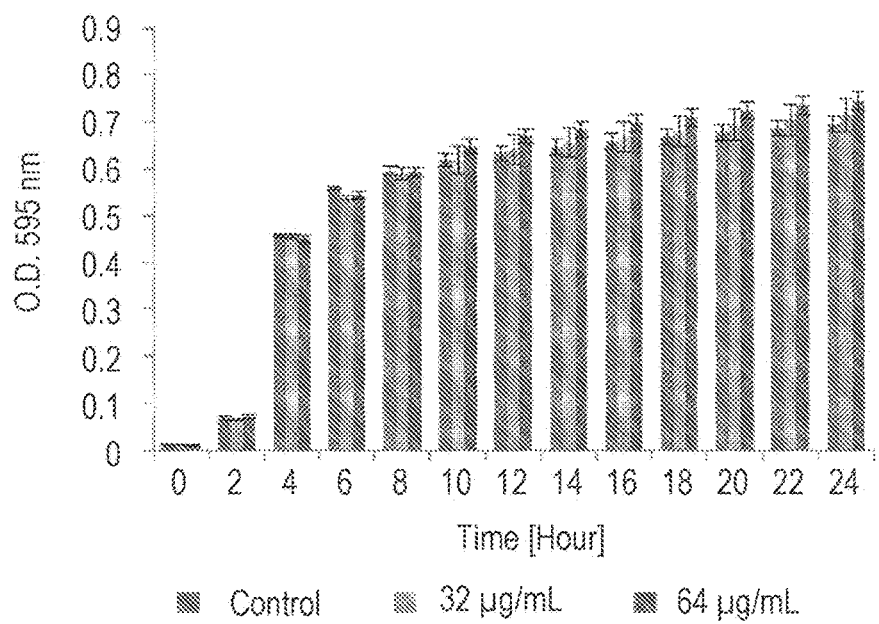
FIGS. 5A-5D show growth curves of bacteria in the presence of compound 27: (5A) *E. coli* ATCC 25922, (5B) *P. aeruginosa* PAO1, (5C) *E. faecalis* ATCC 29212, and (5D) *S. aureus* subsp. *aureus* Rosenbach ATCC 33592. Bacteria were incubated with compound 27 (32 and 64 µg/mL) for 24 h at 37° C. Pillar[6]arene conjugate 27 did not inhibit the growth of these bacteria.
Figure 5B:
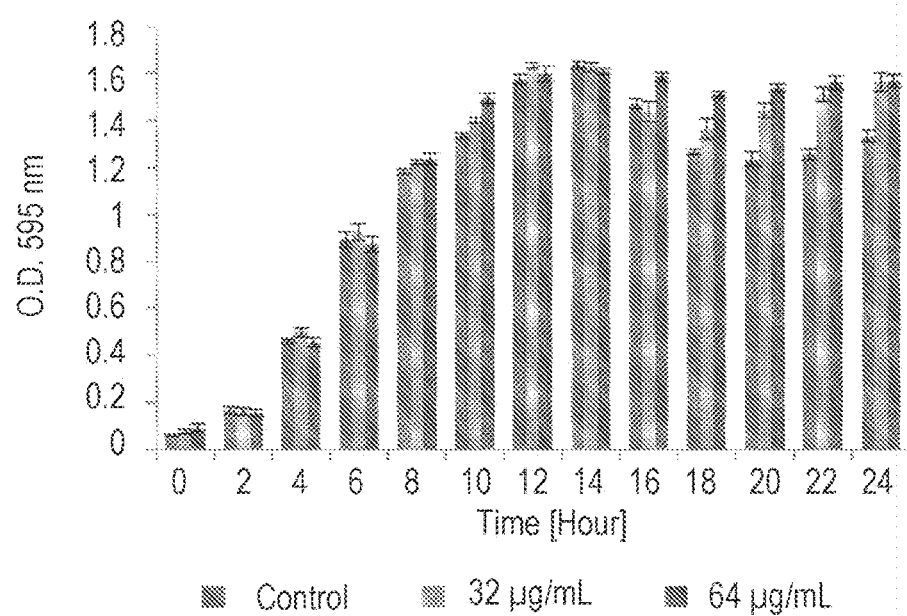
Figure 5C:
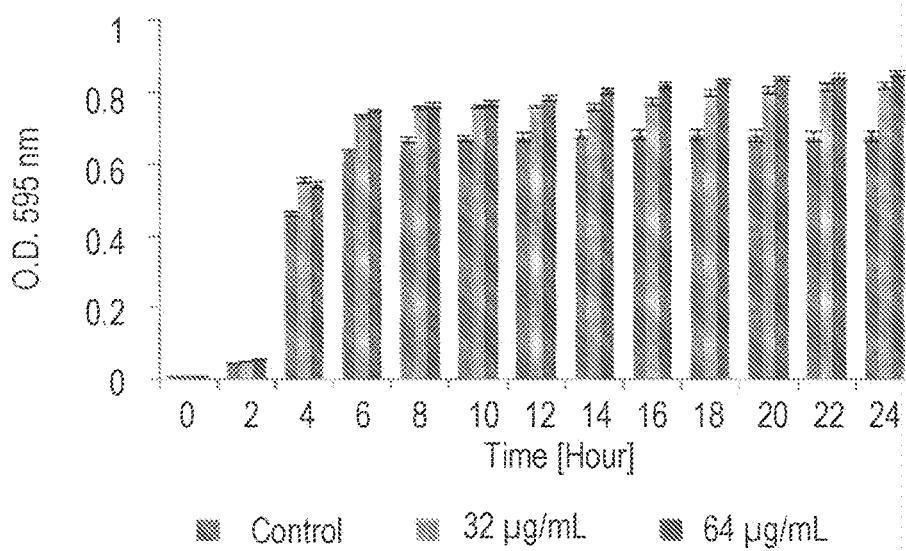
Figure 5D:
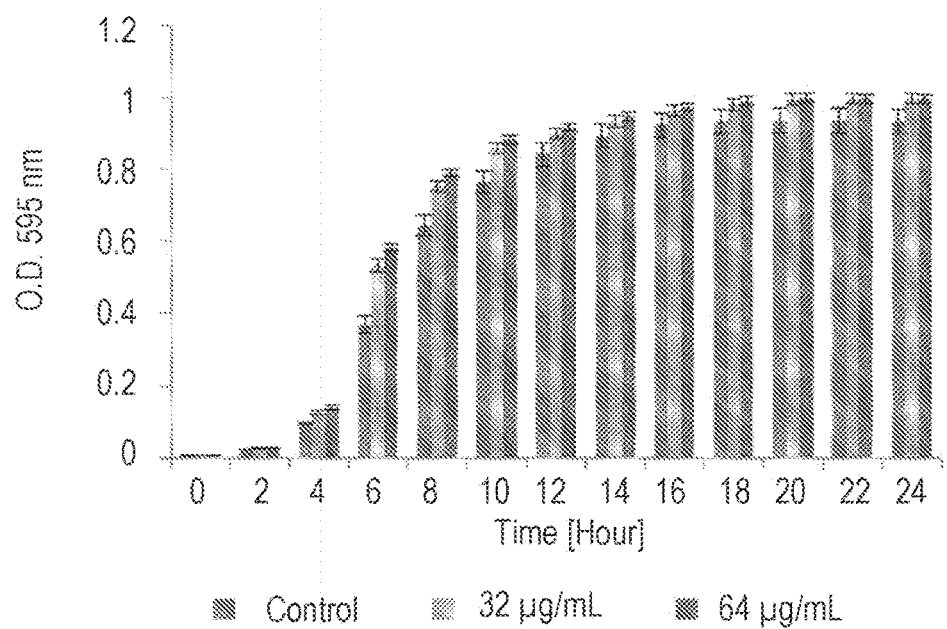

Pillararenes 21 and 27, the most potent inhibitors of biofilm formation, did not eradicate mature biofilms. In addition, we determined the $MBIC_{50}$ of compound 27, which demonstrated potent biofilm inhibition properties, against *S. aureus* subsp. *aureus* Rosenbach ATCC 33592, and *E. faecalis* in cultures that were 2-fold, 4-fold, and 10-fold the standard inoculum (OD=0.001). No significant change in $MBIC_{50}$ values was observed indicating that there is no significant inoculum effect for this compound (FIG. 4; Table 2).

TABLE 2

Effect of initial inoculum on $MBIC_{50}$ values of compound 27

| Bacteria strain | Initial inoculum ($OD_{600}$) | $MBIC_{50}$ [μM] |
|---|---|---|
| *S. aureus* subsp. *aureus* Rosenbach ATCC 33592 | 0.025 | 0.37 |
|  | 0.05 | 0.37 |
|  | 0.1 | 0.37 |
| *E. faecalis* (ATCC 29212) | 0.025 | 0.37 |
|  | 0.05 | 0.73 |
|  | 0.1 | 0.73 |

Since all of the pillararenes in this study are cationic amphiphiles, we evaluated the antimicrobial activity of the most potent inhibitor of biofilm formation pillar[6]arene 27 to determine whether the capability to inhibit biofilm formation results from bactericidal activity. Minimal inhibitory concentration (MIC) experiments were performed following the double-dilution protocol (Wiegand et al., 2008; Berkov-Zrihen et al., 2013).

The MIC values against the examined Gram-positive strains were higher than ~47 μM, at least 16-fold higher than the highest MBIC50 value measured for pillar[6]arene 27 against the tested strains. We therefore concluded that the observed inhibition of biofilm formation did not result from a bactericidal effect. The possibility that pillar[6]arene 27 had a bacteriostatic effect was examined by comparing the growth curves of two of Gram-negative strains (*E. coli* ATCC 29522 and *P. Aeruginosa* PAO1) and two Gram-positive strains (*S. aureus* subsp. *aureus* Rosenbach ATCC 33592 and *E. faecalis* ATCC 29212) in the absence and in the presence of 32 and 64 μg/ml of 27 for 24 hours. These concentrations are ~15 and ~30-fold higher than the MBIC50 values measured for this compound against the two Gram-positive strains. The growth curves clearly indicated that, at a concentration significantly higher than the MBIC50, this compound had no effect on bacterial growth (FIG. 5). Thus, the anti-Gram-positive biofilm properties of this compound do not result from a bacteriostatic effect.

Figure 6A:
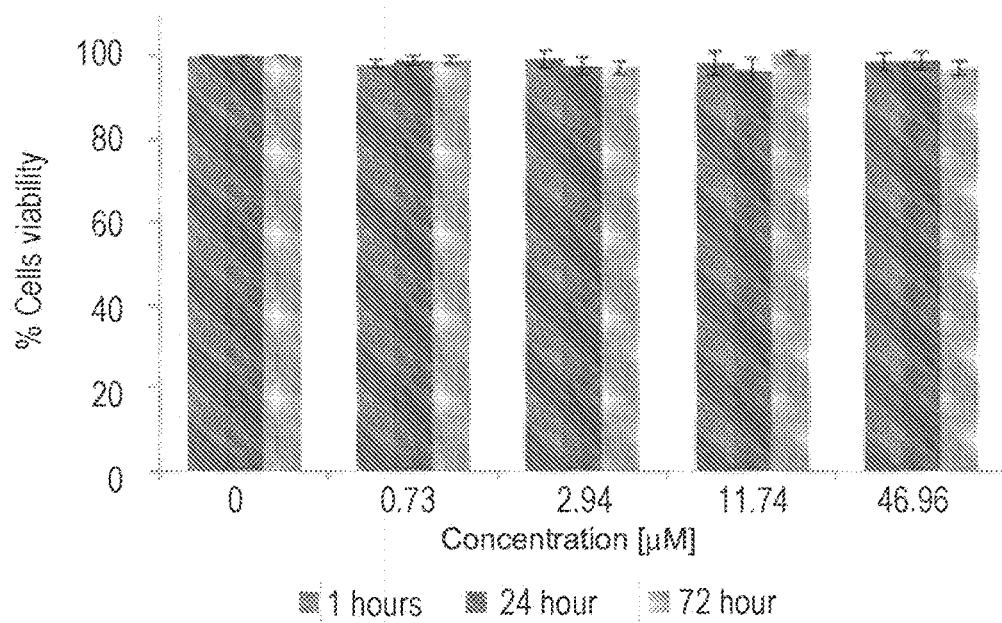
FIGS. 6A-6B show the effect of compound 27 on the viability of IB3-1 cells (6A); and THP-1 cells (6B).
Figure 6B:
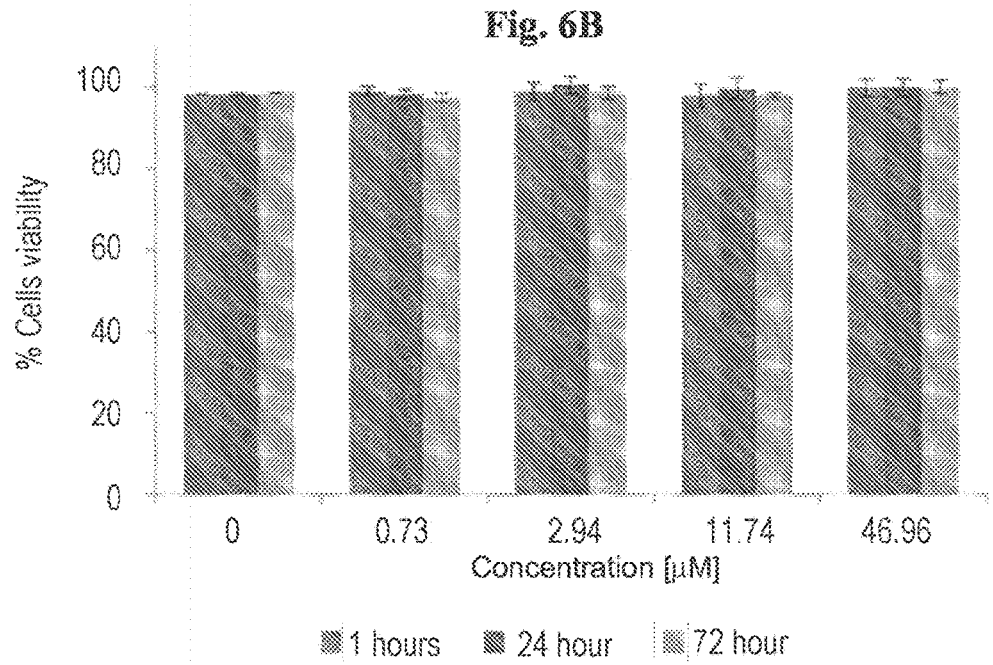
Figure 7:
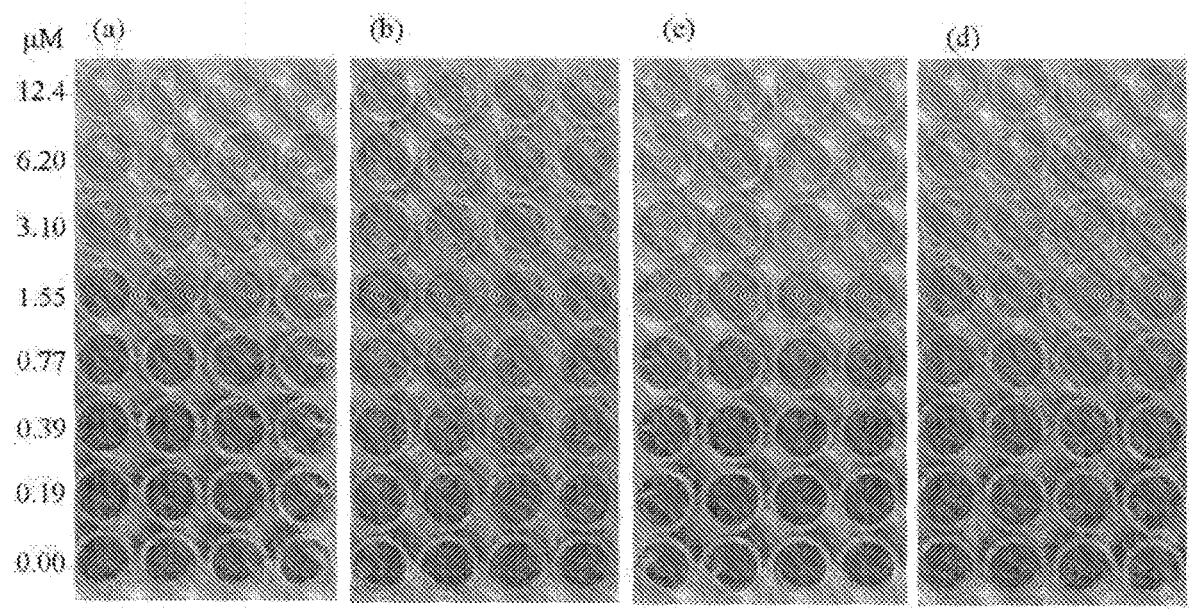
FIG. 7 shows biofilms of *S. aureus* subsp. *aureus* Rosenbach ATCC 33592 in the presence of increasing concentrations (µM) of pillar[5]arene derivatives (a) compound 29, (b) compound 30, (c) compound 25, and (d) compound 28 stained with crystal violet.
Figure 8:
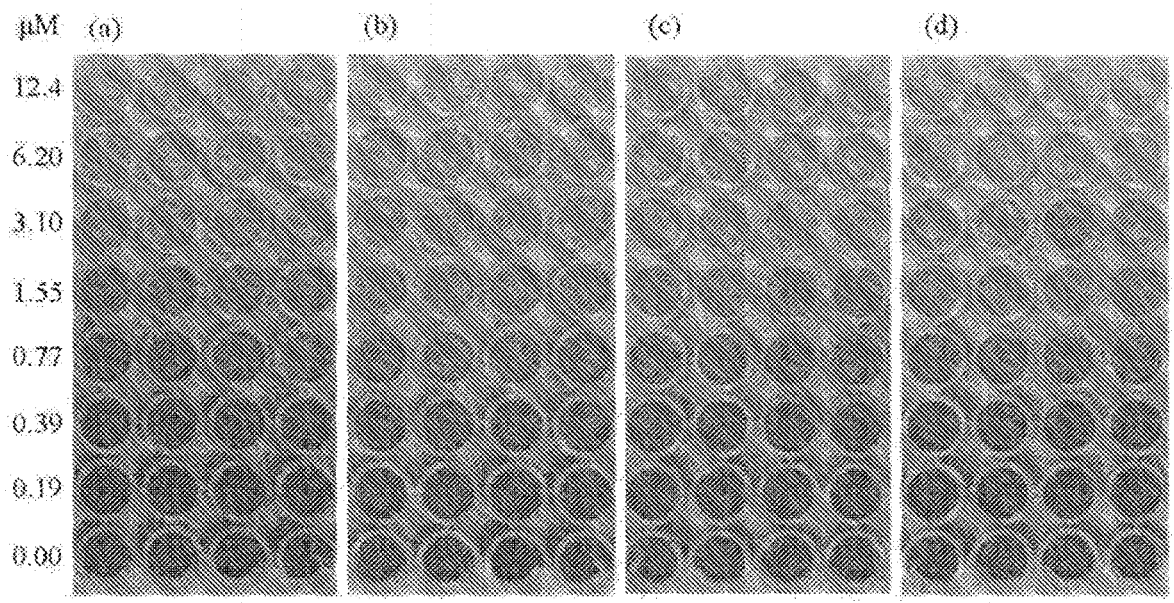
FIG. 8 shows biofilms formed by *E. faecalis* ATCC 29212 in the presence of increasing concentrations (µM) of pillar [5]arene derivatives (a) compound 29, (b) compound 30, (c) compound 25, and (d) compound 28 stained with crystal violet.
Figure 9:
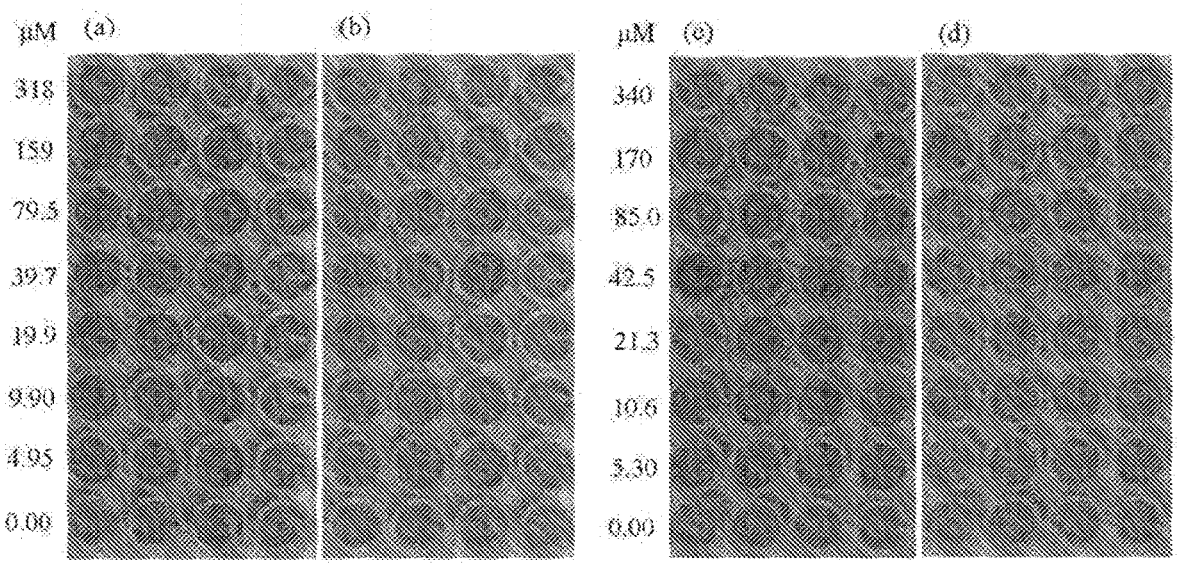
FIG. 9 shows biofilms formed by *S. aureus* subsp. *aureus* Rosenbach ATCC 33592 in the presence of increasing concentrations of (a) compound 12 and (c) compound 11. Biofilms formed by *E. faecalis* ATCC 29212 in the presence of increasing concentrations of (b) compound 12 and (d) compound 11. All the wells were stained with crystal violet.
Figure 10A:
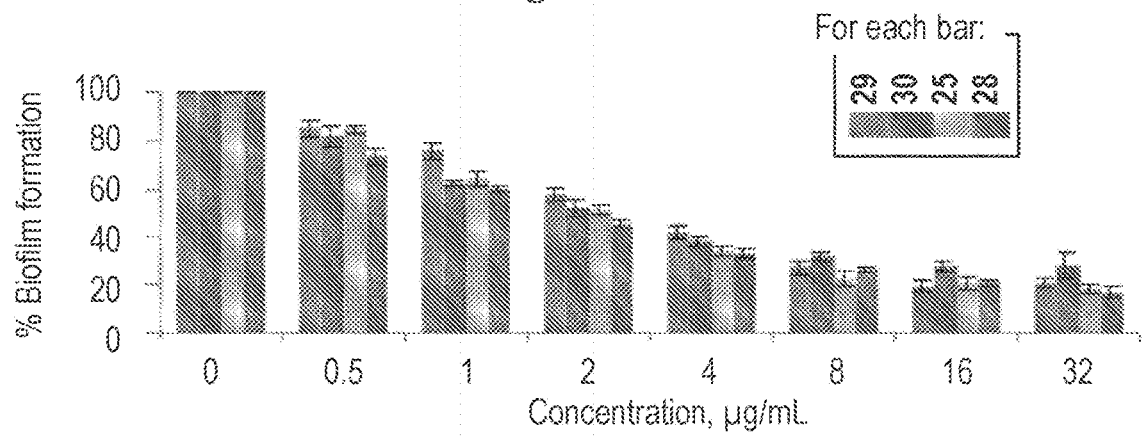
FIGS. 10A-10C show biofilm formation by *S. aureus* ATCC 33592 (MRSA) (10A) and *E. faecalis* ATCC 29212 (10B) evaluated using the double-dilution method with starter inoculum of 1:100 (OD600=0.01) in the presence of compounds 25 and 28-30; and biofilm formation in the presence of compounds 11 and 12 (10C) Concentration ranges of the tested compounds were: (25) 0.21-13.27; (28) 0.18-11.30; (29) 0.19-12.40; (30) 0.17-10.66; (11) 5.3-340 µM; and (12) 4.95-317.
Figure 10B:
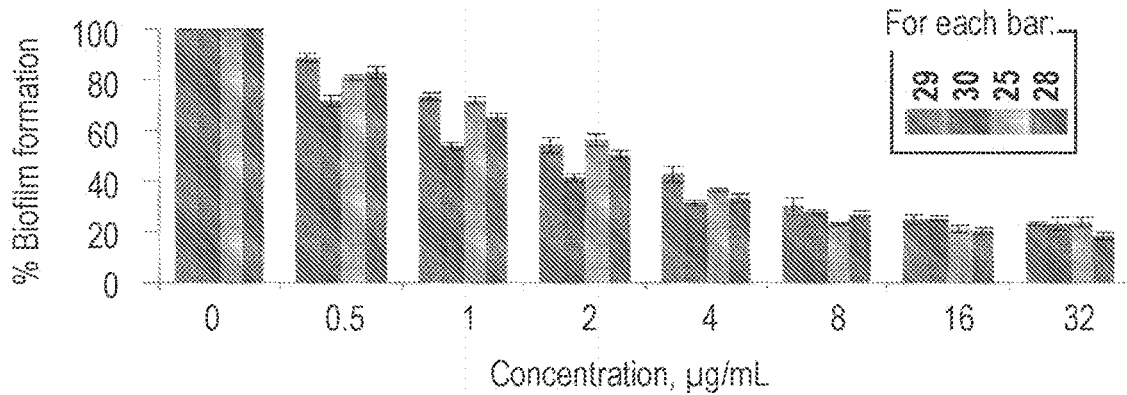
Figure 10C:
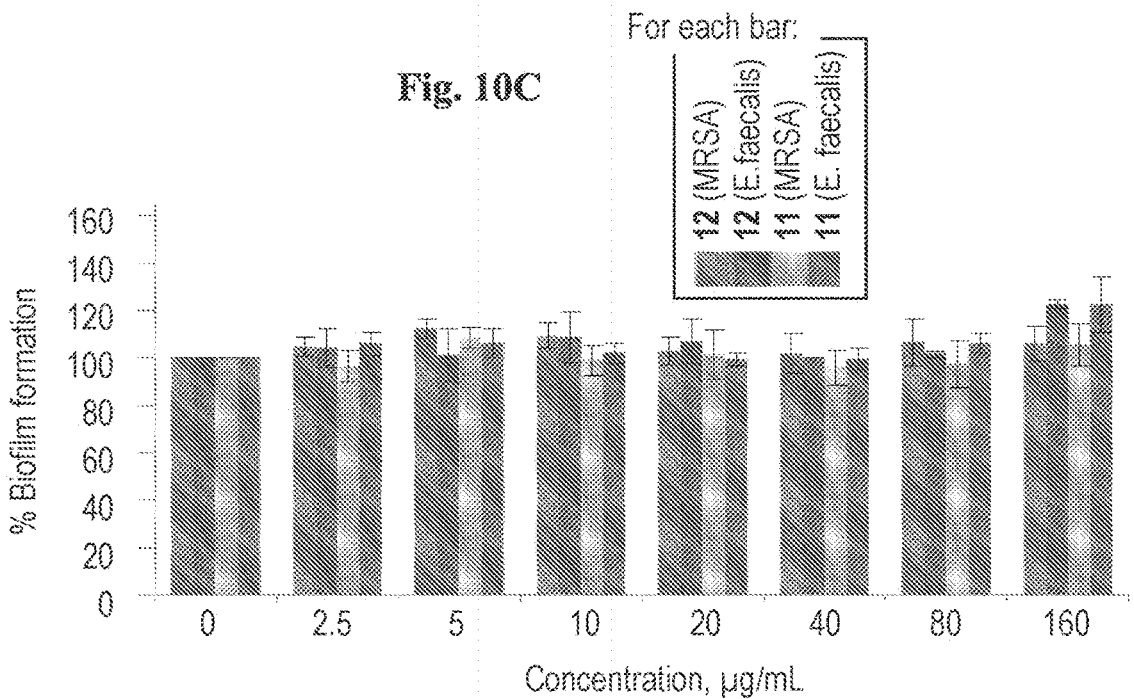

Finally, many families of antimicrobial cationic amphiphiles disrupt mammalian cell membranes as well as bacterial cell membranes (Berkov-Zrihen et al., 2015; Benhamou et al., 2015). Rat red blood cells serve as a standard model for the evaluation of the ability of compounds to lyse mammalian cell membranes. Up to a concentration of 94 μM, none of the cationic pillararenes caused any measurable hemolysis of red blood cells obtained from laboratory rats following a previously reported protocol (Benhamou et al., 2015). The toxicity of compound 27 toward human monocytic THP1 cells (ATCC TIB 202) and cystic fibrosis human bronchial epithelial cells IB3-1 (ATCC CRL-2777) was also evaluated. No effects on viability were observed after 72-hour incubation with concentrations up to 46.96 μM, about 50 times the MBIC50 values measured for this compound against the two Gram-positive strains (FIG. 6).

Study 2. Phosphonium Pillar[5]Arenes Inhibit Bacterial Biofilm Formation

In the present study, we prepared a series of phosphonium and ammonium decorated pillar[5]arenes (25, 28-30) and their respective monomers (11 and 12) and studied their anti-biofilm activity with the aim of evaluating the effect of the nature of the positive charges; the cooperativity of the overall positive charges; and the pillar[n]arene platform on the observed anti-biofilm activity.

The water-soluble cationic pillar[5]arene derivatives used in this study were synthesized by a four-step process (Scheme 3). Briefly, in the first step commercially available hydroquinone was alkylated with 1,3-dibromopropane using potassium carbonate in acetone to afford the monomer 8a. The functionalized pillar[5]arene 9a was obtained by the cyclization of monomer 8a with paraformaldehyde and boron trifluoride diethyletherate in dichloroethane. Reaction of 9a with an excess of trimethylamine or trimethylamine in ethanol under reflux gave the water-soluble pillar[5]arene derivatives 25 or 28, respectively, and a similar procedure was followed to obtain compounds 29 and 30, by reaction with excess of trimethylphosphine or triethylphosphine, respectively (Scheme 4). The control monomers 11 and 12 were synthesized by reacting 8a with excess trimethylphosphine and trimethylamine, respectively. All the compounds were characterized by $^1H$ and $^{13}C$ NMR and high-resolution mass spectroscopy (HRMS).

The effects of compounds 25 and 28-30 were evaluated on biofilm formation by two clinically important Gram-positive bacterial strains, S. aureus ATCC 33592 and Enterococcus faecalis ATCC 29212. Inhibition of biofilm formation was determined using the crystal violet staining assay (Feldman et al., 2012). The minimal concentration at which at least 50% reduction in biofilm formation compared to untreated cells ($MBIC_{50}$) was determined, and the results are summarized in Table 3. The dose responses are presented in FIGS. 7-10.

All the cationic pillar[5]arene derivatives exhibited potent inhibition of biofilm formation against the two tested Gram-positive pathogens. The $MBIC_{50}$ values of the deca-ammonium pillar[5]arene analogues 25 and 28 were found to be in the range of 0.71-1.66 µM for both of the tested strains. The corresponding deca-phosphonium pillar[5]arenes 29 and 30 showed a similar range of $MBIC_{50}$ values, 0.67-1.55 µM. These results indicate that replacement of the ammonium cations by phosphonium cations does not significantly affect the inhibition of biofilm formation by cationic pillararenes. Thus, the positive charges are essential for the observed anti-biofilm activity; however, the nature of the charges has a marginal effect. In this respect, Study 1 shows that a negatively charged deca-carboxylate derivative of pillar[5]arene does not significantly inhibit biofilm formation.

TABLE 3

The anti-biofilm activity ($MBIC_{50}$) of pillar[5]arene derivatives 25 and 28-30*

| | $MBIC_{50}$ in µM (µg/mL) | |
|---|---|---|
| Compound | S. aureus ATCC 33592 | E. faecalis ATCC 29212 |
| 25 | 1.66 (4) | 1.66 (4) |
| 28 | 0.71 (2) | 1.41 (4) |
| 29 | 1.55 (4) | 1.55 (4) |
| 30 | 1.33 (4) | 0.67 (2) |
| 11 | >340 (160) | >340 (160) |
| 12 | >317 (160) | >317 (160) |

*Compounds were evaluated using the double-dilution method. Each value is the mean of at least three independent experiments that included five replicates at each concentration.

To evaluate the effect of hydrophobicity on the biofilm inhibition activity, we compared compounds 28 and 30, in which the ammonium or phosphonium cations are attached to triethyl moieties, to compounds 25 and 29, which carry trimethyl moieties. Despite the fact that compounds 28 and 30 have 30 more carbon atoms than do compounds 25 and 29, their $MBIC_{50}$ values did not significantly differ (Table 3, FIGS. 7A-7B). In addition, we found that the dose response for the tested pillar[5]arene derivatives 25 and 28-30 (FIGS. 7A-7B) were also very similar, further corroborating the fact that pillararenes 28 and 30 are as effective as 25 and 29 in preventing biofilm formation by the two tested strains.

To understand the cumulative effect of the positive charges and the advantage of clustering these charges on a pillararene scaffold, we synthesized the monomers 11 and 12, which correspond to the repeating units of pillar[5]arenes 25 and 29, respectively. Compounds 11 and 12 were also tested for their biofilm inhibition properties towards the two bacterial strains. Monomers 11 and 12 were tested at ~5-fold higher concentrations than were compounds 25 and 28-30 such that the numbers of charges and ionic strengths of the tested solutions were comparable. Up to 340 µM of 11 and 317 µM of 12 (160 µg/mL of 11 and 12), neither 11 nor 12 caused a measurable inhibition of biofilm formation (FIG. 7C), suggesting that in these anti-biofilm agents the cumulative charge organization on the pillar[5]arene scaffold is a crucial factor for the observed activity.

Many cationic amphiphiles act as antimicrobial agents that kill bacteria (Kanazawa et al., 1993 and 1994; Cieniecka-Roslonkiewicz et al., 2005; Kurata et al., 2011; Xue et al., 2015). Therefore, to evaluate whether the inhibiting effect of compounds 25 and 28-30 on biofilm formation originated from a possible antimicrobial activity of these compounds we measured the minimal inhibitory concentrations (MICs) against the tested strains. The MIC values for compounds 25 and 28-30 were found to be 27, 23, 25 and 21 µM, respectively, more than 16 fold higher than the highest $MBIC_{50}$ values measured for these compounds against the two tested strains. These results demonstrate that the inhibition of biofilm formation by the phosphonium-decorated pillararenes 29 and 30 did not originate from antibacterial activity.

Figure 11A:
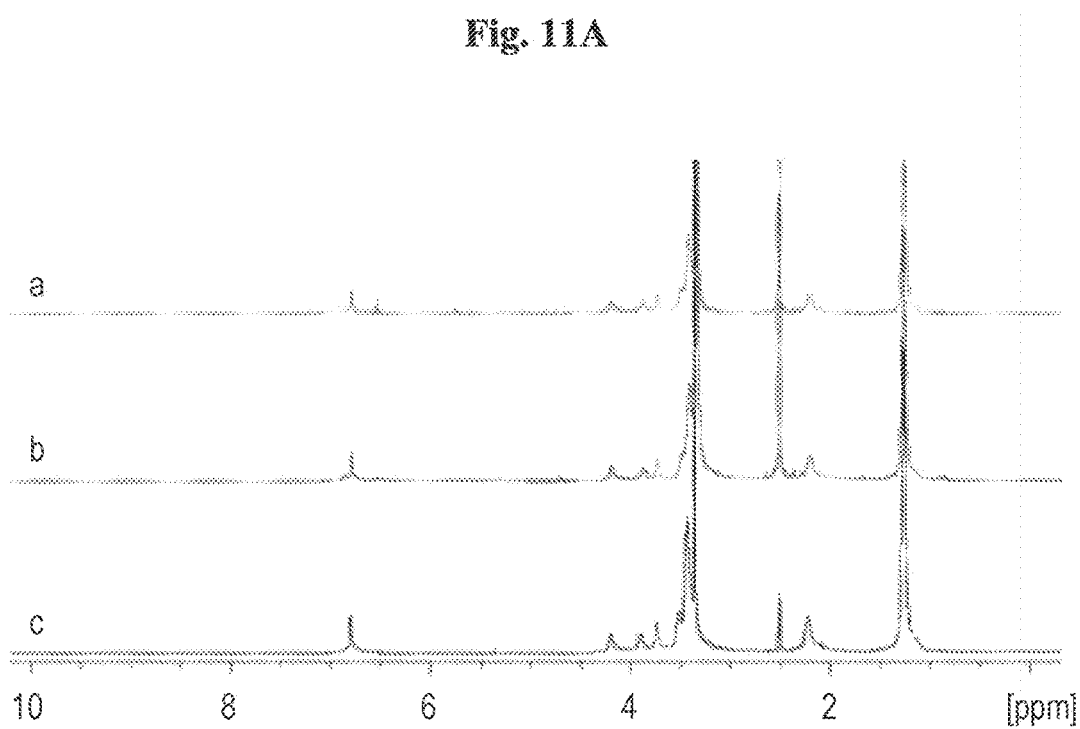
FIGS. 11A-11B show $^1$H NMR spectra of compound 28 after incubation pH (a) 7.4, (b) 2.3, and (c) 10.2 for 4 hours (11A); and $^1$H NMR spectra of compound 30 after incubation at pH (a) 7.4, (b) 2.3, and (c) 10.7 for 4 hours (11B).
Figure 11B:
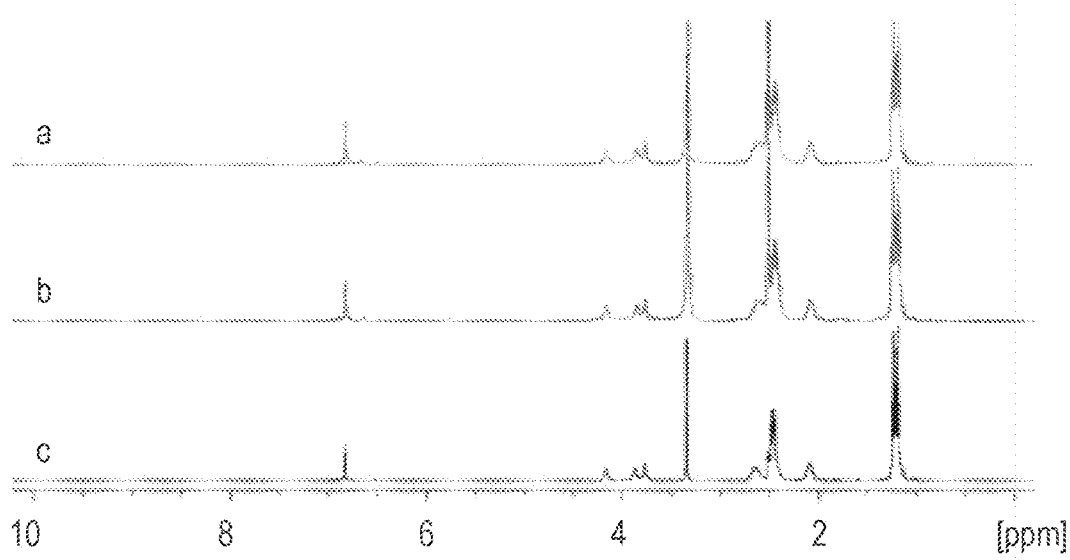
Figure 12A:
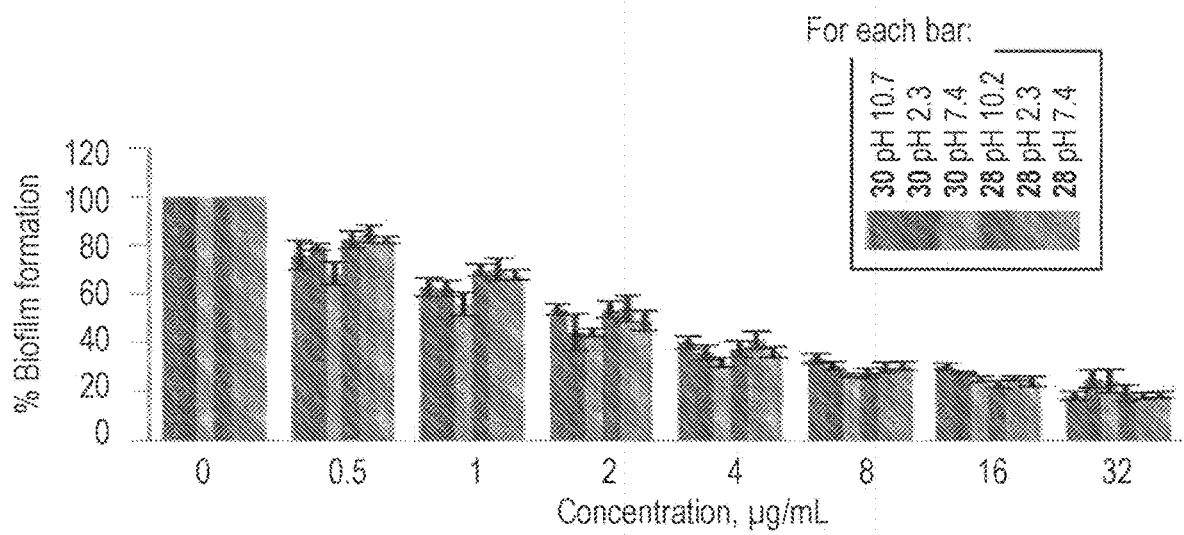
FIGS. 12A-12B show biofilm formation by *S. aureus* subsp. *aureus* Rosenbach ATCC 33592 (12A) and *E. faecalis* ATCC 29212 (12B) in the presence of increasing concentrations (µM) 28 and 30 that had been incubated for 4 hours at different pH levels.
Figure 12B:
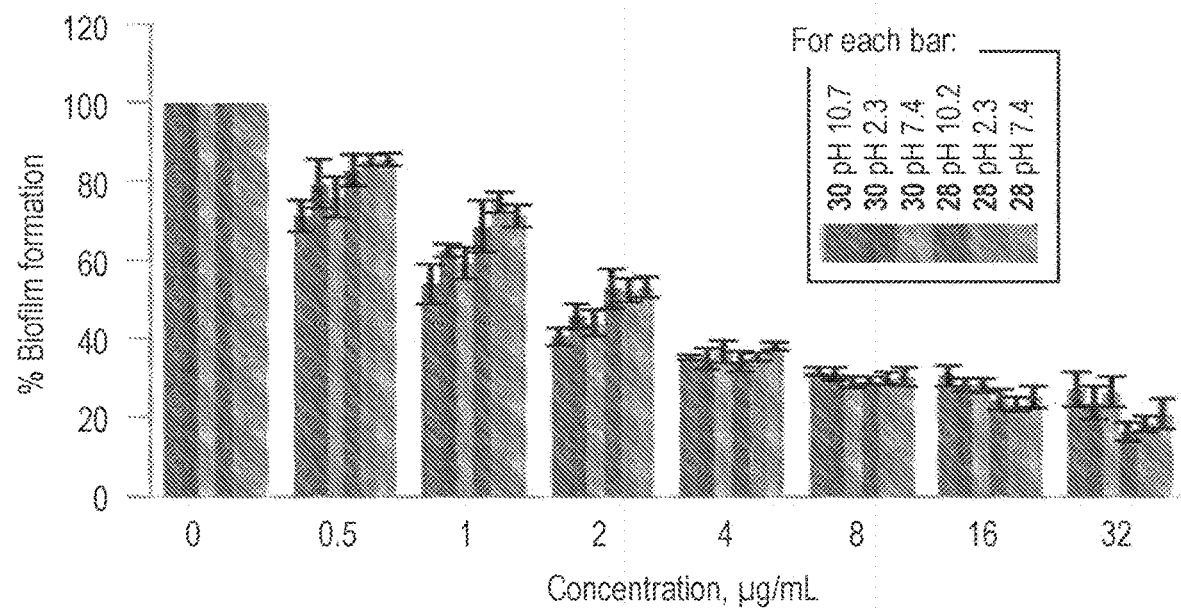

The stability of a bioactive compound may affect the molecule performance. To address this issue the stability of the new phosphonium and ammonium pillar[5]arene derivatives was evaluated by incubation for 4 hours in solutions at different pH values. Thereafter the materials were freeze dried, inspected by $^1$H-NMR and tested for their biofilm inhibition properties. No significant decomposition was observed in the $^1$H-NMR spectra recorded after exposure to acidic or alkaline pH (FIG. 11). More importantly, the anti-biofilm activities of compounds 28 and 30 remained unchanged after these exposures as seen in Table 4 and FIG. 12.

TABLE 4

Biofilm inhibitory activity against Gram positive strains of compounds 20 and 22 after incubation at different pH levels for 4 hours

| | | $MBIC_{50}$ in µM (µg/mL) | |
|---|---|---|---|
| Compound | pH | S. aureus subsp. aureus Rosenbach ATCC 33592 | E. faecalis ATCC 29212 |
| 28 | 2.3 | 1.41 (4) | 1.41 (4) |
| | 7.4 | 1.41 (4) | 1.41 (4) |
| | 10.7 | 1.41 (4) | 1.41 (4) |
| 30 | 2.3 | 0.67 (2) | 1.33 (4) |
| | 7.4 | 0.67 (2) | 1.33 (4)) |
| | 10.2 | 1.33 (4) | 0.67 (2) |

Figure 13A:
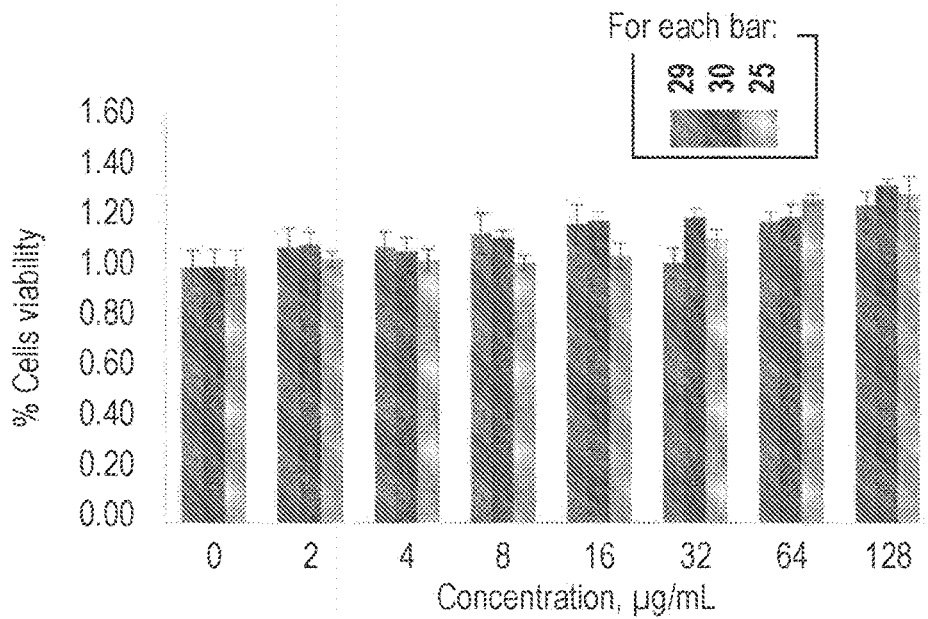
FIGS. 13A-13B show the cell toxicity of compounds 25, 29 and 30 on mammalian IB3-1 cell-line (13A) and HaCaT cell-line (13B).
Figure 13B:
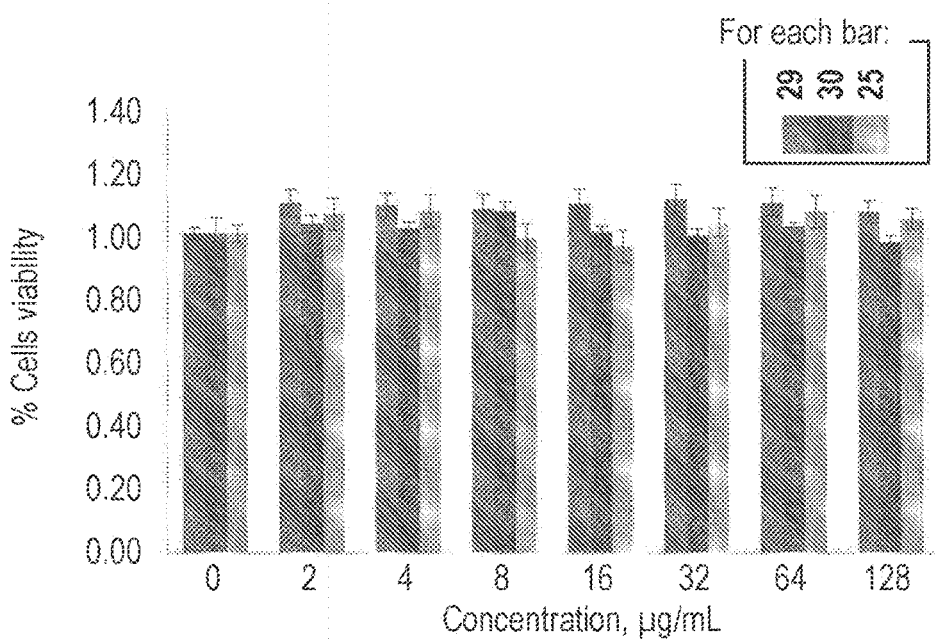

Finally, it is well established that many cationic amphiphiles disrupt mammalian cell membranes, which limits potential for clinical utility (Jennings et al., 2014). We therefore determined the haemolytic effect of pillar[5]arenes 29 and 30 on rat RBCs. Up to a concentration of 85 µM, none of the phosphonium-decorated pillar[5]arenes caused measurable haemolysis of RBCs. In addition, compounds 25, 29 and 30 were found to have no effect on mammalian cell viability up to a concentration of 128 µg/mL as shown in FIG. 13.

Study 3. Ammonium Pillar[5-6]Arenes Inhibit Bacterial Biofilm Formation

In this study, several ammonium pillar[5-6]arene derivatives other than those exemplified in Studies 1-2 were synthesized, utilizing chemical procedures similar to those exemplified above, and their biofilm inhibition activity was tested as described in the Studies above, using *S. aureus* ATCC 33592 (MRSA) and *E. faecalis* ATCC 29212.

The ammonium pillar[5-6]arene derivatives prepared are compounds 31, 32 and 33 and are shown in Scheme 4. Compound 31 is an ammonium pillar[5]arene derivative similar to compound 25, wherein the spacer represented by each one of the groups $R_4$ and $R_5$ in the formula I is —$(CH_2)_6$— rather than —$(CH_2)_3$— as in compound 25; compound 32 is an ammonium pillar[6]arene derivative similar to compound 27, wherein the spacer represented by each one of the groups $R_4$ and $R_5$ in the formula I is —$(CH_2)_3$— rather than —$(CH_2)_2$— as in compound 27; and compound 33 is an ammonium pillar[6]arene derivative similar to compound 27, wherein the cation represented by the group Y in the formula I is 1-methyl-imidazolium-3-yl rather than —$N^+(CH_3)_3$ as in compound 27.

The biofilm inhibition activity of each one of these compounds is shown in Table 5. Interestingly, the non-symmetric ammonium pillar[5]arene derivatives 34 and 35 (Table 5) were found to have biofilm inhibition activity that is remarkably lower than those of the cationic pillar[5-6]arene derivatives of the formula I exemplified in each one of the Studies herein, indicating that the presence of cationic groups in both sides of the compound, and possibly also a symmetric structure, are necessary for enabling the biofilm inhibition activity.

TABLE 5

The anti-biofilm activity ($MBIC_{50}$) of pillar[5-6]arene derivatives 31-33

| | $MBIC_{50}$ in µM (µg/mL) | |
|---|---|---|
| Compound | MRSA | *E. faecalis* |
| 31 | 0.4 | 0.4 |
| 32 | 0.7 | 0.7 |
| 33 | 0.7 | 0.7 |
| 34 | 8.6 | 8.6 |
| 35 | >15 | >15 |

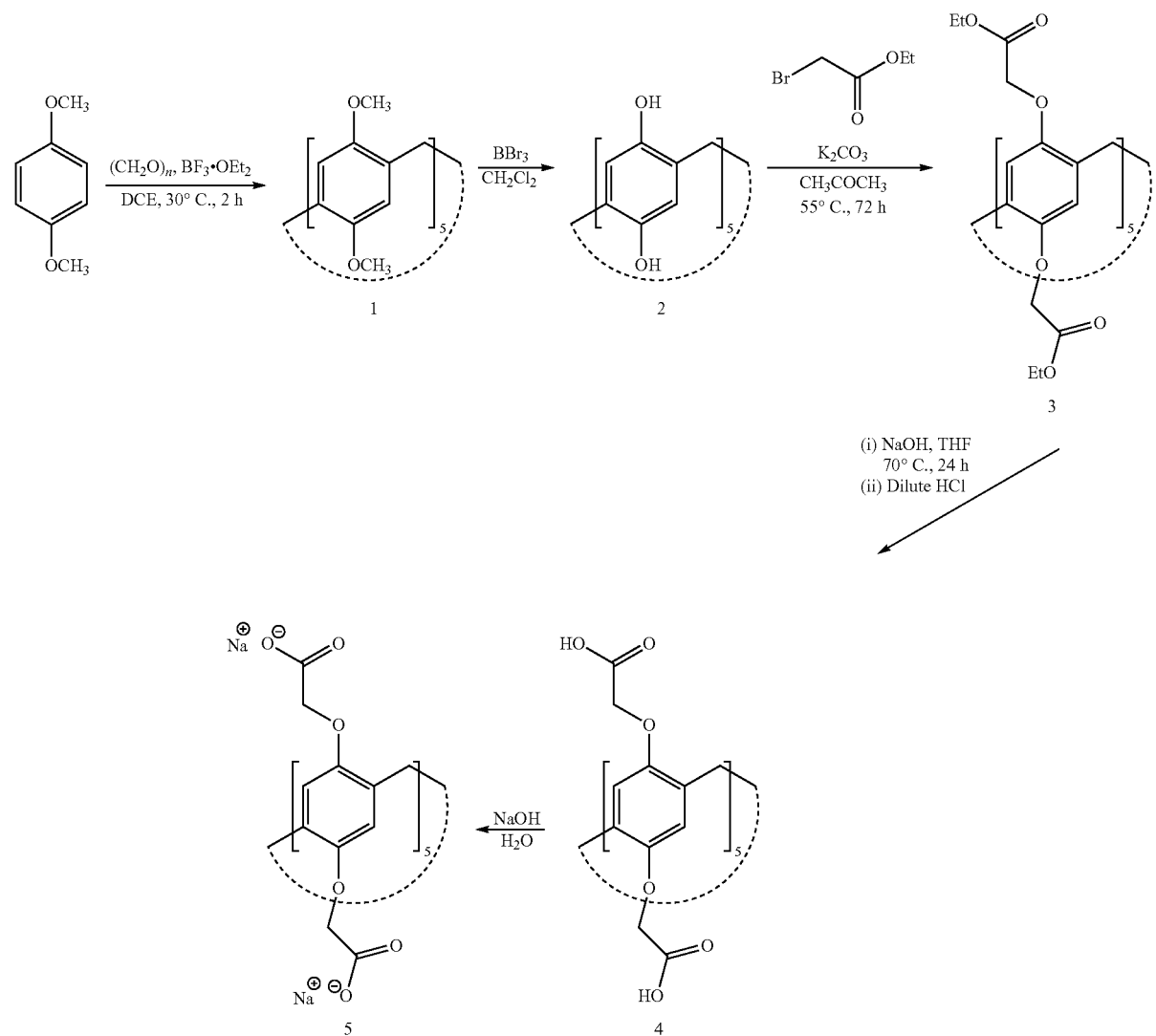

Scheme 1. Synthesis of compounds 5, 21 and 22

-continued
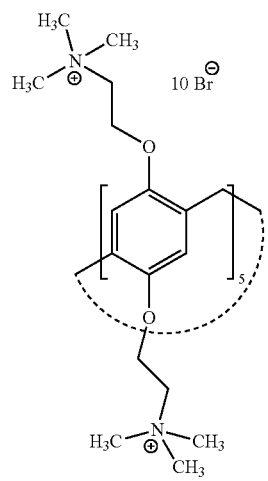
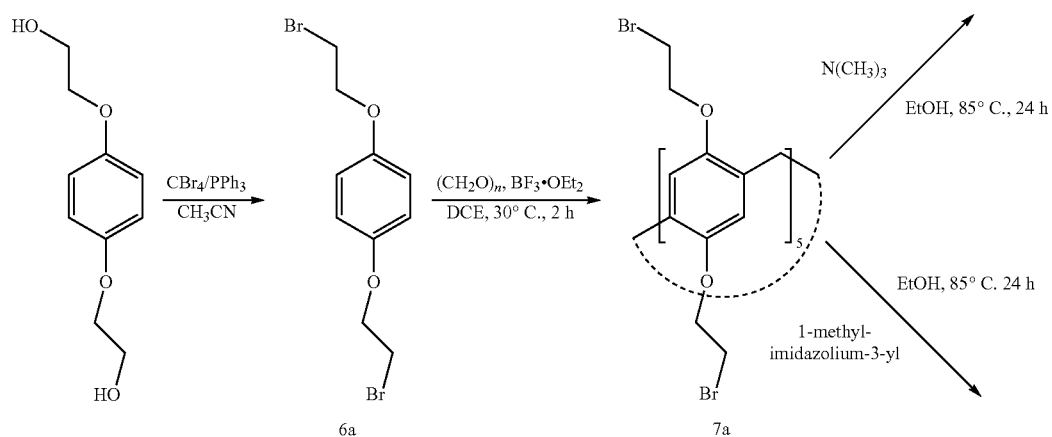
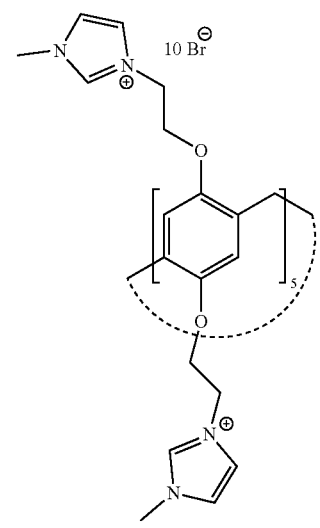

Scheme 2. Synthesis of compounds 23-27
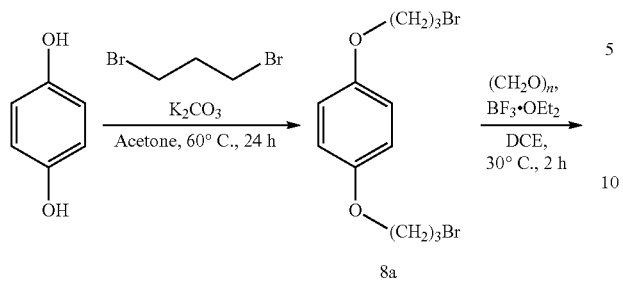
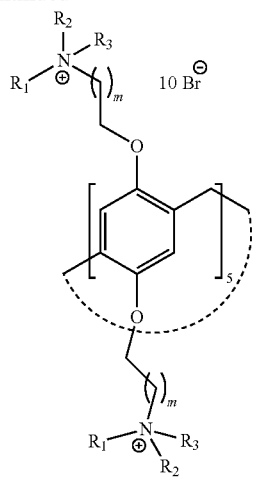
23: m = 1; $R_1 = R_2 = R_3 = CH_2CH_3$
24: m = 1; $R_1 = R_2 = CH_3$; $R_3 = (CH_2CH_2OH)$
25: m = 2; $R_1 = R_2 = R_3 = CH_3$
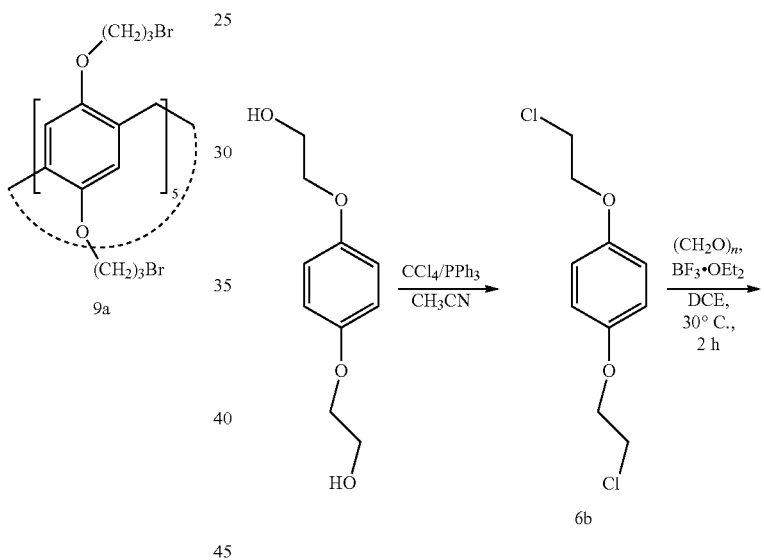
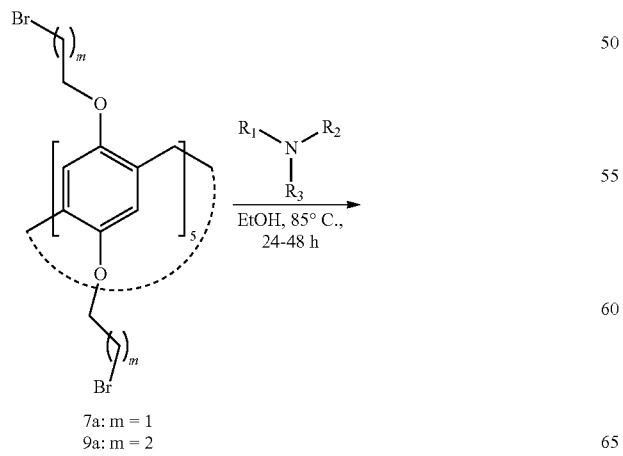
7a: m = 1
9a: m = 2
7b

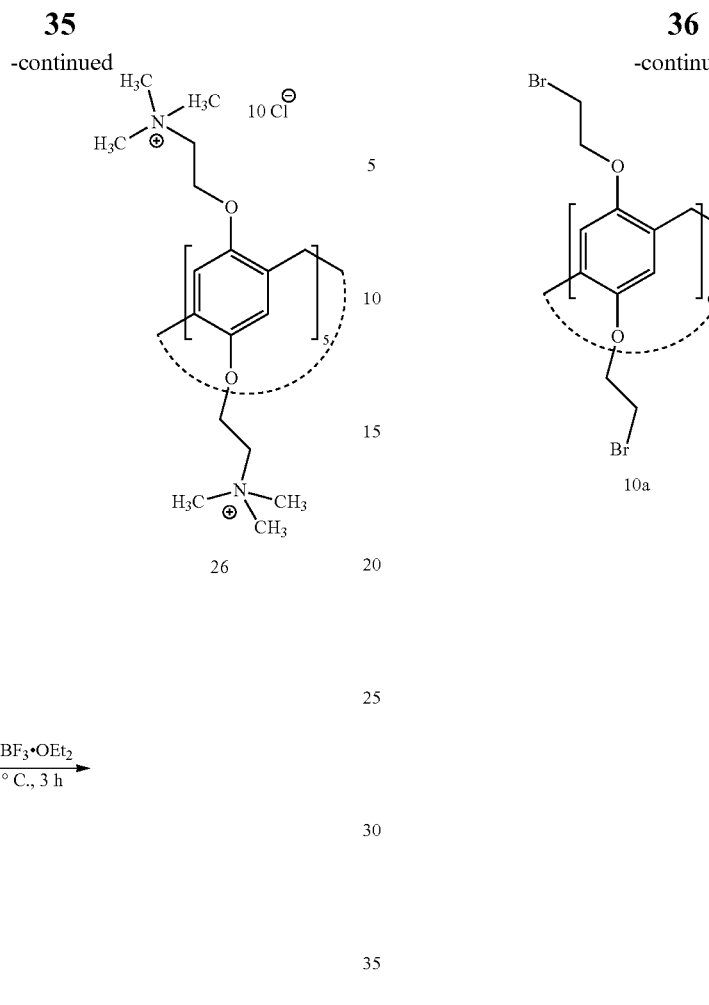
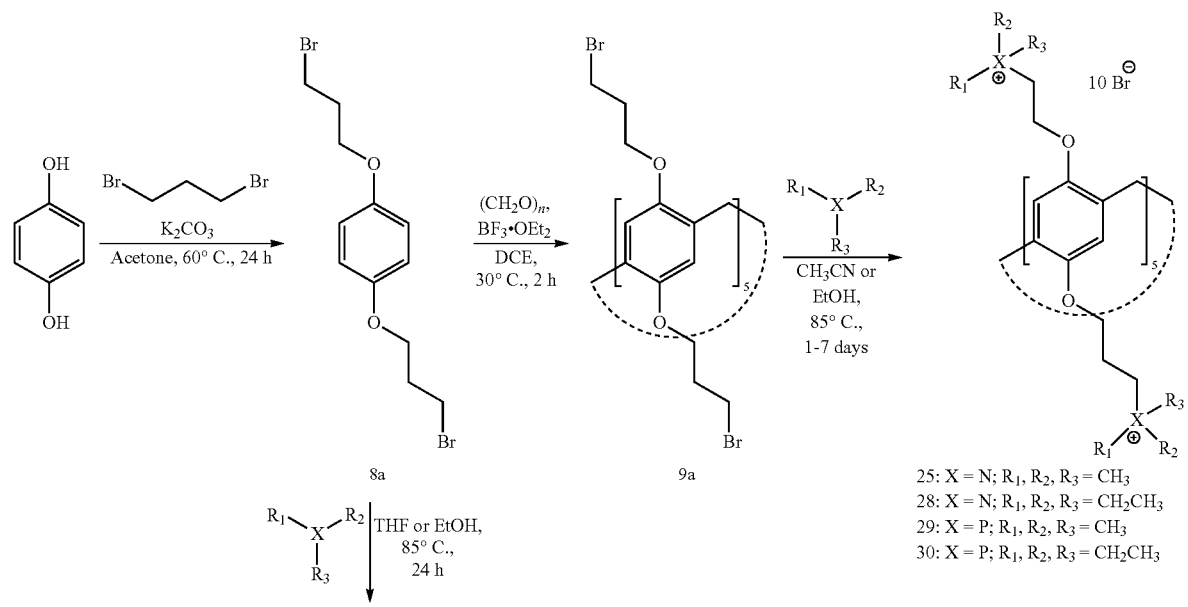
Scheme 3. Synthesis of compounds 11-12, 25 and 28-30
25: X = N; R₁, R₂, R₃ = CH₃
28: X = N; R₁, R₂, R₃ = CH₂CH₃
29: X = P; R₁, R₂, R₃ = CH₃
30: X = P; R₁, R₂, R₃ = CH₂CH₃

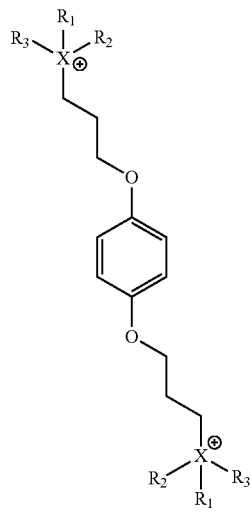
11: X = N; R₁, R₂, R₃ = CH₃
12: X = P; R₁, R₂, R₃ = CH₃
Scheme 4. Cationic pillar[5-6]arene derivatives synthesized and tested in Studies 1-3
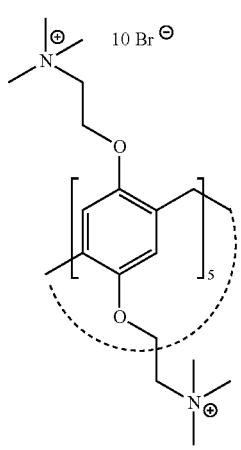
21
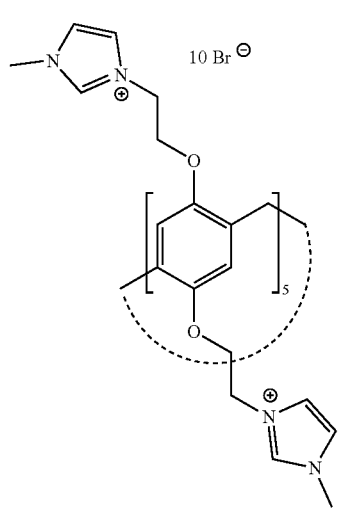
22
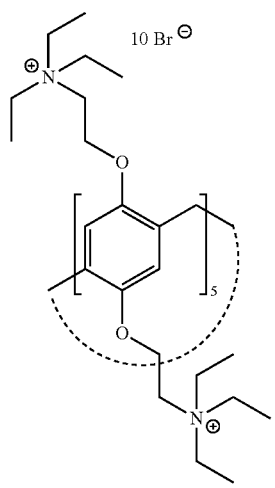
23
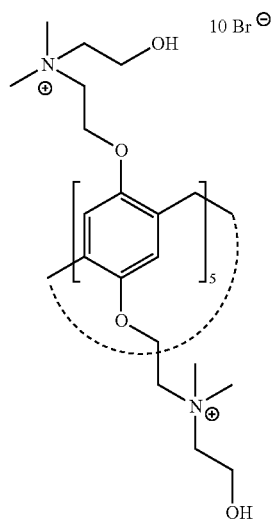
24

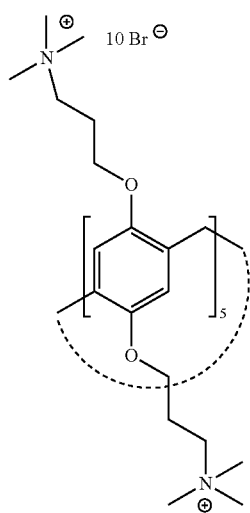
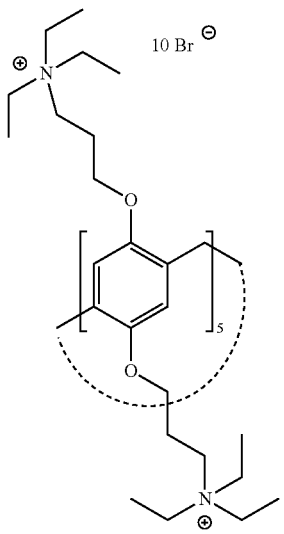
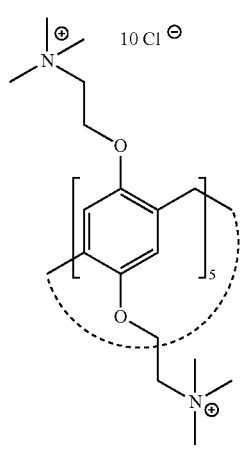
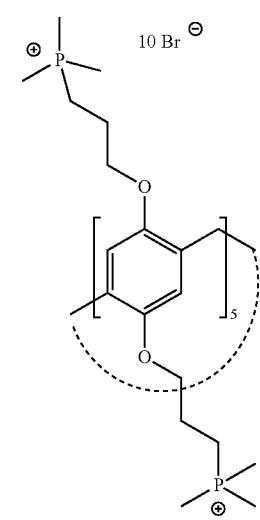
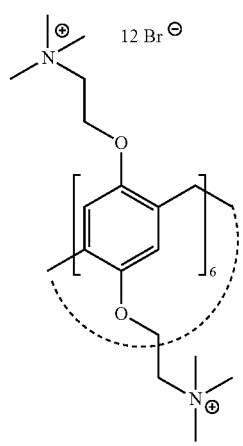
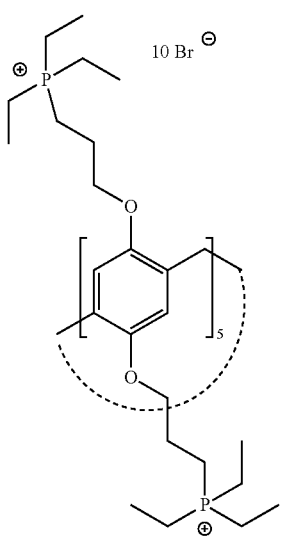

31

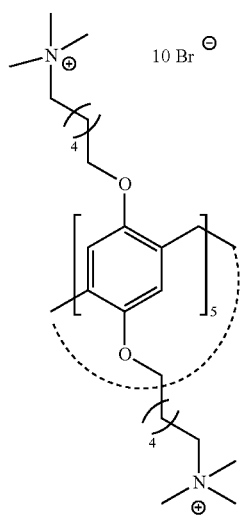

32

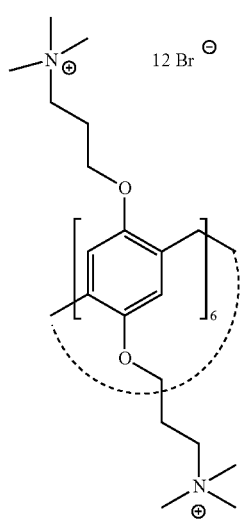

33

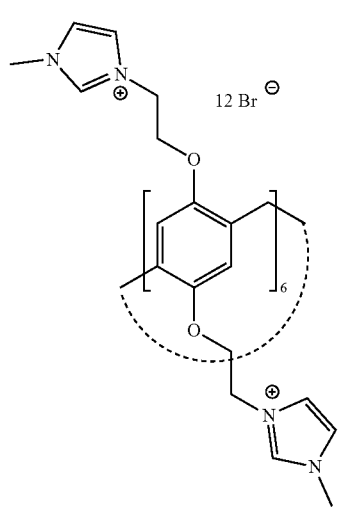

34

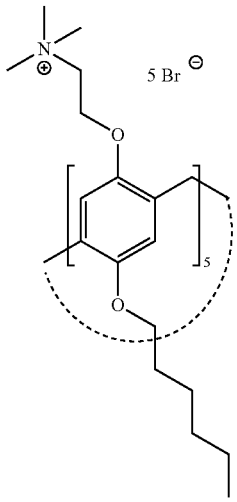

35

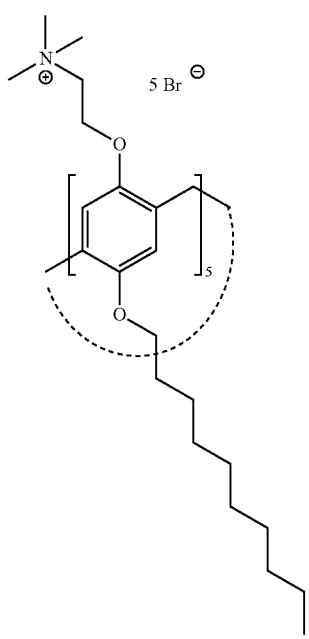

REFERENCES

Adiri, T.; Marciano, D.; Cohen, Y., *Chem. Commun.*, 2013, 49, 7082-7084

Benhamou, R. I.; Shaul, P.; Herzog, I. M.; Fridman, M., *Angew. Chem. Int. Ed.*, 2015, 54, 13617

Berkov-Zrihen, Y.; Herzog, I. M.; Feldman, M.; Sonn-Segev, A.; Roichman, Y.; Fridman, M., *Bioorg. Med. Chem.*, 2013, 21, 3624

Berkov-Zrihen, Y.; Herzog, I. M.; Benhamou, R. I.; Feldman, M.; Steinbuch, K. B.; Shaul, P.; Lerer, S.; Eldar, A.; Fridman, M., *Chem. Eur. J.*, 2015, 21, 4340

Bottcher, T.; Kolodkin-Gal, I.; Kolter, R.; Losick, R.; Clardy, J., *J. Am. Chem. Soc.*, 2013, 135, 2927

Chunju, L., *Chem. Commun.*, 2014, 50, 12420-12433

Cieniecka-Roslonkiewicz, A.; Pernak, J.; Kubis-Feder, J.; Ramani, A.; Robertson, A. J.; Seddon, K. R., *Green Chem.* 2005, 7, 855-862

Costerton, J. W.; Stewart, P. S.; Greenberg, E. P., *Science*, 1999, 284, 1318-1322

Cragg, P. J.; Sharma, K., *Chem. Soc. Rev.,* 2012, 41, 597-607
Davey, M. E.; O'Toole, G. A., *Microbiol. Mol. Biol. Rev.,* 2000, 64, 847
Davies, D., *Nat. Rev. Drug. Discovery,* 2003, 2, 114
Dong, S.; Zheng, B.; Wang, F.; Huang, F., *Acc. Chem. Res.,* 2014a, 47, 1982-1994
Dong, S.; Yuan, J.; Huang, F., *Chem. Sci.* 2014b, 5, 247-252
Feldman, M.; Tanabe, S.; Howell, A.; Garnier, D., *BMC Complement. Altern. Med.,* 2012, 12, 6
Fux, C. A.; Costerton, J. W.; Stewart, P. S.; Stoodley, P., *Trends Microbiol.,* 2005, 13, 34
Jennings M. C.; Ator, L. E.; Paniak, T. J.; Minbiole K. P. C.; Wuest, W. M., *ChemBioChem,* 2014, 15, 2211-2215
Jie, K.; Yao, Y.; Chi, X.; Huang, F., *Chem. Commun.* 2014, 50, 5503-5505
Joseph, R.; Naugolny, A.; Feldman, M.; Herzog, I. M.; Fridman, M.; Cohen, Y., *J. Am. Chem. Soc.,* 2016, 138, 754-757
Kanazawa, A.; Ikeda, T.; Endo, T., *J. Polym. Sci. Part A Polym. Chem.* 1993, 31, 335-343
Kanazawa, A.; Ikeda, T.; Endo, T., Antimicrob. Agents Chemother., 1994, 38, 945-952
Kurata, S.; Hamada, N.; Kanazawa, A.; Endo, T., *Dent. Mater. J.* 2011, 30, 960-966
Li, C., *Chem. Commun.,* 2014, 50, 12420-12433
Liz, D. G.; Manfredi, A. M.; Medeiros, M.; Montecinos, R.; Gomez-Gonzalez, B.; Garcia-Rio, L.; Nome, F., *Chem. Commun.,* 2016, 52, 3167-3170
Ma, Y.; Ji, X.; Xiang, F.; Chi, X.; Han, C.; He, J.; Abliz, Z.; Chen, W.; Huang, F., *Chem. Commun.,* 2011, 47, 12340
Ma, Y. J.; Cheng, L.; Li, C.; Mullen, K., *Chem. Commun.,* 2016, 52, 6662-6664
Mao, X.; Liu, T.; Bi, J.; Luo, L.; Tian, D.; Li, H., *Chem. Commun.* 2016, 52, 4385-4388
Nierengarten, I.; Nothisen, M.; Sigwalt, D.; Biellmann, T.; Holler, M.; Remy, J. S.; Nierengarten, J. F., *Chem. Eur. J.,* 2013, 19, 17552-17558
Ogoshi, T.; Kanai, S.; Fujinami, S.; Yamagishi, T.; Nakamoto, Y., *J. Am. Chem.* Soc., 2008, 130, 5022-5023
Ogoshi, T.; Ueshima, N.; Yamagishi, T.; Toyota, Y.; Matsumi, N., *Chem. Commun.,* 2012, 48, 3536-3538
Ogoshi, T.; Yamagishi, T., *Chem. Commun.,* 2014, 50, 4776-4787
Ogoshi, T.; Takashima, S.; Yamagishi, T., *J. Am. Chem. Soc.,* 2015, 137, 10962-10964
Ogoshi, T.; Akutsu, T.; Shimada, Y.; Yamagishi, T., *Chem. Commun.,* 2016, 52, 6479-6481
Omata, Y.; Folan, M.; Shaw, M.; Messer, R. L.; Lockwood, P. E.; Hobbs, D.; Bouillaguet, S.; Sano, H.; Lewis, J. B.; Wataha, J. C., *Toxicol In Vitro.* 2006, 20, 882-890
Pompilio, A.; Nicola, S. D.; Crocetta, V.; Guarnieri, S.; Savini, V.; Carretto, E.; Bonaventura, G. D., *BMC Microbiol.,* 2015, 15, 109
Rabin, N.; Zheng, Y.; Opoku-Temeg, C.; Du, Y.; Bonsu, E.; Sintim, H. O., *Future Med. Chem.,* 2015, 7, 493
Shi, B. B.; Jie, K. C.; Zhou, Y. J.; Zhou, J.; Xia, D. Y.; Huang, F. H., *J. Am. Chem. Soc.,* 2016, 138, 80-83
Wang, Q.; Cheng, M.; Zhao, Y.; Wu, L.; Jiang, J.; Wang, L.; Pan, Y., *Chem. Commun.* 2015, 51, 3623-3626
Wataha, J. C.; Craig, R. G.; Hanks, C. T., *Dent. Mater.,* 1992, 8, 65-71
Whiteside, M. S.; Kurrasch-Orbaugh, D.; Marona-Lewicka, D.; Nichols, D. E.; Monte, A., *Bioorg. Med. Chem.,* 2002, 10, 3301-3306
Wiegand, I.; Hilpert, K.; Hancock, R. E. W., *Nat. Protoc.,* 2008, 3, 163
Xue, M.; Yang, Y.; Chi, X.; Zhang, Z.; Huang, F., *Acc. Chem. Res.,* 2012, 45, 1294-1308
Xue, Y.; Xiao, H.; Zhang, Y., *Int. J. Mol. Sci.,* 2015, 16, 3626-3655
Yang, J.; Yu, G.; Xia, D.; Huang, F., *Chem. Commun.,* 2014, 50, 3993-3995
Yao, Y.; Xue, M.; Chi, X.; Ma, Y.; He, J.; Abliz, Z.; Huang, F., *Chem. Commun.,* 2012, 48, 6505
Yao, Y.; Chi, X.; Zhou, T.; Huang, F., *Chem. Sci.,* 2014, 5, 2778-2782
Zhang, H.; Zhao, Y., *Chem. Eur. J.,* 2013, 19, 16862-16879

What is claimed is:

1. A method for inhibiting or disrupting biofilm formation in an aqueous media or on an object, or for reducing biofilm existing in an aqueous media or attached to an object, said method comprising contacting said aqueous media or object with a compound of formula I:

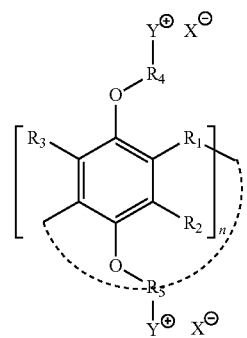

wherein $R_1$ is —$CR_6R_7$—, wherein $R_6$ and $R_7$ each independently is H, halogen, —$COR_8$, —$COOR_8$, —$OCOOR_8$, —$OCON(R_8)_2$, —CN, —$NO_2$, —$SR_8$, —$OR_8$, —$N(R_8)_2$, —$CON(R_8)_2$, —$SO_2R_8$, —$SO_3H$, —S(=O)$R_8$, or ($C_1$-$C_8$)alkyl optionally substituted by one or more groups each independently selected from the group consisting of —$COR_8$, —$COOR_8$, —$OCOOR_8$, —$OCON(R_8)_2$, —CN, —$NO_2$, —$SR_8$, —$OR_8$, —$N(R_8)_2$, —$CON(R_8)_2$, —$SO_2R_8$, —$SO_3H$, —S(=O)$R_8$, —$N^+(R')_3$ and —$P^+(R')_3$, wherein R' each independently is H, ($C_1$-$C_6$)alkyl, phenyl, benzyl, or heterocyclyl, or two R's together with the N atom to which they are attached form a 3-7 membered saturated ring, optionally containing one or more heteroatoms selected from the group consisting of O, S and N and optionally further substituted at the additional N atom;

$R_2$ and $R_3$ each independently is H, halogen, or ($C_1$-$C_8$) alkyl optionally substituted by one or more groups each independently selected from the group consisting of halogen, —$COR_8$, —$COOR_8$, —$OCOOR_8$, —OCON $(R_8)_2$, —CN, —$NO_2$, —$SR_8$, —$OR_8$, —$N(R_8)_2$, —$CON(R_8)_2$, —$SO_2R_8$, —$SO_3H$, —S(=O)$R_8$, —$N^+$ $(R')_3$ and —$P^+(R')_3$, wherein R' each independently is H, ($C_1$-$C_6$)alkyl, phenyl, benzyl, or heterocyclyl, or two R's together with the N atom to which they are attached form a 3-7 membered saturated ring, optionally containing one or more heteroatoms selected from the group consisting of O, S and N and optionally further substituted at the additional N atom;

$R_4$ and $R_5$ each independently is selected from the group consisting of ($C_1$-$C_{10}$)alkylene, ($C_2$-$C_{10}$)alkenylene, and ($C_2$-$C_{10}$)alkynylene, optionally substituted by one or more groups each independently selected from the group consisting of halogen, —COR$_8$, —COOR$_8$, —OCOOR$_8$, —OCON(R$_8$)$_2$, —CN, —NO$_2$, —SR$_8$, —OR$_8$, —N(R$_8$)$_2$, —CON(R$_8$)$_2$, —SO$_2$R$_8$, —SO$_3$H, —S(=O)R$_8$, (C$_6$-C$_{10}$)aryl, (C$_1$-C$_4$)alkylene-(C$_6$-C$_{10}$) aryl, hetero aryl, and (C$_1$-C$_4$)alkylene-hetero aryl, and further optionally interrupted by one or more identical or different heteroatoms selected from the group consisting of S, O and N, or by one or more groups each independently selected from the group consisting of —NH—CO—, —CO—NH—, —N(C$_1$-C$_8$alkyl)-, —N(C$_6$-C$_{10}$aryl)-, (C$_6$-C$_{10}$)arylenediyl, and heteroarylenediyl;

R$_8$ each independently is H or (C$_1$-C$_8$)alkyl;

Y each independently is (i) a cation derived from a nitrogen-containing group and selected from the group consisting of an ammonium [—N$^+$(R')$_3$], hydrazinium [—N$^+$(R')$_2$—N(R')$_2$], ammoniumoxy [—N$^+$(R')$_2$→O], iminium [—N$^+$(R')$_2$=C<], amidinium [—N$^+$(R')$_2$—C(R')=NR'], and guanidinium [—N$^+$(R')$_2$—C(=NR')—N(R')$_2$]; (ii) a cation derived from a nitrogen-containing mono- or polycyclic heteroaromatic group and selected from the group consisting of pyrazolium, imidazolium, oxazolium, thiazolium, pyridinium, pyrimidinium, quinolinium, isoquinolinium, 1,2,4-triazinium, 1,3,5-triazinium, and purinium, optionally substituted by one or more groups each independently selected from the group consisting of halogen, (C$_1$-C$_6$)alkyl, —COH, —COOH, —OCOOH, —OCONH$_2$, —CN, —NO$_2$, —SH, —OH, —NH$_2$, —CONH$_2$, —SO$_3$H, —SO$_2$H, and —S(=O)H; or (iii) a cation derived from an onium group not containing nitrogen and selected from the group consisting of phosphonium [—P$^+$(R')$_3$], arsonium [—As$^+$(R')$_3$], oxonium [—O$^+$(R')$_2$], sulfonium [—S$^+$(R')$_2$], selenonium [—Se$^+$(R')$_2$], telluronium [—Te$^+$(R')$_2$], stibonium [—Sb$^+$(R')$_3$], and bismuthonium [—Bi$^+$(R')$_3$]; wherein R' each independently is H, (C$_1$-C$_6$)alkyl, phenyl, benzyl, or heterocyclyl, or two R's in the ammonium, hydrazinium, ammoniumoxy, iminium, amidinium or guanidinium groups, together with the N atom to which they are attached, form a 3-7 membered saturated ring, optionally containing one or more heteroatoms selected from the group consisting of O, S and N and optionally further substituted at the additional N atom;

X is a counter anion; and n is an integer of 5-11.

2. The method of claim 1, for inhibiting or disrupting biofilm formation in an aqueous media, or for reducing biofilm existing in said aqueous media, wherein said contacting comprises dissolving said compound or a composition comprising it within said aqueous media.

3. The method of claim 1, for inhibiting or disrupting biofilm formation on an object, or for reducing biofilm attached to said object, wherein said contacting comprises coating said object with said compound or a composition comprising it, or immersing said object within a composition comprising said compound, respectively.

4. The method of claim 3, wherein said object is selected from the group consisting of an object designed for functioning in water, a medical implant, a medical device, and a biomedical pad.

5. The method of claim 4, wherein said object designed for functioning in water is selected from the group consisting of the hull of a boat, a pipe, a filter, a pump, and a heat-exchanger; said medical implant is a stent; said medical device is a catheter; and said biomedical pad is an adhesive bandage.

6. The method of claim 3, wherein said contacting comprises coating said object with a composition comprising said compound, and said composition is a paint.

7. The method of claim 1, wherein said method results in increased sensitivity of said aqueous media or object to a bacteriocide, and optionally further comprises contacting said aqueous media or object with said bacteriocide.

8. The method of claim 1, wherein:

(i) R$_1$ is —CR$_6$R$_7$—, wherein R$_6$ and R$_7$ each independently is H, halogen, —COH, —COOH, —OCOOH, —OCONH$_2$, —CN, —NO$_2$, —SH, —OH, —NH$_2$, —CONH$_2$, —SO$_3$H, —SO$_2$H, —S(=O)H, or (C$_1$-C$_8$) alkyl optionally substituted by one or more groups each independently selected from the group consisting of —COH, —COOH, —OCOOH, —OCONH$_2$, —CN, —NO$_2$, —SH, —OH, —NH$_2$, —CONH$_2$, —SO$_3$H, —SO$_2$H, —S(=O)H, —N$^+$(R')$_3$ or —P$^+$(R')$_3$, wherein R' each independently is H, (C$_1$-C$_4$)alkyl, phenyl, or benzyl; or (ii) R$_2$ and R$_3$ each independently is H, or (C$_1$-C$_4$)alkyl, optionally substituted by one or more groups each independently selected from the group consisting of halogen, —COH, —COOH, —OCOOH, —OCONH$_2$, —CN, —NO$_2$, —SH, —OH, —NH$_2$, —CONH$_2$, —SO$_3$H, —SO$_2$H, —S(=O)H, —N$^+$(R')$_3$ and —P$^+$(R')$_3$, wherein R' each independently is H, (C$_1$-C$_4$) alkyl, phenyl, or benzyl; or (iii) R$_4$ and R$_5$ each independently is (C$_2$-C$_{10}$)alkylene, optionally substituted by one or more groups each independently selected from the group consisting of halogen, —COH, —COOH, —OCOOH, —OCONH$_2$, —CN, —NO$_2$, —SH, —OH, —NH$_2$, —CONH$_2$, —SO$_3$H, —SO$_2$H, —S(=O)H, (C$_6$)aryl, (C$_1$-C$_4$)alkylene-(C$_6$)aryl, heteroaryl, and (C$_1$-C$_4$)alkylene-heteroaryl, and further optionally interrupted by one or more identical or different heteroatoms selected from the group consisting of S, O and N, or by one or more groups each independently selected from the group consisting of —NH—CO—, —CO—NH—, —N(C$_1$-C$_8$alkyl)-, —N(C$_6$aryl)-, (C$_6$)arylenediyl, and heteroarylenediyl; or (iv) R$_4$ and R$_5$ are identical; or (v) Y each independently is (i) ammonium [—N$^+$(R')$_3$] or phosphonium [—P$^+$(R')$_3$], wherein R' each independently is H, (C$_1$-C$_6$)alkyl, phenyl, benzyl, or heterocyclyl; or (ii) imidazolium, optionally substituted by one or more groups each independently selected from the group consisting of halogen, (C$_1$-C$_6$)alkyl, —COH, —COOH, —OCOOH, —OCONH$_2$, —CN, —NO$_2$, —SH, —OH, —NH$_2$, —CONH$_2$, —SO$_3$H, —SO$_2$H, and —S(=O)H; or (vi) n is 5, 6, 7 or 8.

9. The method of claim 8, wherein:

(i) R$_1$ is —CH$_2$—; or (ii) R$_2$ and R$_3$ are H; or (iii) R$_4$ and R$_5$ each independently is (C$_2$-C$_{10}$)alkylene, optionally interrupted by one or more O atoms; or (iv) Y each independently is ammonium [—N$^+$(R')$_3$] or phosphonium [—P$^+$(R')$_3$], wherein R' each independently is H, methyl, ethyl, or propyl; or 1-methyl-imidazolium-3-yl.

10. The method of claim 1, wherein:

R$_1$ is —CR$_6$R$_7$—, wherein R$_6$ and R$_7$ each independently is H, halogen, —COH, —COOH, —OCOOH, —OCONH$_2$, —CN, —NO$_2$, —SH, —OH, —NH$_2$, —CONH$_2$, —SO$_3$H, —SO$_2$H, —S(=O)H, or (C$_1$-C$_8$) alkyl optionally substituted by one or more groups each independently selected from the group consisting of —COH, —COOH, —OCOOH, —OCONH$_2$, —CN, —NO$_2$, —SH, —OH, —NH$_2$, —CONH$_2$, —SO$_3$H, —SO$_2$H, —S(=O)H, —N$^+$(R')$_3$ and —P$^+$(R')$_3$, wherein R' each independently is H, (C$_1$-C$_4$)alkyl, phenyl, or benzyl;

R$_2$ and R$_3$ each independently is H, or (C$_1$-C$_4$)alkyl, optionally substituted by one or more groups each independently selected from the group consisting of halogen, —COH, —COOH, —OCOOH, —OCONH$_2$, —CN, —NO$_2$, —SH, —OH, —NH$_2$, —CONH$_2$, —SO$_3$H, —SO$_2$H, —S(=O)H, —N$^+$(R')$_3$ and —P$^+$(R')$_3$, wherein R' each independently is H, (C$_1$-C$_4$) alkyl, phenyl, or benzyl;

R$_4$ and R$_5$ each independently is, optionally substituted by one or more groups each independently selected from the group consisting of halogen, —COH, —COOH, —OCOOH, —OCONH$_2$, —CN, —NO$_2$, —SH, —OH, —NH$_2$, —CONH$_2$, —SO$_3$H, —SO$_2$H, —S(=O)H, (C$_6$)aryl, (C$_1$-C$_4$)alkylene-(C$_6$)aryl, heteroaryl, and (C$_1$-C$_4$)alkylene-heteroaryl, and further optionally interrupted by one or more identical or different heteroatoms selected from the group consisting of S, O and N, or by one or more groups each independently selected from the group consisting of —NH—CO—, —CO—NH—, —N(C$_1$-C$_8$alkyl)-, —N(C$_6$aryl)-, (C$_6$) arylenediyl, and heteroarylenediyl; and n is 5, 6, 7 or 8.

11. The method of claim 10, wherein R$_1$ is —CH$_2$—; R$_2$ and R$_3$ are H; and R$_4$ and R$_5$ each independently is (C$_2$-C$_{10}$) alkylene, optionally interrupted by one or more O atoms.

12. The method of claim 11, wherein Y is (i) ammonium [—N$^+$(R')$_3$] or phosphonium [—P$^+$(R')$_3$], wherein R' each independently is H, (C$_1$-C$_6$)alkyl, phenyl, benzyl, or heterocyclyl; or (ii) imidazolium, optionally substituted by one or more groups each independently selected from the group consisting of halogen, (C$_1$-C$_6$)alkyl, —COH, —COOH, —OCOOH, —OCONH$_2$, —CN, —NO$_2$, —SH, —OH, —NH$_2$, —CONH$_2$, —SO$_3$H, —SO$_2$H, and —S(=O)H.

13. The method of claim 12, wherein Y each independently is ammonium [—N$^+$(R')$_3$] or phosphonium [—P$^+$(R')$_3$], wherein R' each independently is H, methyl, ethyl, or propyl; or 1-methyl-imidazolium-3-yl.

14. The method of claim 13, wherein n is 5 or 6.

15. The method of claim 14, wherein R$_1$ is —CH$_2$—; R$_2$ and R$_3$ are H; R$_4$ and R$_5$ are identical and each one is —(CH$_2$)$_{2-10}$—; Y is —N$^+$(CH$_3$)$_3$, —N$^+$(C$_2$H$_5$)$_3$, —P$^+$(CH$_3$)$_3$, —P$^+$(C$_2$H$_5$)$_3$, or 1-methyl-imidazolium-3-yl; n is 5 or 6; and X is a counter anion.

16. The method of claim 15, wherein R$_1$ is —CH$_2$—; R$_2$ and R$_3$ are H; R$_4$ and R$_5$ are —(CH$_2$)$_2$—; Y is —N$^+$(CH$_3$)$_3$; n is 5; and X is a counter anion.

17. The method of claim 1, wherein said counter anion is Br$^-$, Cl$^-$, F$^-$, I$^-$, PF$_6^-$, BF$_4^-$, OH$^-$, ClO$_4^-$, HSO$_4^-$, CF$_3$COO$^-$, CN$^-$, alkylCOO$^-$, arylCOO$^-$, a pharmaceutically acceptable anion, or a combination thereof.

* * * * *

UNITED STATES PATENT AND TRADEMARK OFFICE
CERTIFICATE OF CORRECTION

PATENT NO. : 11,161,801 B2  
APPLICATION NO. : 15/751786  
DATED : November 2, 2021  
INVENTOR(S) : Yoram Cohen et al.

Page 1 of 2

It is certified that error appears in the above-identified patent and that said Letters Patent is hereby corrected as shown below:

On the Title Page

Column 2 (Item (56) Other publications), Line 19, delete "futurew"" and insert -- future" --.

Column 2 (Item (56) Other publications), Line 30, delete "omplexation" and insert -- complexation --.

Column 2 (Item (56) Other publications), Line 30, delete "1-octanesulfonatew"" and insert -- 1-octanesulfonate" --.

In the Specification

Column 1, Line 3 (approx.), below "THEREOF" insert -- CROSS REFERENCE TO RELATED APPLICATIONS --.

Column 2, Line 4, delete "Bacillus" and insert -- bacillus --.

Column 2, Line 4, delete "subtillis" and insert -- subtilis --.

Column 3, Line 21, delete "—P+(R')$_3$" and insert -- —N+(R')$_3$ --.

Column 3, Line 40, delete "(C$_1$-C$_5$)alkyl;" and insert -- (C$_1$-C$_8$)alkyl; --.

Column 3, Line 65, delete "[—N+(R')$_2$—N+(R')$_2$]," and insert -- [—N+(R')$_2$—N(R')$_2$], --.

Column 4, Line 12 (approx.), delete "oxonium" and insert -- oxonium [-O+(R')$_2$], --.

Column 14, Line 20, delete "—(CH$_2$)$_{11}$);" and insert -- —(CH$_2$)$_{10}$; --.

Column 17, Line 1, delete "(6)" and insert -- (δ) --.

Signed and Sealed this  
Tenth Day of May, 2022

Katherine Kelly Vidal  
*Director of the United States Patent and Trademark Office*

Column 21, Line 12, delete "[M+Bi]⁻" and insert -- [M+Br]⁻ --.

Column 23, Line 3, delete "Biofilin" and insert -- Biofilm --.

Column 23, Line 32 (approx.), delete "-dimethylthiazoyl" and insert -- -dimethylthiazolyl --.

In the Claims

Column 45, Line 6, in Claim 1, delete "hetero aryl," and insert -- heteroaryl, --.

Column 45, Line 6, in Claim 1, delete "hetero aryl," and insert -- heteroaryl, --.